US012692469B2

(12) United States Patent
DaSilva et al.

(10) Patent No.: US 12,692,469 B2
(45) Date of Patent: Jul. 28, 2026

(54) MODULAR INCUBATORS FOR CONFIGURABLE WORKSTATIONS

(71) Applicant: CooperSurgical, Inc., Trumbull, CT (US)

(72) Inventors: Rodrigo DaSilva, Trumbull, CT (US); Shuo Robert Chen, White Plains, NY (US); Adam H Morales, Trumbull, CT (US); Wilfrido Enrique Thalliens Angulo, Cornwall (GB); Timothy Stanhope, Cornwall (GB)

(73) Assignee: CooperSurgical, Inc., Trumbull, CT (US)

( * ) Notice: Subject to any disclaimer, the term of this patent is extended or adjusted under 35 U.S.C. 154(b) by 846 days.

(21) Appl. No.: 17/872,267

(22) Filed: Jul. 25, 2022

(65) Prior Publication Data

US 2023/0112758 A1 Apr. 13, 2023

Related U.S. Application Data

(60) Provisional application No. 63/253,171, filed on Oct. 7, 2021.

(51) Int. Cl.
*C12M 1/00* (2006.01)
*B01L 1/00* (2006.01)
(Continued)

(52) U.S. Cl.
CPC ........... *C12M 41/14* (2013.01); *C12M 23/04* (2013.01); *C12M 23/22* (2013.01); *C12M 41/34* (2013.01)

(58) Field of Classification Search
None
See application file for complete search history.

(56) References Cited

U.S. PATENT DOCUMENTS 2,944,134 A * 7/1960 Kenyon .................. C12M 23/54
219/521
4,863,223 A 9/1989 Weissenbach et al.
(Continued)

FOREIGN PATENT DOCUMENTS

EP 1609541 12/2005
EP 2640519 9/2013
(Continued)

OTHER PUBLICATIONS

YouTube video titled "Astec MN2 incubator part 3", posted Apr. 20, 2021 by Fusion Fertility <https://www.youtube.com/watch?v=aSS6hiHeqRg> (Year: 2021).*
(Continued)

*Primary Examiner* — Holly Kipouros
(74) *Attorney, Agent, or Firm* — Fish & Richardson P.C.

(57) ABSTRACT

A modular incubator includes a housing including one or more fastening mechanisms for attachment to a workstation frame, a platform located at the housing and defining a sample placement area, and a chamber wall structure coupled to the platform. The chamber wall structure is pivotable between a closed position against the platform to form a sample chamber and an open position in which a front end of the chamber wall structure is spaced apart from the platform to allow access to the sample placement area. The modular incubator further includes a lid coupled to and openable from the chamber wall structure to expose at least a portion of the chamber wall structure for viewing.

23 Claims, 45 Drawing Sheets

(51) Int. Cl.

| | |
|---|---|
| B01L 9/02 | (2006.01) |
| C12M 1/04 | (2006.01) |
| C12M 1/12 | (2006.01) |
| C12M 1/34 | (2006.01) |

(56) References Cited

U.S. PATENT DOCUMENTS

| | | | |
|---|---|---|---|
| 7,028,913 | B2 | 4/2006 | Reinhardt et al. |
| 7,712,847 | B1 | 5/2010 | Albright et al. |
| 7,718,423 | B2 | 5/2010 | Tsuchiya |
| 9,055,812 | B2 | 6/2015 | Fishman et al. |
| 9,060,598 | B2 | 6/2015 | Isgro |
| 9,505,002 | B2 | 11/2016 | Momboisse et al. |
| 9,516,944 | B2 | 12/2016 | Lawrence |
| 9,732,314 | B2 | 8/2017 | Shibata et al. |
| 9,751,084 | B2 | 9/2017 | Greenizen et al. |
| 9,902,930 | B2 | 2/2018 | Pieczarek et al. |
| 10,226,120 | B2 | 3/2019 | Chau |
| 10,307,802 | B2 | 6/2019 | Ross et al. |
| 10,407,659 | B2 | 9/2019 | Jaffal |
| 10,549,271 | B2 | 2/2020 | Dockrill et al. |
| 12,508,584 | B2 | 12/2025 | Chen et al. |
| 2005/0248836 | A1* | 11/2005 | Tsuchiya .............. G02B 21/362 |
| | | | 359/368 |
| 2009/0020442 | A1 | 1/2009 | Dietrich |
| 2009/0024699 | A1 | 1/2009 | Eichenseer |
| 2010/0151564 | A1 | 6/2010 | Beebe et al. |
| 2012/0158882 | A1 | 6/2012 | Oehme |
| 2012/0184028 | A1* | 7/2012 | Swanson ................ C12M 23/10 |
| | | | 435/303.1 |
| 2013/0109081 | A1* | 5/2013 | Tsuchiya ................ G02B 21/30 |
| | | | 435/286.1 |
| 2014/0087455 | A1 | 3/2014 | Kobayashi |
| 2014/0356934 | A1* | 12/2014 | Barka .................... C12M 41/14 |
| | | | 435/286.1 |
| 2016/0089673 | A1* | 3/2016 | Mccarthy .............. C12M 23/16 |
| | | | 435/305.1 |
| 2017/0023561 | A1 | 1/2017 | Gispert-Sauch |
| 2017/0145372 | A1 | 5/2017 | Hansen et al. |
| 2018/0002649 | A1 | 1/2018 | Pedersen |
| 2018/0104697 | A1 | 4/2018 | Butler et al. |
| 2018/0320122 | A1 | 11/2018 | Blanchard |
| 2018/0340142 | A1 | 11/2018 | Liu et al. |
| 2019/0017008 | A1* | 1/2019 | Pahara ................... C12M 23/06 |
| 2019/0024036 | A1* | 1/2019 | Hitomi ................... C12M 41/48 |
| 2019/0099757 | A1* | 4/2019 | Sekizawa ............ G01N 21/645 |
| 2019/0252072 | A1 | 8/2019 | Parker |
| 2019/0308195 | A1 | 10/2019 | Meier et al. |
| 2019/0376012 | A1 | 12/2019 | Pedersen |
| 2019/0377370 | A1 | 12/2019 | Schuck et al. |
| 2020/0148993 | A1* | 5/2020 | Wente ................... C12M 41/14 |
| 2020/0162355 | A1 | 5/2020 | Zacks |
| 2021/0106984 | A1 | 4/2021 | Chen et al. |
| 2021/0155978 | A1 | 5/2021 | Tidd |
| 2022/0121857 | A1* | 4/2022 | Singhal .................. H04W 4/80 |
| 2022/0340856 | A1* | 10/2022 | Black .................... C12M 23/52 |

FOREIGN PATENT DOCUMENTS

| | | |
|---|---|---|
| EP | 3109641 | 12/2016 |
| GB | 2501283 | 10/2013 |
| WO | WO 1990/005549 | 5/1990 |
| WO | WO 2014/086984 | 6/2014 |
| WO | WO 2018/164232 | 9/2018 |
| WO | WO 2019/014239 | 1/2019 |
| WO | WO 2019/103225 | 5/2019 |
| WO | WO 2019/207892 | 10/2019 |

OTHER PUBLICATIONS

Amino Labs, video titled Discover the DNA Playground, published Dec. 5, 2016, retrieved Dec. 16, 2025 <https://www.youtube.com/watch?v=ztMFrwg3CXs> (Year: 2016).*

International Preliminary Report on Patentability in International Appln. No. PCT/US2022/074098, mailed on Apr. 18, 2024, 9 pages.

Astec, "MN-2," Apr. 11, 2021, Retrieved from the Internet URL <https://web.archive.org/web/20210411133417if_/https://www.astec-bio.com/global/img/top/catalog/MN-2_catalog.pdf>, 3 pages.

International Search Report and Written Opinion in International Appln. No. PCT/US2022/074098, mailed on Nov. 8, 2022, 16 pages.

Office Action in Australian Appln. No. 2022360052, mailed on May 22, 2025, 4 pages.

Esco Medical [online], "Ensure Optimal Results for Embryo Manipulation During IVF with Esco Multi-Zone ART Workstation," Sep. 26, 2019, retrieved on Sep. 12, 2025, retrieved from URL<https://www.youtube.com/watch?v=Czd2PotJreA>, 3 pages with machine transcript.

\* cited by examiner

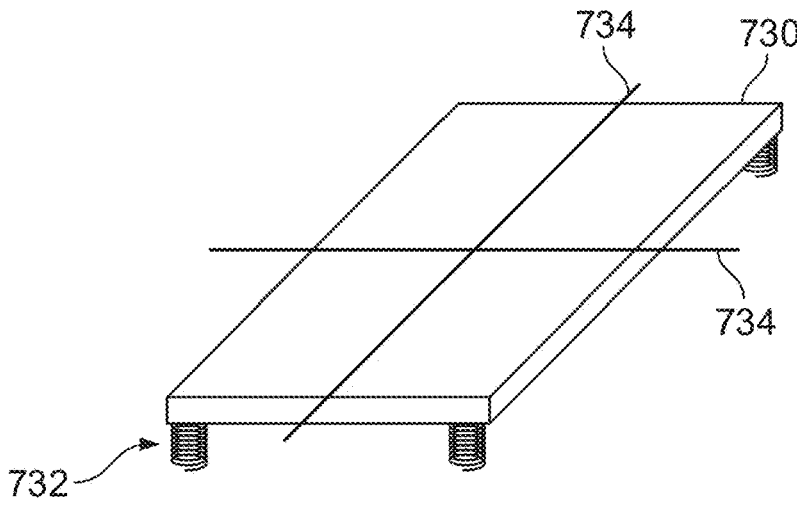
FIG. 31
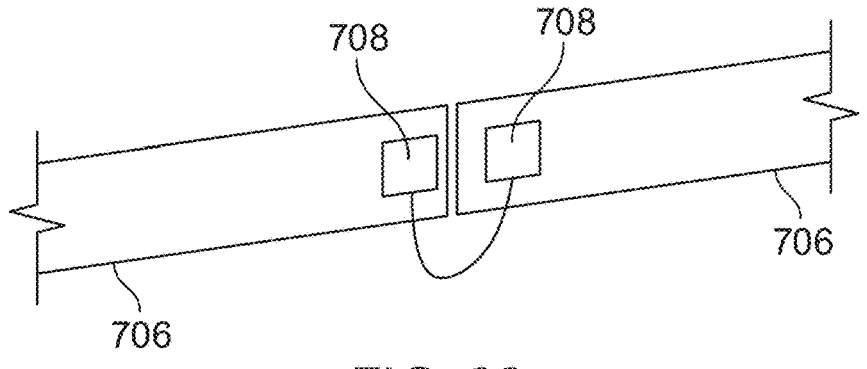
FIG. 32
FIG. 33

1000

882

884

1000

886

1002, 1004

MODULAR INCUBATORS FOR CONFIGURABLE WORKSTATIONS

CROSS-REFERENCE TO RELATED APPLICATIONS

This application claims priority to U.S. Provisional Patent Application No. 63/253,171, filed on Oct. 7, 2021. The entire content of this application is incorporated herein by reference.

TECHNICAL FIELD

This disclosure relates to modular incubators that can be selectively installed to configurable workstations, such as modularized workstations that are configurable on-site at laboratories for carrying out biological protocols.

BACKGROUND

Biosafety cabinets provide a workspace for carrying out various biological protocols, such as protocols for carrying out in vitro fertilization (IVF) and other biological procedures. Biosafety cabinets are generally configured with a specific design that meets a customer's requirements. As a result of advanced training, expertise, and dexterity required to perform IVF procedures, embryologists in different laboratories typically have specific requirements for layouts of work areas in order to perform the procedures easily and most efficiently. Such requirements drive a large variety of configurations and versions of biosafety cabinets, which leads to high costs of maintaining such products and high costs of controlling product quality. In some examples, a biosafety cabinet is equipped with a built-in incubator that includes a sample chamber or a shelf in or on which a sample container can be placed after being lifted from tabletop surface of the biosafety cabinet. While equipment technologies for IVF are advancing rapidly, such new technologies cannot be easily integrated into the small workspaces of existing biosafety cabinets.

SUMMARY

In general, this disclosure relates to configurable workstations (e.g., biosafety cabinets) for carrying out biological protocols (e.g., IVF protocols) in a laboratory environment. The configurable workstations are networked systems that provide regulatory independence for system sub-components of different regulatory classes. Furthermore, the configurable workstations have a modularized design that is customizable on-site at a laboratory to meet various environmental and functional requirements. Accordingly, various functional modules can be selectively installed to a support frame of such a configurable workstation. For example, in some embodiments, a an incubator module may be installed to a tabletop surface of the support frame to provide an incubator functionality for a sample that is temporarily handled at the configurable workstation as part of a scientific protocol. The incubator module provides a sample chamber that is formed as an inverted pocket against a flat, horizontal platform that lies flush with the tabletop surface of the support frame.

In one aspect, a modular incubator includes a housing including one or more fastening mechanisms for attachment to a workstation frame, a platform located at the housing and defining a sample placement area, and a chamber wall structure coupled to the platform. The chamber wall structure is pivotable between a closed position against the platform to form a sample chamber and an open position in which a front end of the chamber wall structure is spaced apart from the platform to allow access to the sample placement area. The modular incubator further includes a lid coupled to and openable from the chamber wall structure to expose at least a portion of the chamber wall structure for viewing Embodiments may include one or more of the following features.

In some embodiments, the portion of the chamber wall structure is transparent or translucent.

In some embodiments, the portion of the chamber wall structure includes a glass plate.

In some embodiments, the glass plate is coated with a conductive layer.

In some embodiments, the chamber wall structure includes an inverted pocket.

In some embodiments, the entire chamber wall structure is transparent.

In some embodiments, the chamber wall structure includes a double-layer wall and a gasket within the double-layer wall for sealing the chamber wall structure to the platform in the closed position.

In some embodiments, the chamber wall structure is coupled to the platform at a torque hinge.

In some embodiments, one or both of the chamber wall structure and the lid includes an insulation material.

In some embodiments, the chamber wall structure includes a handle that is coupled to a complementary feature of the lid such that a pivotal movement of the handle causes a corresponding pivotal movement of the lid.

In some embodiments, the handle includes a lip, a tab, or a pocket.

In some embodiments, the sample placement area includes multiple positional regions for respective placement of multiple sample containers.

In some embodiments, the modular incubator further includes a gas distributor located at a center position of the sample placement area.

In some embodiments, the gas distributor is configured to equally distribute a flow of gas towards each positional region of the plurality of positional regions.

In some embodiments, the modular incubator further includes multiple RFID sensors respectively associated with the multiple positional regions.

In some embodiments, each RFID sensor of the multiple RFID sensors forms an outline around a respective positional region of the multiple positional regions.

In some embodiments, the housing includes an internal heating element.

In some embodiments, the lid includes a heating element.

In some embodiments, the modular incubator further includes a sensor that detects a closed state and an open state of the chamber wall structure.

In some embodiments, the modular incubator further includes a user interface for inputting operational parameters of the incubator module.

In another aspect, a configurable workstation includes a support frame defining a workspace for carrying out a scientific protocol and a modular incubator that is configured to be selectively installed to the support frame for providing an incubation functionality at the workspace. The modular incubator includes a housing including one or more fastening mechanisms for attachment to the support frame, a platform located at the housing and defining a sample placement area, and a chamber wall structure coupled to the platform. The chamber wall structure is pivotable between a closed position against the platform to form a sample chamber and an open position in which a front end of the chamber wall structure is spaced apart from the platform to allow access to the sample placement area. The modular incubator further includes a lid coupled to and openable from the chamber wall structure to expose at least a portion of the chamber wall structure for viewing.

Embodiments may provide one or more of the following advantages.

The configurable workstation has a modularized design that is customizable on-site at a laboratory to meet various laboratory requirements and provide selected functional capabilities. The customizable design of the configurable workstation facilitates upgrading of existing technologies and integration of new technologies at the configurable workstation without replacing the configurable workstation with an entirely new workstation at significant cost and laboratory downtime. For example, by selectively installing desired modules at a workstation frame, a functional profile of the configurable workstation may be customized to provide capabilities required to carry out certain experimental procedures, to meet certain requirements of a laboratory at which the workstation is located, or to identify specimens in a certain manner.

Furthermore, as long as power is supplied to a module at a built-in power port, the modules can operate even without installation to the frame and can perform their intended functionalities without connection to a web application implemented on a server computer of the configurable workstation. In some embodiments, the web application can be accessed to allow the user to control all functions of the frame and the modules from a single location.

In some embodiments, the modular incubator is advantageously designed to allow a user to slide a specimen container from an adjacent tabletop surface of the configurable workstation onto a flat, horizontal incubation platform without having to first lift the sample container from the tabletop surface so as to avoid mechanically disturbing the sample and the surrounding interior environment within the container. This capability is provided by a chamber wall structure that is openable from the platform to allow access to positional regions along a sample surface area on the platform and closeable against the platform to form a sample chamber (e.g., an inverted pocket) around one or more sample containers positioned at one or more selected positional regions. Furthermore, all or part of the chamber wall structure is transparent, such that an outer lid of the modular incubator can be opened independently of a position of the chamber wall structure to expose the chamber wall structure for viewing a sample container located within the sample chamber. Maintaining the chamber wall structure in a closed position while viewing the sample container prevents gases and heat from escaping the sample chamber during viewing.

Advantageously, the modular incubator also includes a centrally positioned gas distributor for equally distributing a flow of gas among the multiple positional regions. The modular incubator also includes heating elements in either or both of the platform and the lid for producing a substantially uniform heat distribution across the sample chamber. The gas distribution configuration and the heating configuration promote a relatively fast recovery of desired conditions within the sample chamber upon closure of the chamber wall structure against the platform.

The network communication architecture on which the configurable workstation operates alleviates privacy and performance concerns related to handling and storing medical data by supporting the devices (e.g., such as the frame and the modules) on a local network to reduce a chance of unauthorized access to the devices and data stored on or transferred by the devices. The network communication architecture is also flexible to handle a variable number of devices without prior customization at a factory.

The devices can communicate with each other through a local mesh network and with the server computer independently of the other devices such that if one device malfunctions, the operation of the remaining devices will not be hindered or affected. In this manner, the network communication architecture ensures device independence. Not only is independence of the devices important for certain customer needs and technically robust, but such independence advantageously allows independent handling (e.g., access and control) of devices in distinct regulatory classes. Accordingly, a regulatory approval status for one device will not affect a regulatory approval status of another device.

In some embodiments, the configurable workstation defines an airflow path along which air flows laterally, forwardly, and rearwardly at a frame to advantageously avoid contact with certain components of the configurable workstation and a specimen handled in a workspace of the configurable workstation to reduce the likelihood of contaminating the specimen and such components. Furthermore, the configurable workstation is designed such that the airflow path is unaffected by the combination of modules selectively installed at the frame. Independence of the airflow path from the modules advantageously permits factory testing of the airflow path prior to shipment of the configurable workstation to a customer site. Furthermore, an air duct system may be disassembled from the frame of the configurable workstation to convert the configurable workstation from a Class II biosafety cabinet to a Class I biosafety cabinet, avoiding the need to acquire an entirely new biosafety cabinet that meets Class I requirements.

DESCRIPTION OF DRAWINGS

FIG. 2 is a rear perspective view of the configurable workstation of FIG. 1.

5                                                                        6

Figures 5, 6:
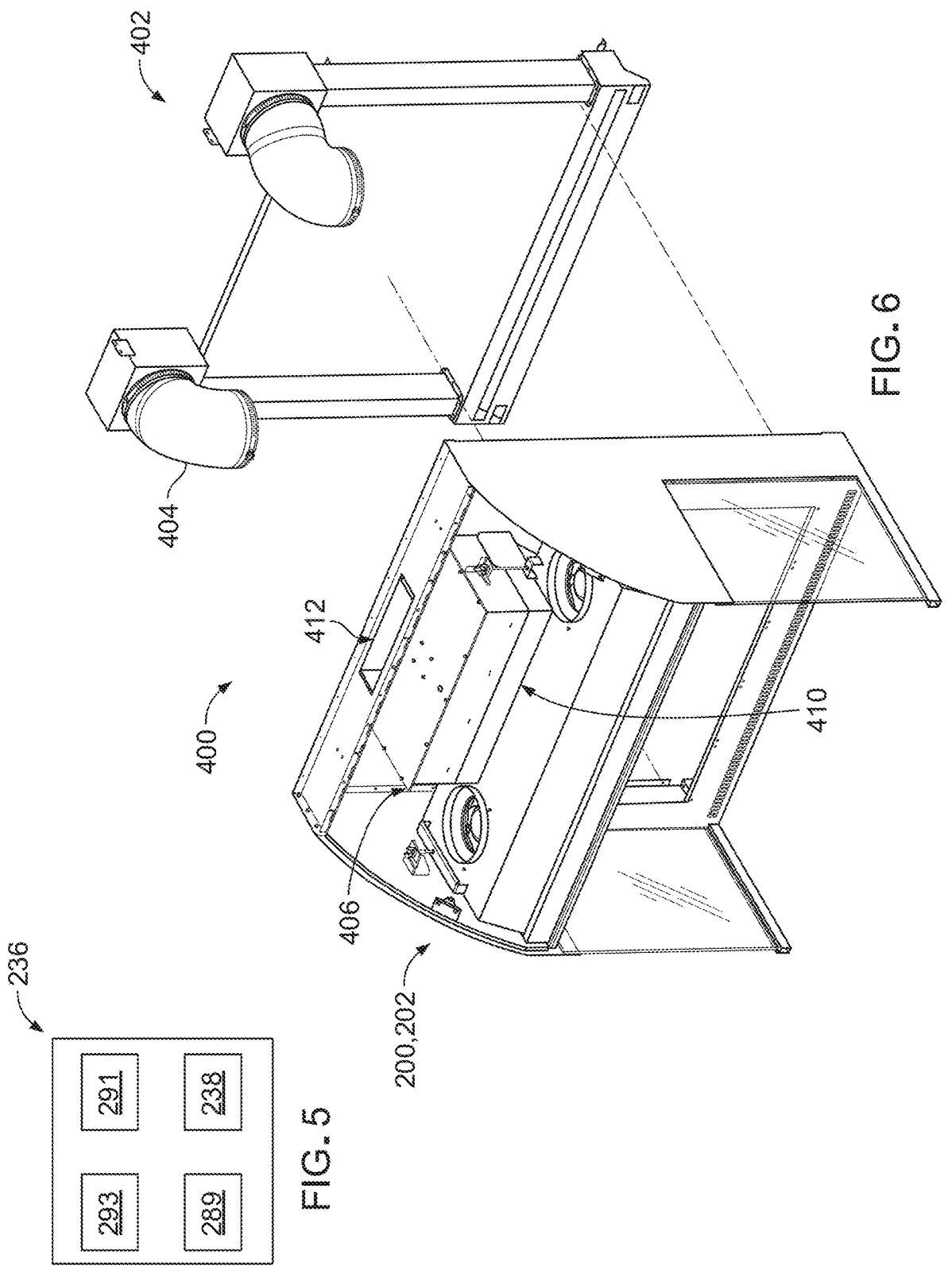
FIG. 5 is a schematic illustration of a control module of the configurable workstation of FIG. 1.
FIG. 6 is an exploded view of a portion of an upper panel structure and an air duct frame of the configurable workstation of FIG. 1.
Figure 7:
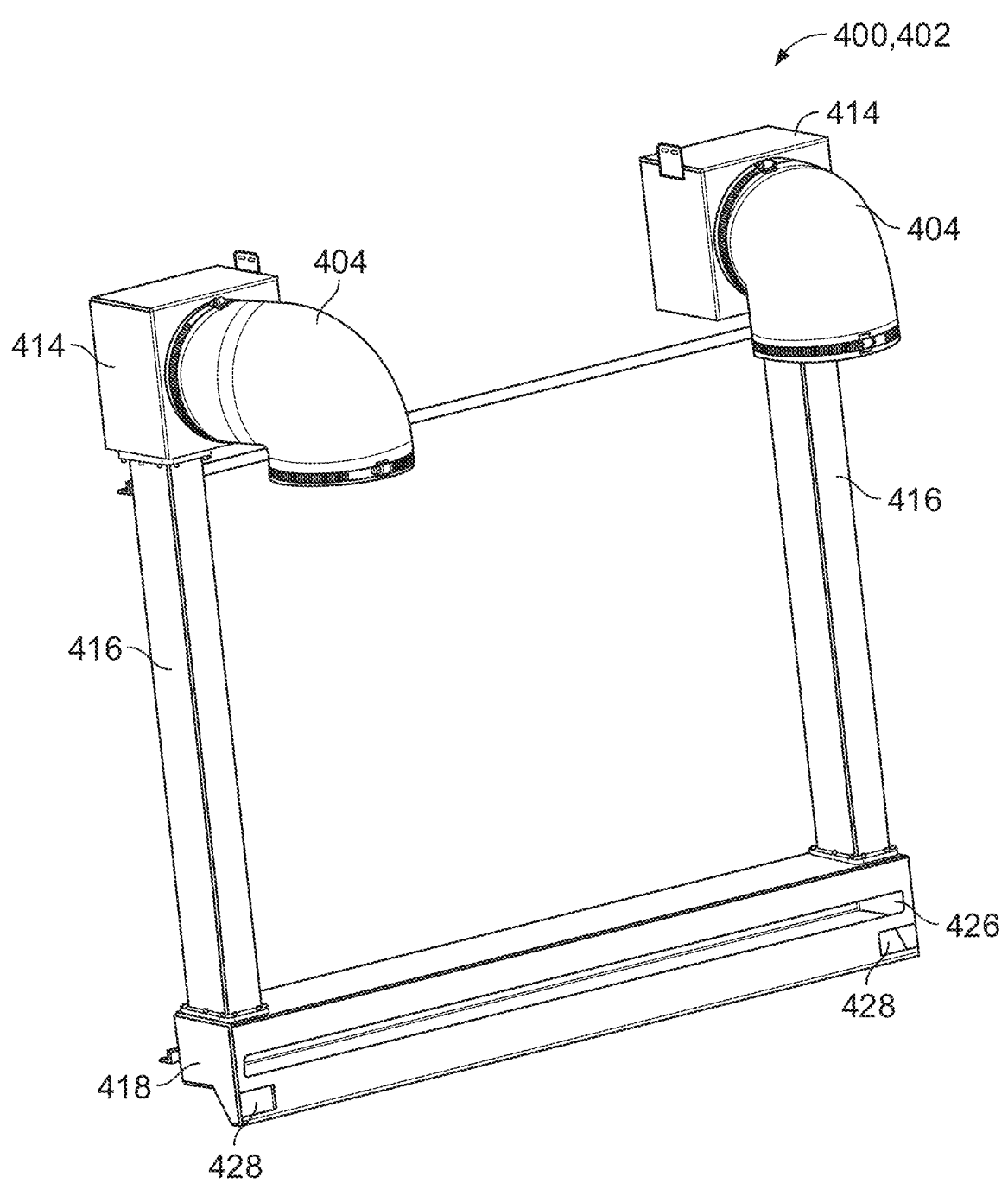
FIG. 7 is a front perspective view of the air duct frame of FIG. 6.
Figure 8:
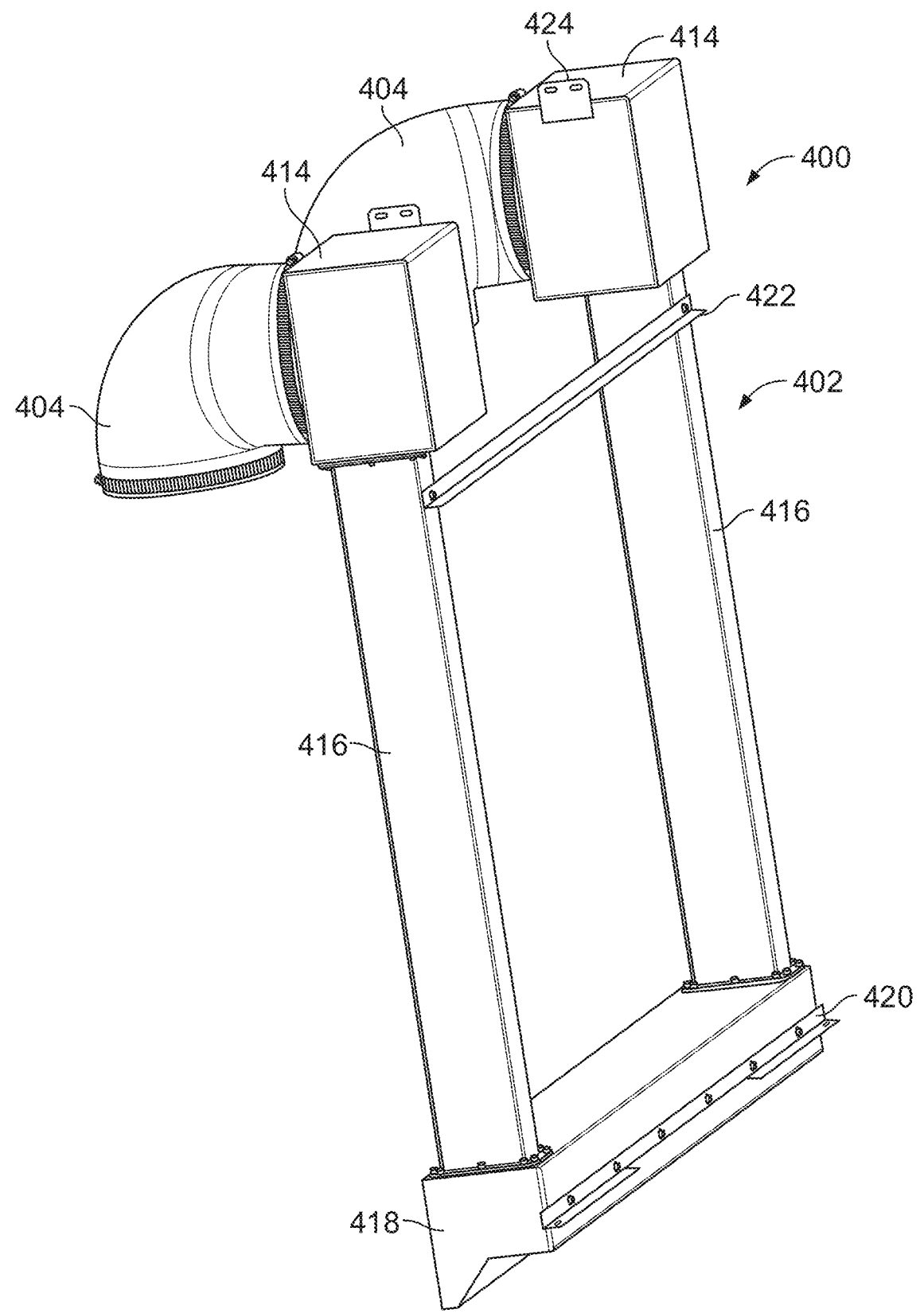
FIG. 8 is a rear perspective view of the air duct frame of FIG. 6.
Figure 11:
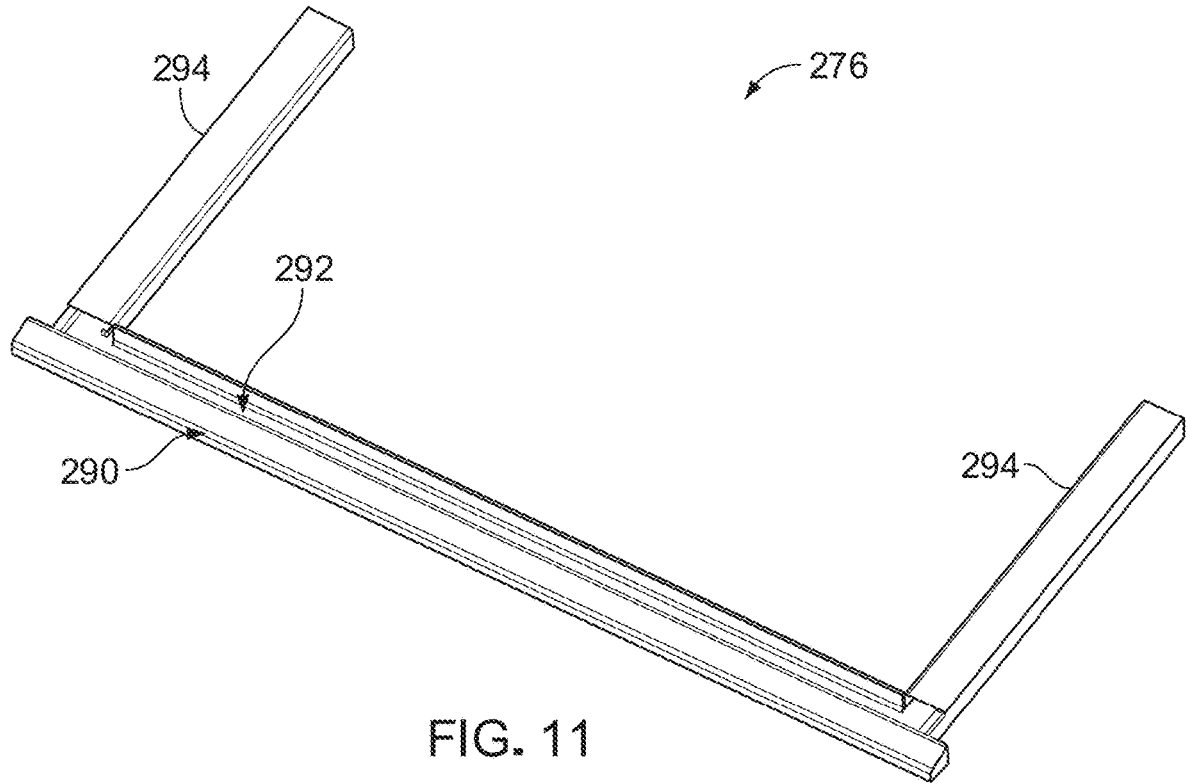
FIG. 11 is a perspective view of a slidable air duct of the table of FIG. 10.
Figure 12:
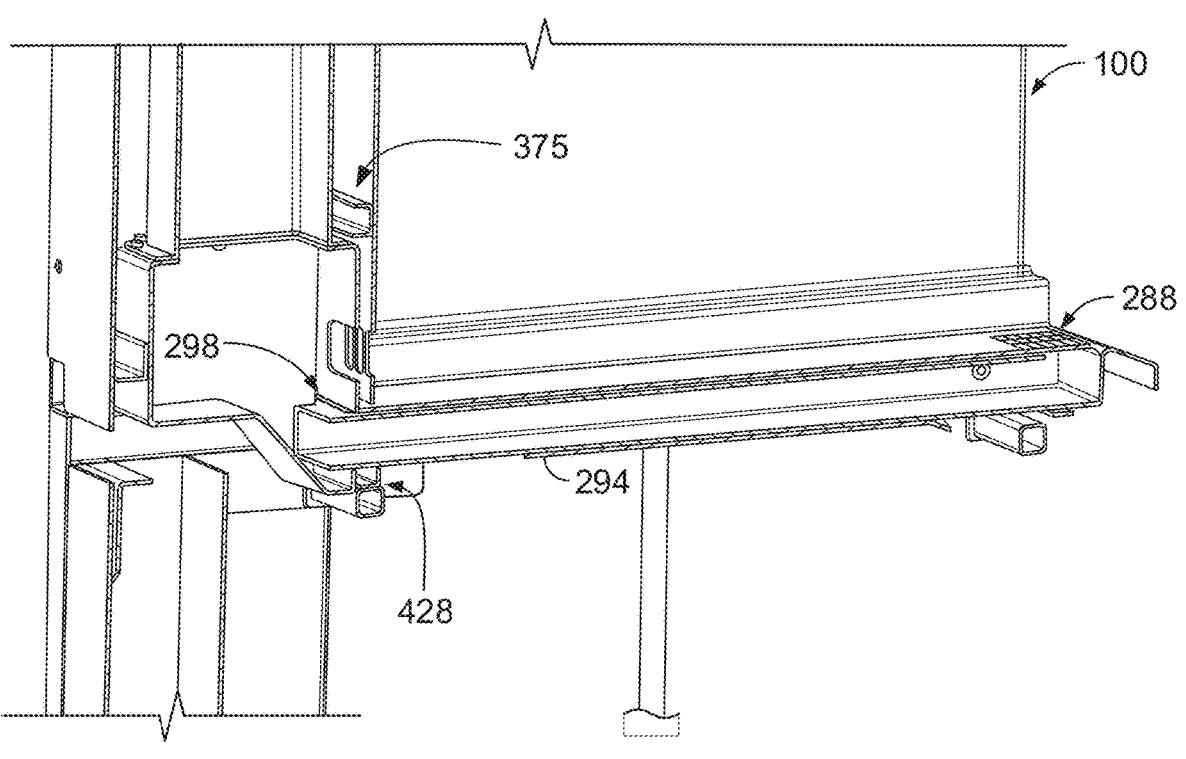

FIG. 12 is an enlarged perspective view of an interface between the slidable air duct of FIG. 11 and the air duct frame of FIG. 6.

Figure 13:
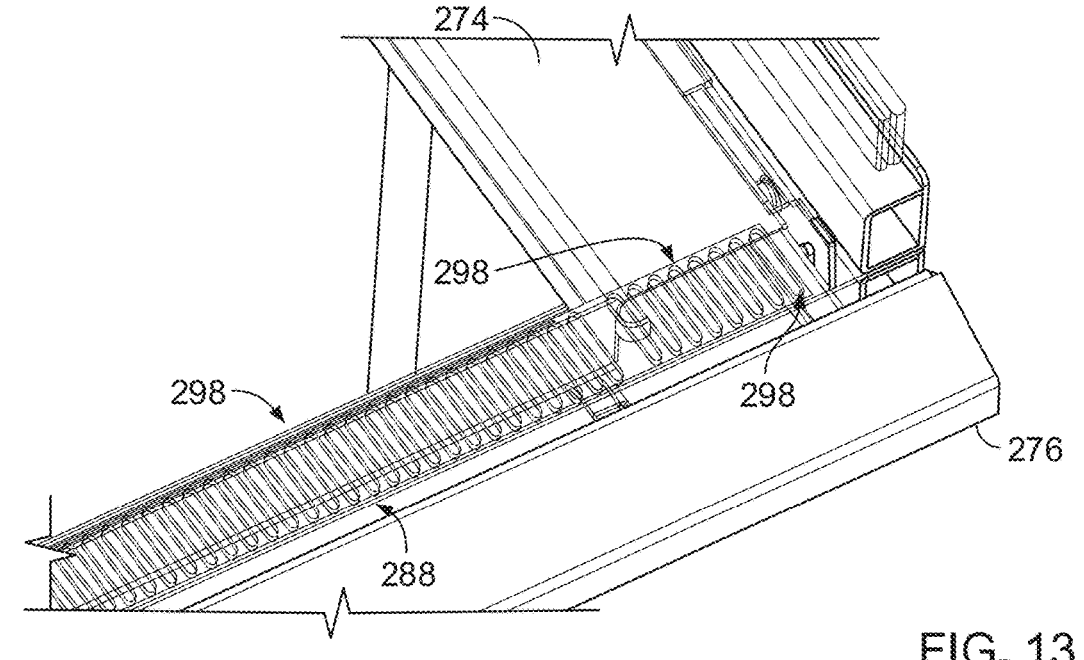

FIG. 13 is an enlarged perspective view of a frontal portion of the table of FIG. 6.

Figure 1:
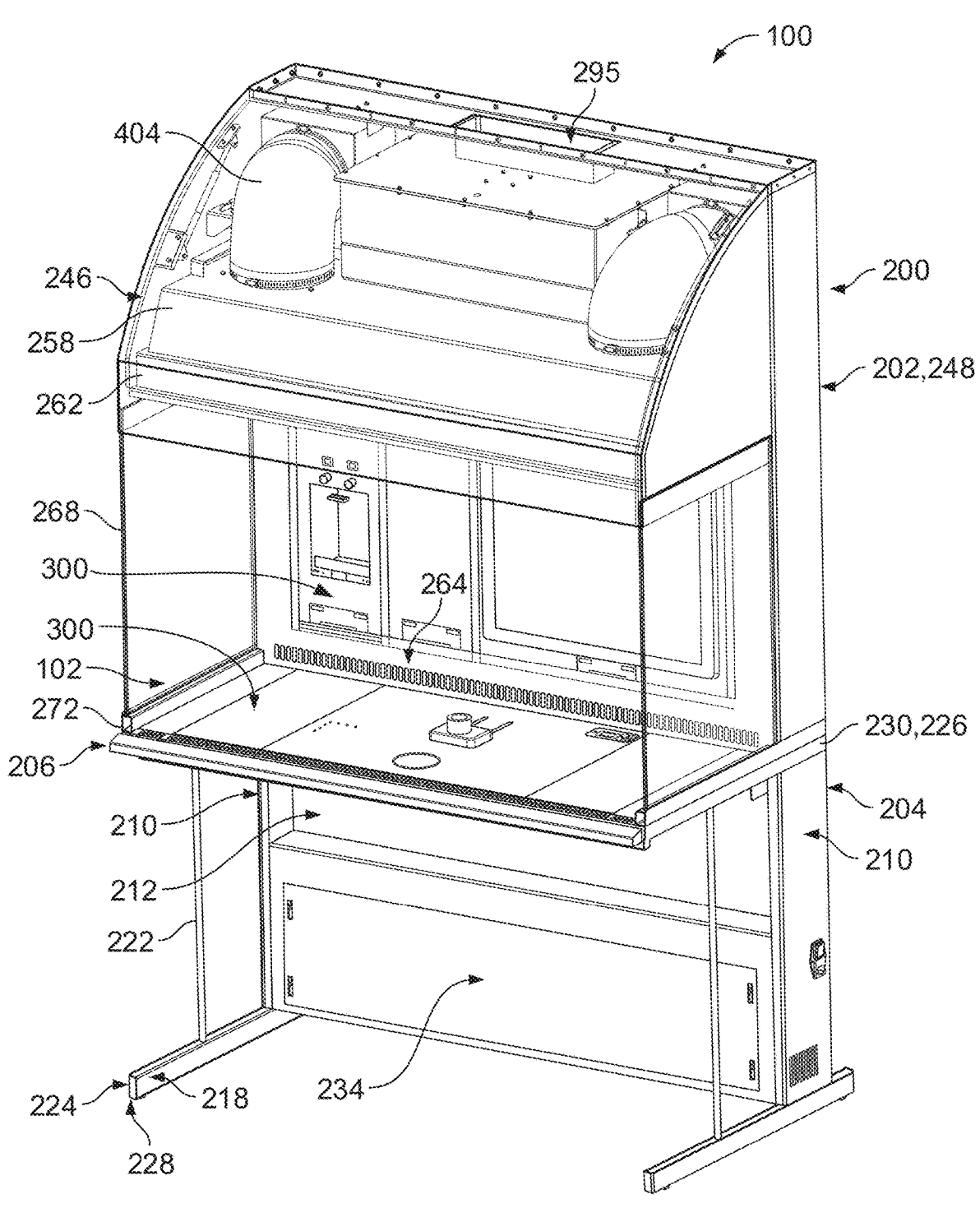
FIG. 1 is a front perspective view of a configurable workstation.
Figure 14:
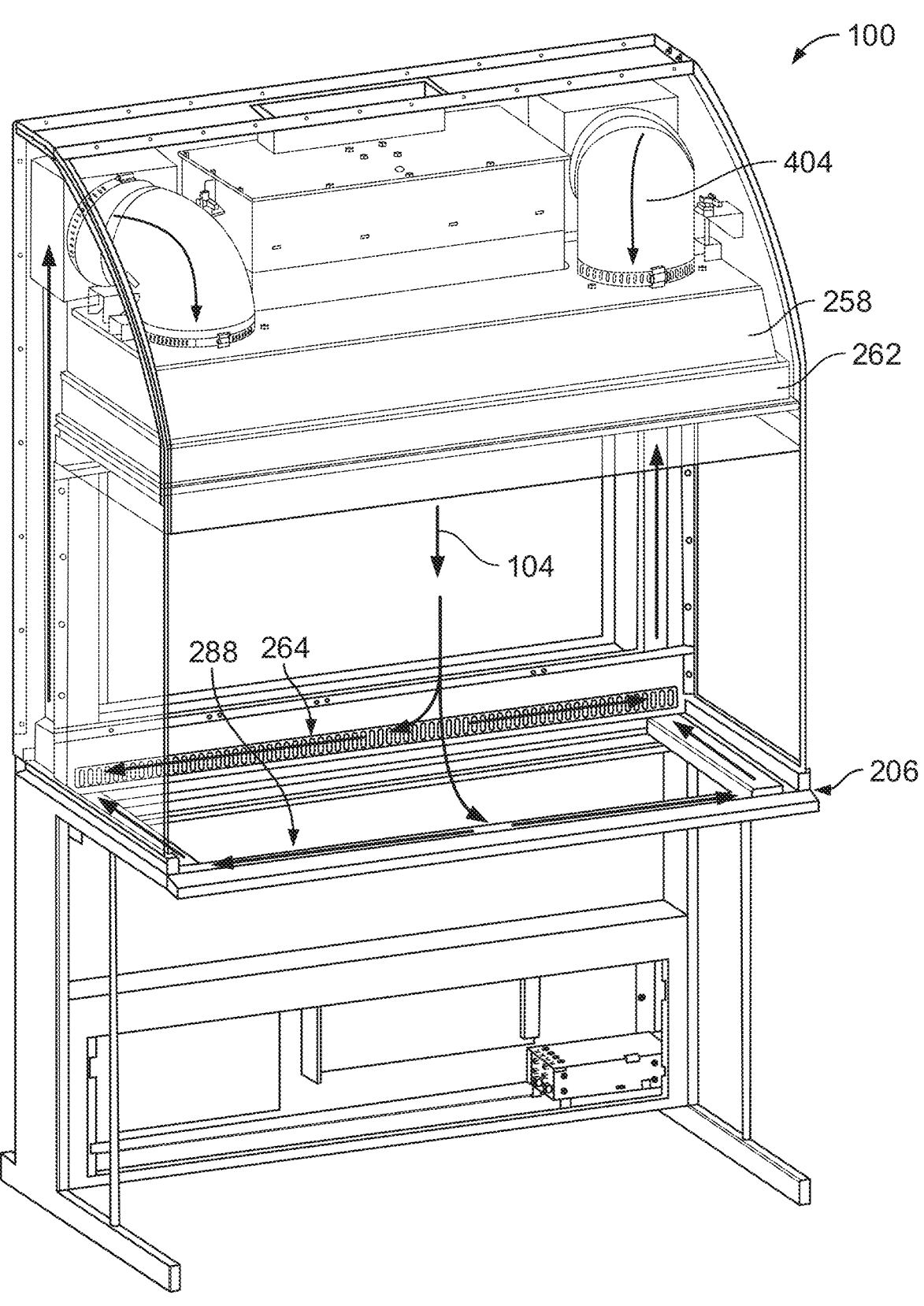

FIG. 14 illustrates an airflow path at the configurable workstation of FIG. 1 embodied as a Class II biosafety cabinet.

Figure 15:
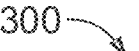
Figure 15:
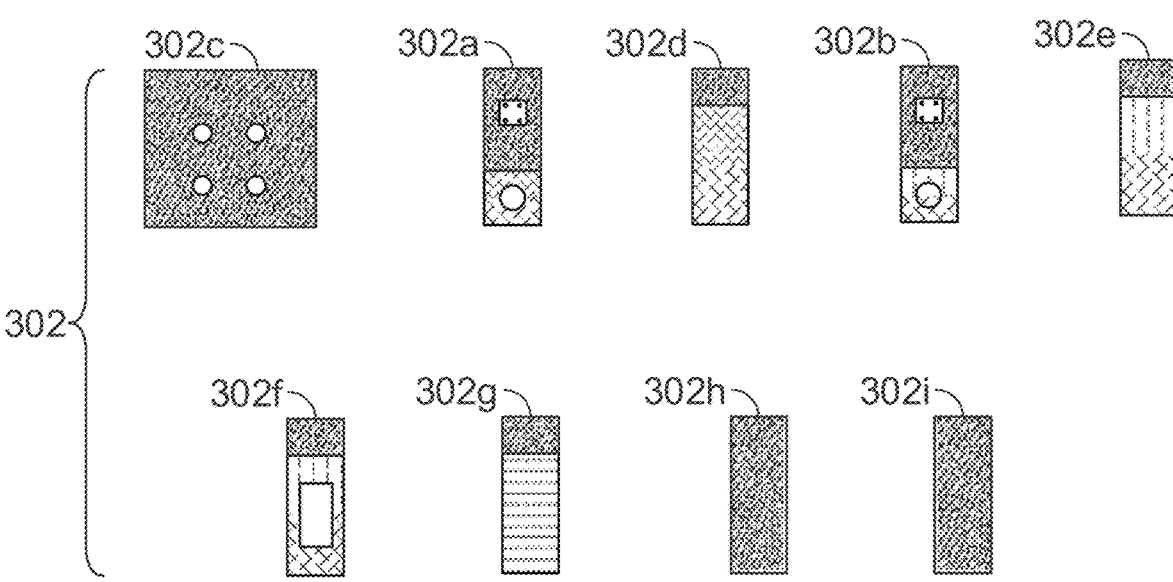
Figure 15:
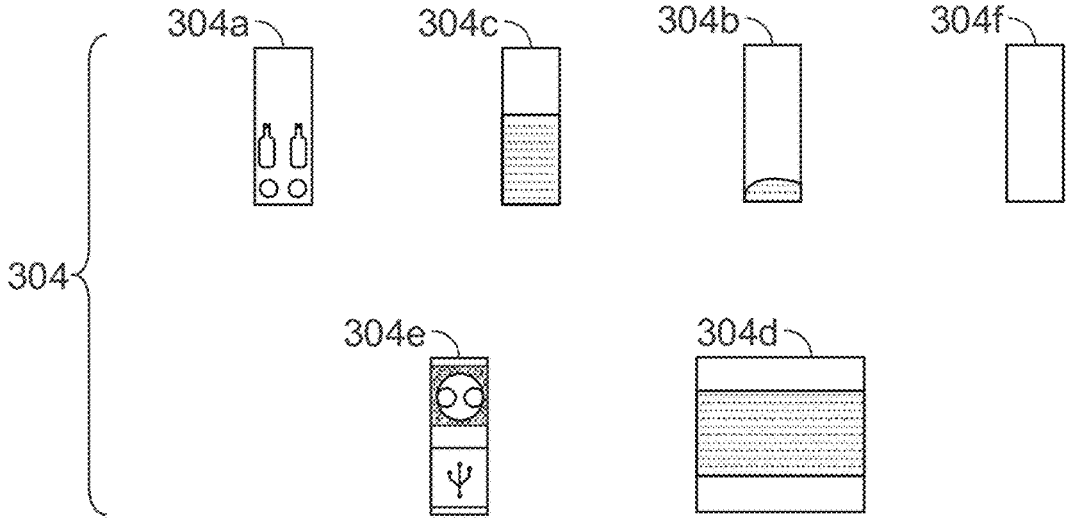

FIG. 15 is a schematic illustration of modules of the configurable workstation of FIG. 1.

Figure 16:
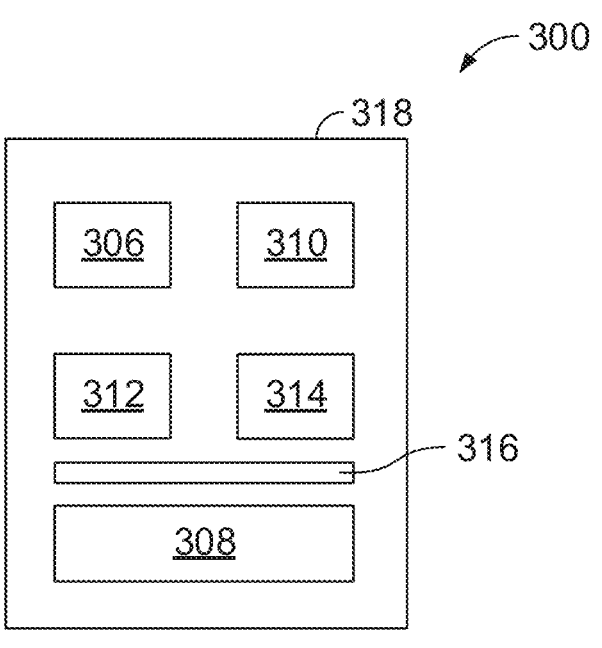

FIG. 16 is a schematic illustration of certain modules of FIG. 15.

Figure 9:
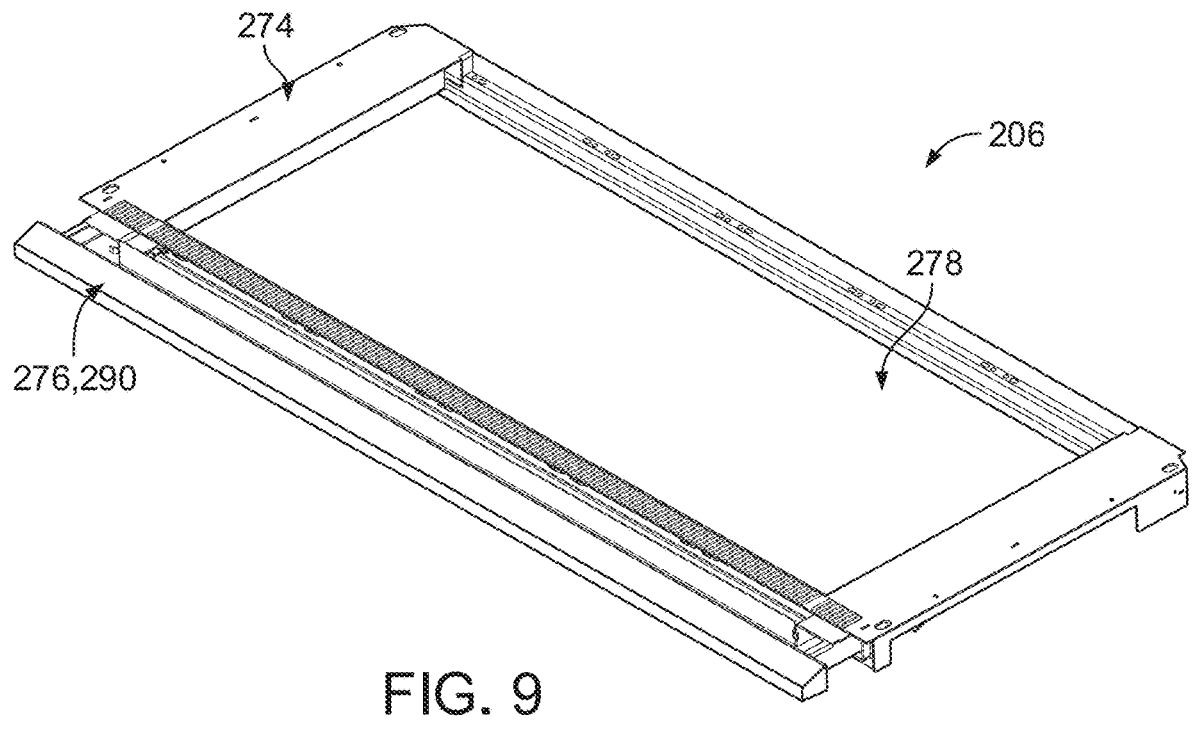
FIG. 9 is a perspective view of a table of the configurable workstation of FIG. 1.
Figure 17:
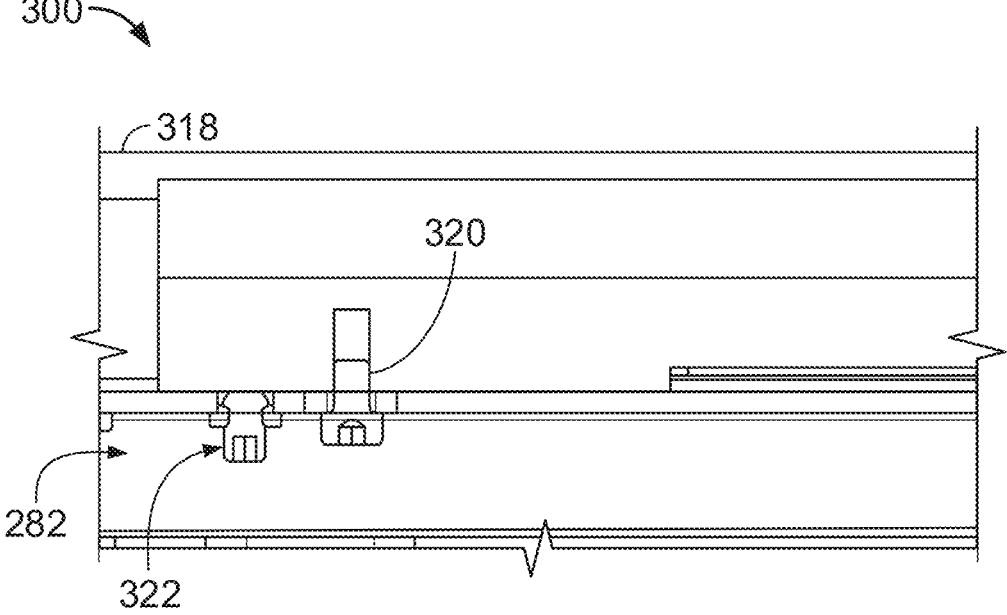

FIG. 17 is a cross-sectional schematic view of an interface between a module of FIG. 15 and the table of FIG. 9 with a push and pull fasteners.

Figure 18:
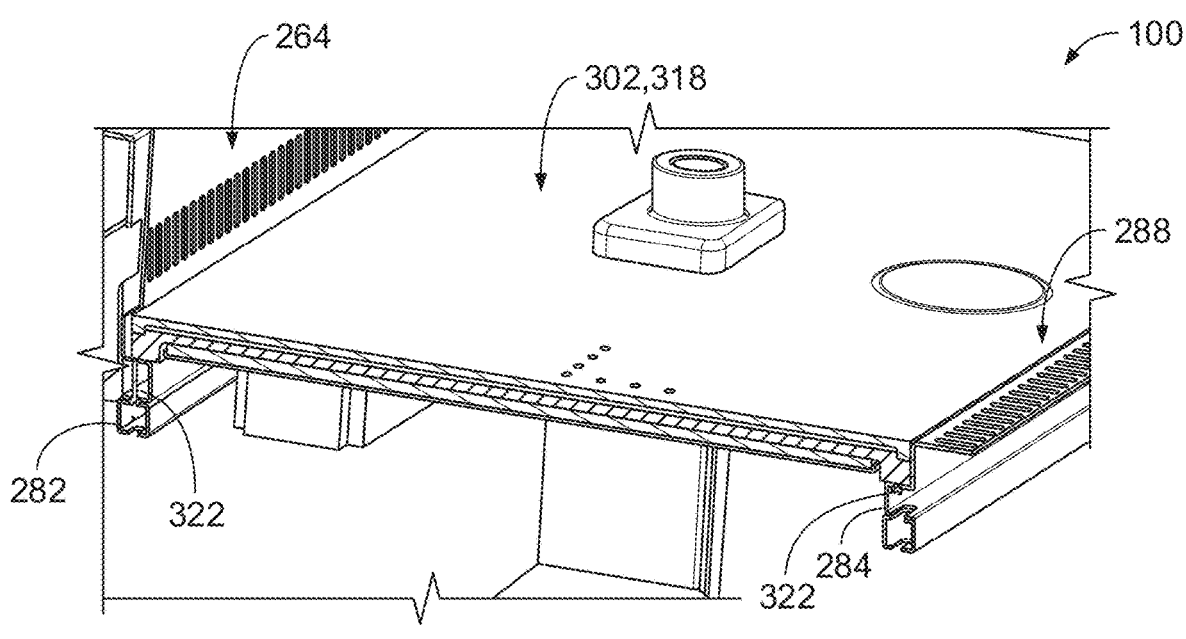

FIG. 18 is a cross-sectional view of an interface between a module of FIG. 15 and the table of FIG. 9 with the push fastener of FIG. 17.

Figure 19:
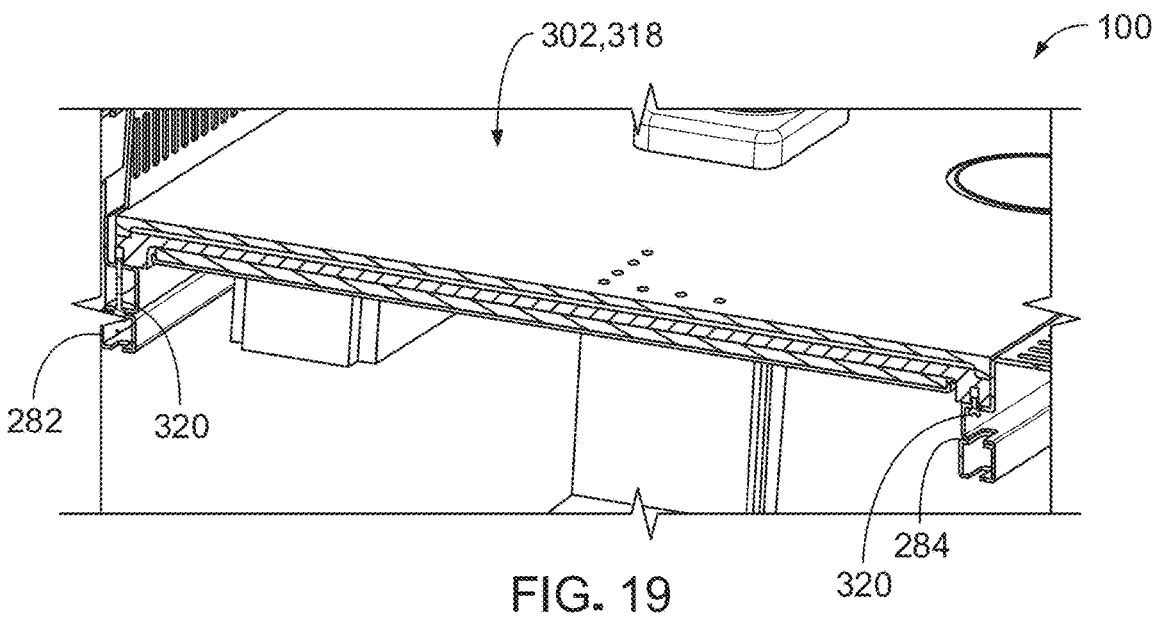

FIG. 19 is a cross-sectional view of an interface between a module of FIG. 15 and the table of FIG. 9 with the pull fastener of FIG. 17.

Figure 20:
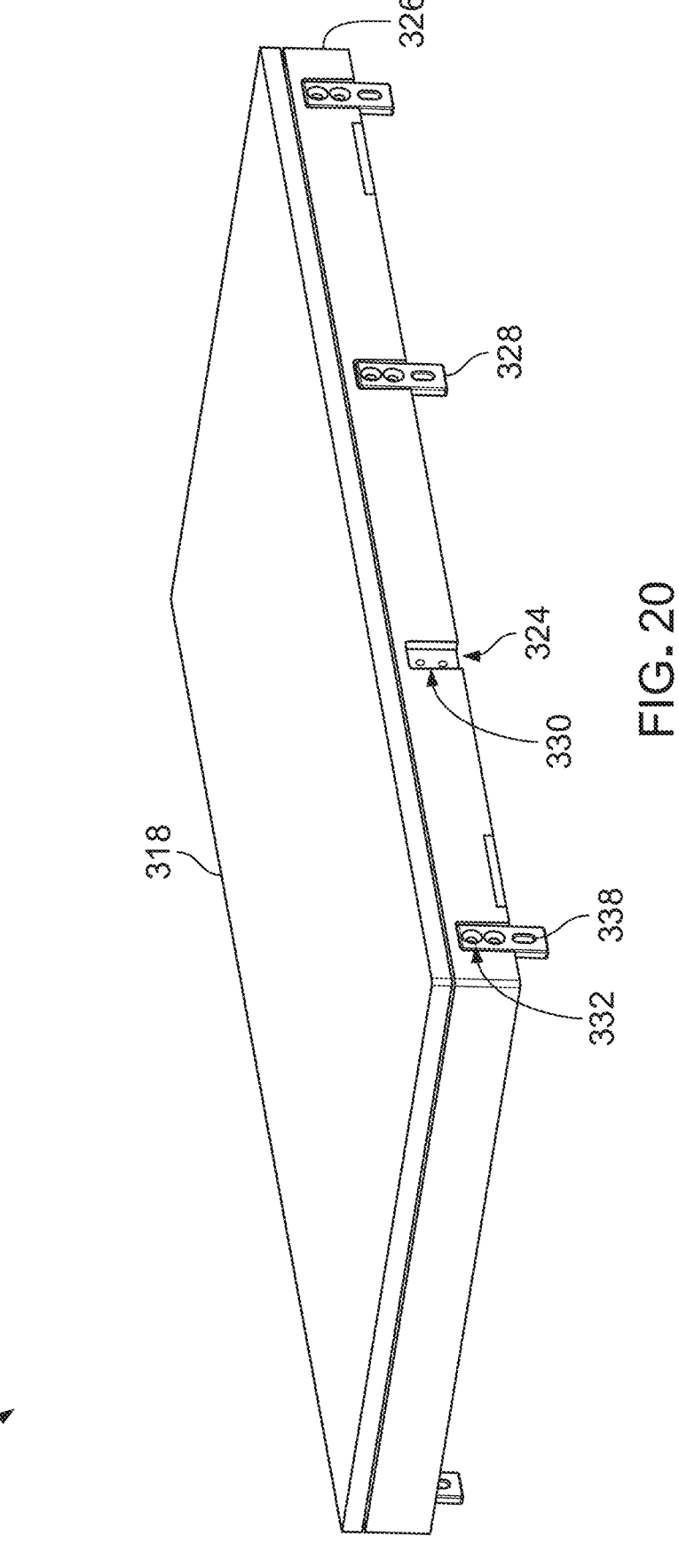

FIG. 20 is a perspective view of a module of FIG. 15 equipped with adjustment blocks.

Figures 21, 22:
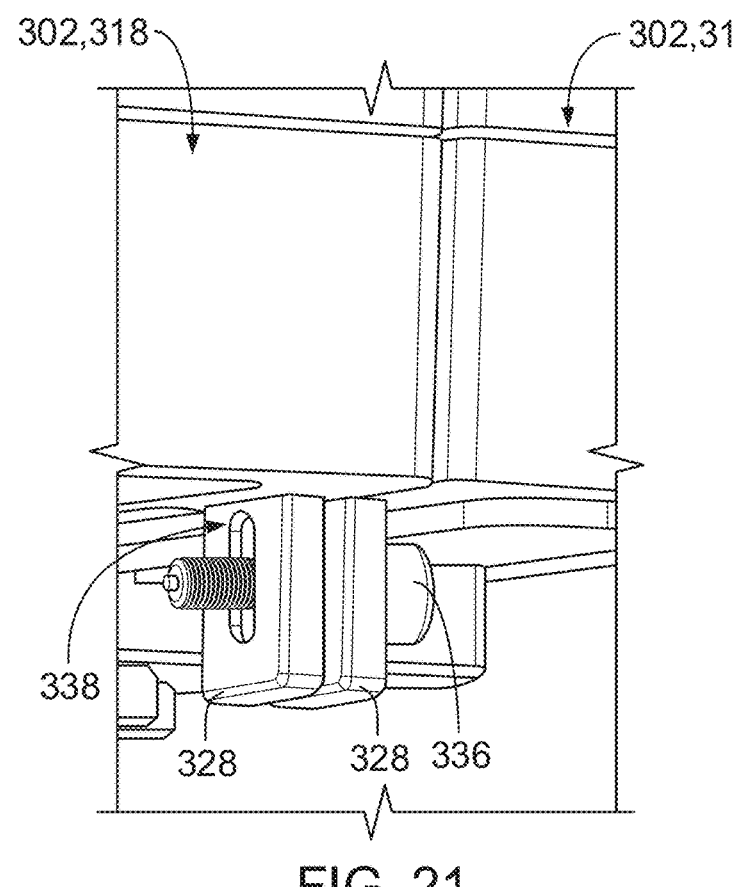

FIG. 21 is an enlarged perspective view of two modules of FIG. 15 connected to each other via two adjustment blocks of FIG. 20.

FIG. 22 is a bottom perspective view of an interface of two modules of FIG. 15 connected by an adjustment block.

Figure 23:
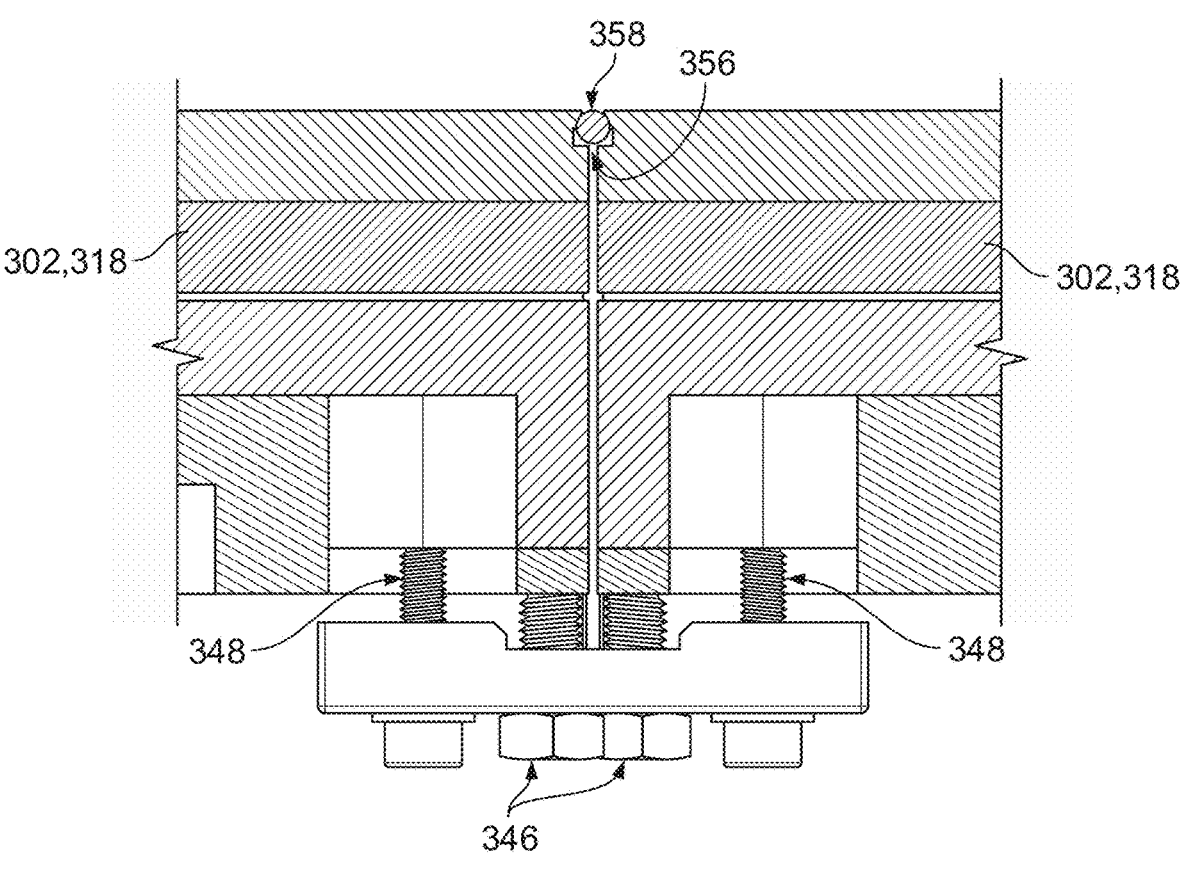

FIG. 23 is a side view of the interface of FIG. 22.

Figure 24:
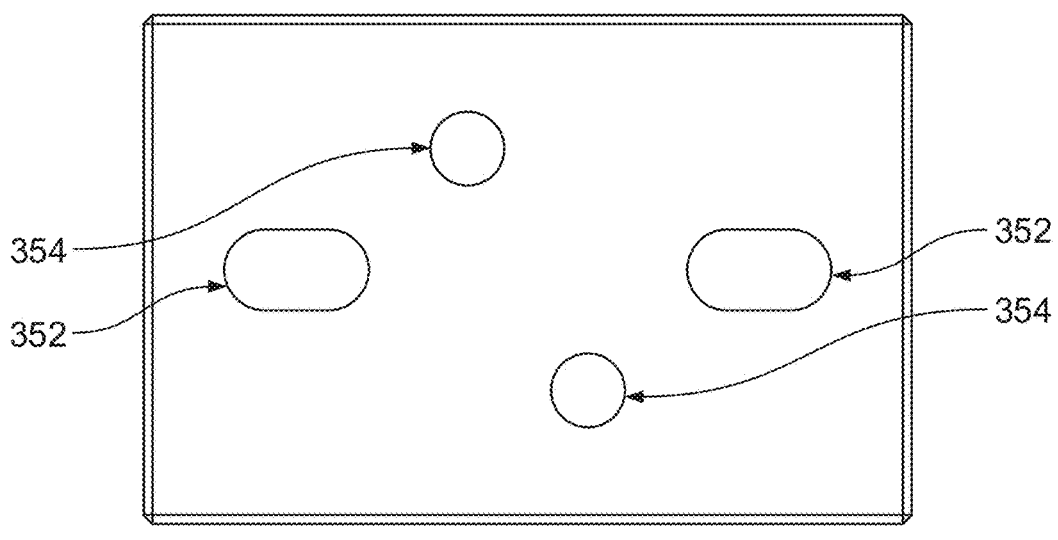

FIG. 24 is a top view of the adjustment block of FIG. 22.

Figure 25:
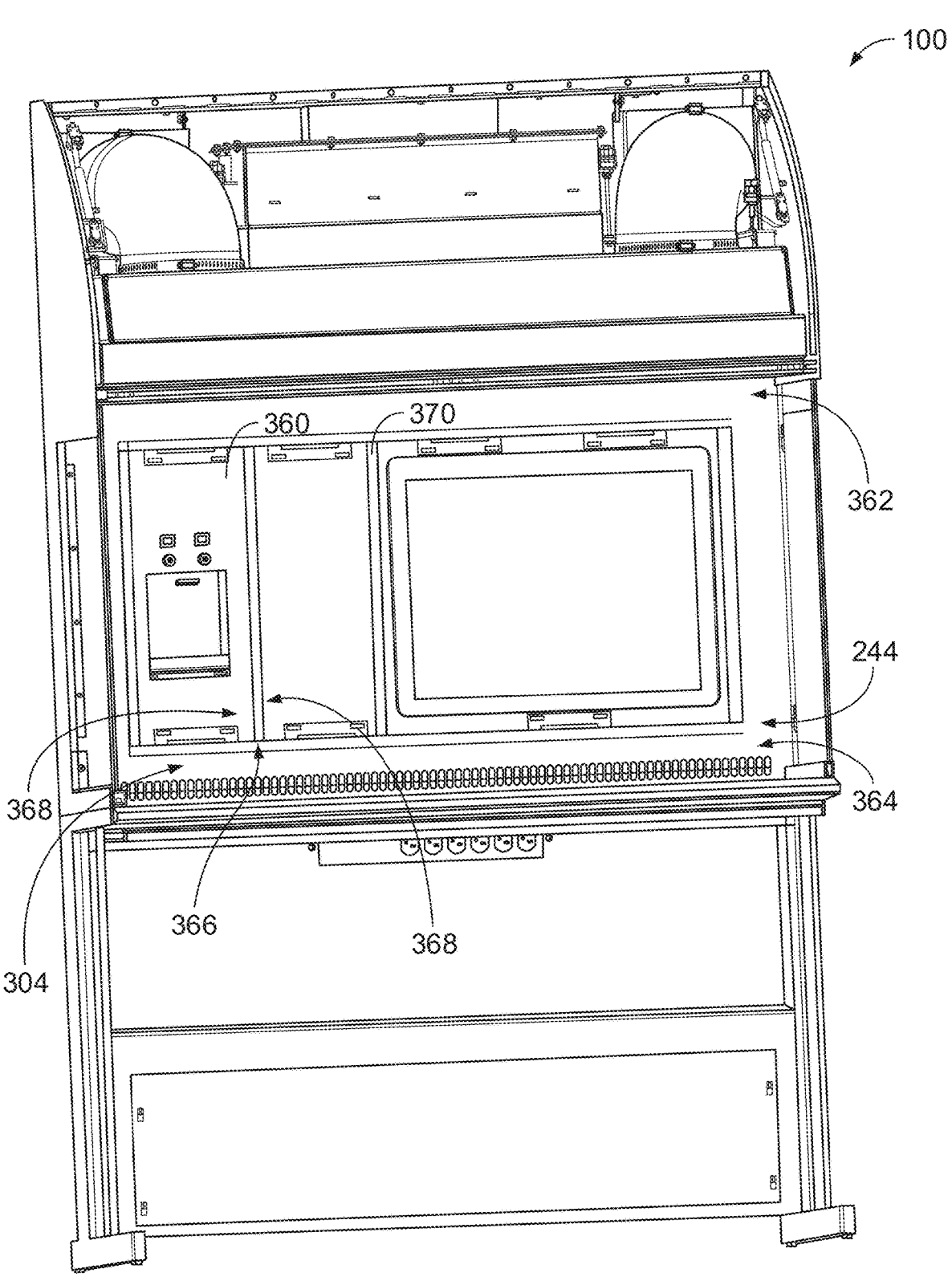

FIG. 25 is a front perspective view of wall modules of FIG. 15 installed to a front panel of the configurable workstation of FIG. 1.

Figures 26, 27:
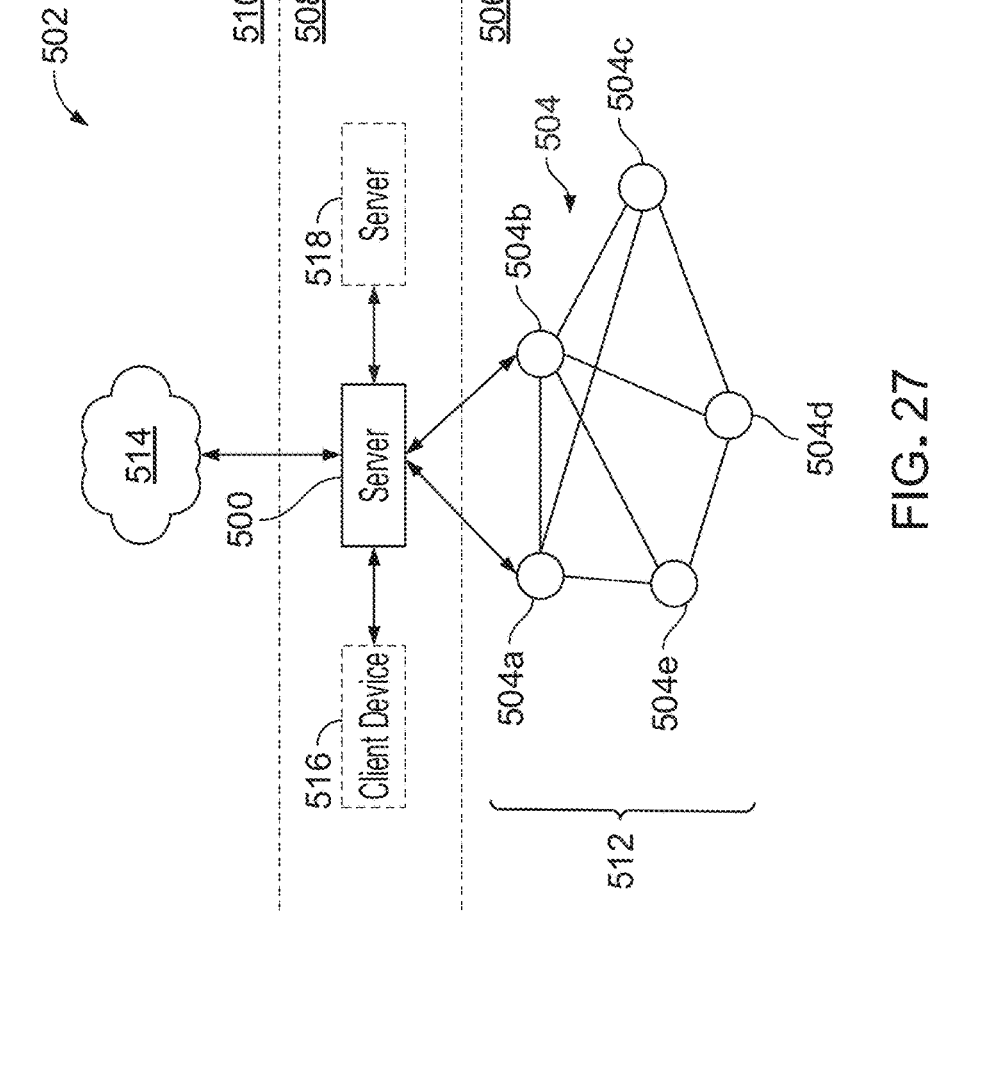

FIG. 26 is a perspective view of a gasket that is installable between adjacent wall modules of FIG. 25.

FIG. 27 is a schematic diagram of a network communication architecture 502 on which the configurable workstation of FIG. 1 operates.

Figure 28:
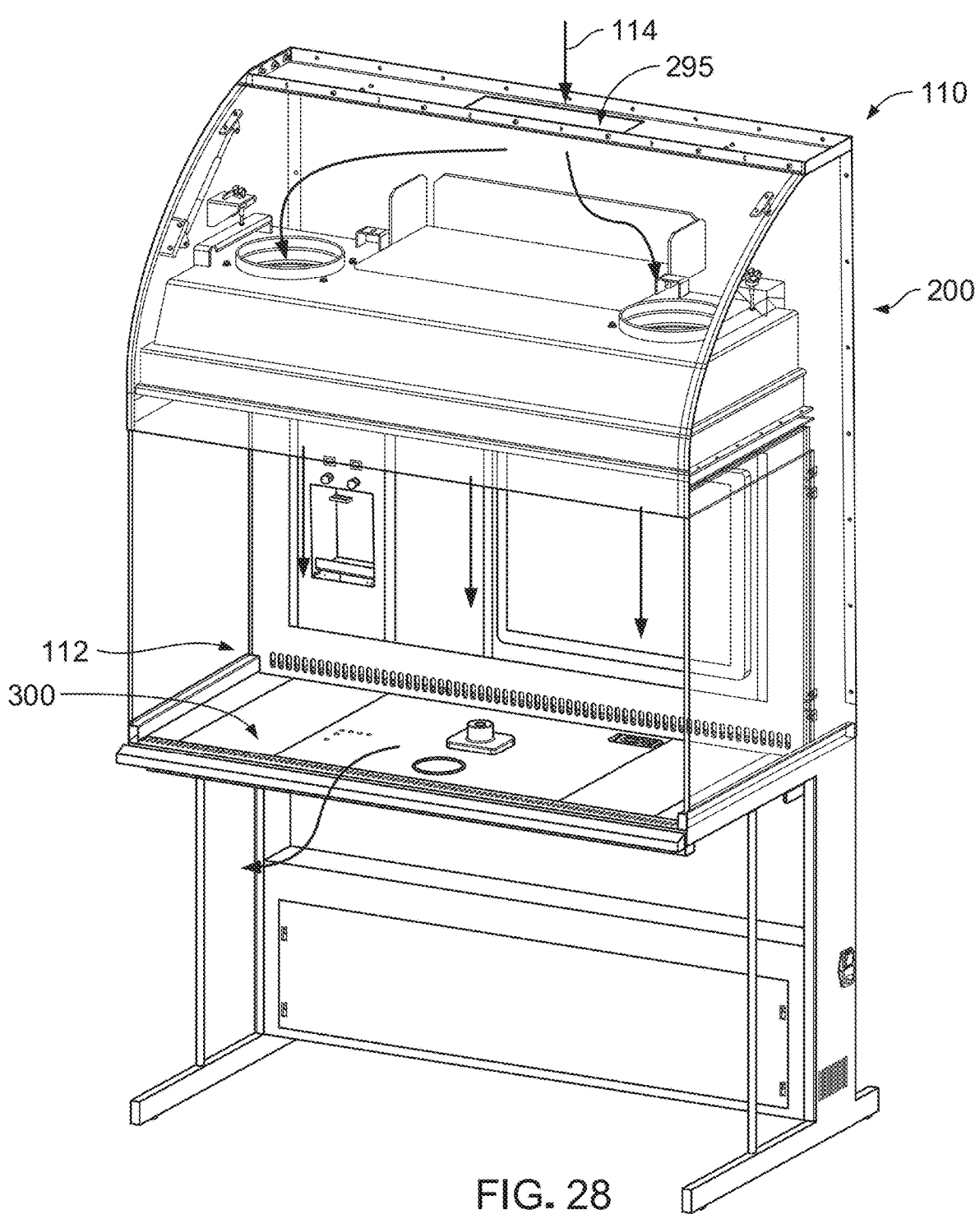

FIG. 28 illustrates an airflow path at a configurable workstation embodied as a Class I laminar flow cabinet.

Figure 29:
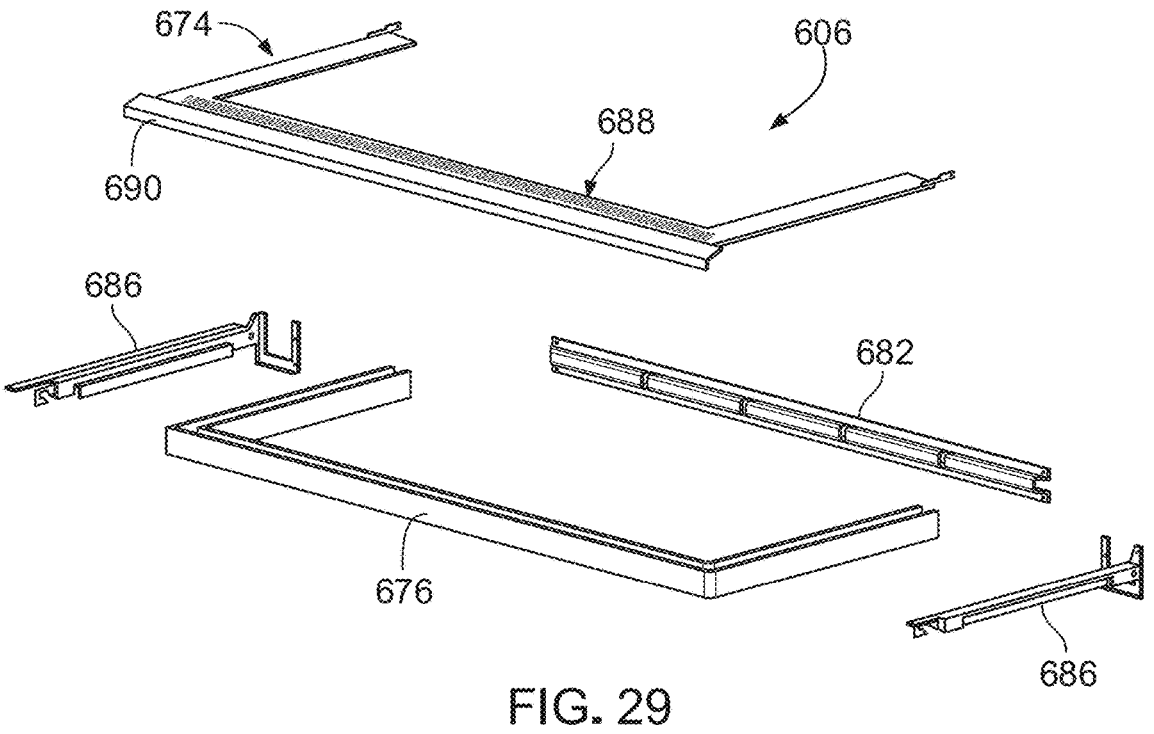

FIG. 29 is an exploded perspective view of a flip-top table that can be installed to a frame of the configurable workstation of FIG. 1.

Figure 30:
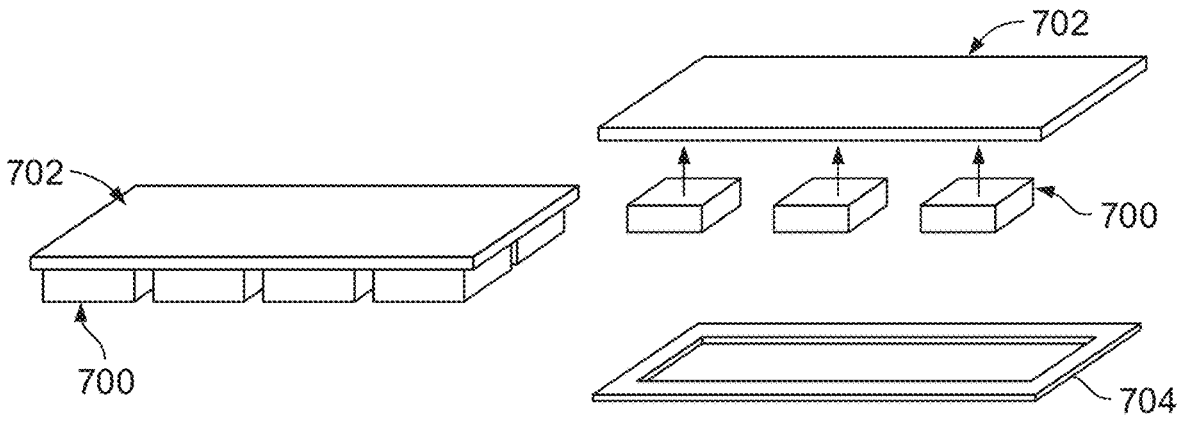

FIG. 30 is a perspective view of module leveling and gap sealing using a protector film.

FIG. 31 is a perspective view of module leveling using spring-like components that push a module up against multiple level rails.

FIG. 32 is a side view of magnets used to pull two modules toward each other for gap minimization.

FIG. 33 is a side view of a cam lock screw mechanism used to pull two modules toward each other for gap minimization.

Figure 34:
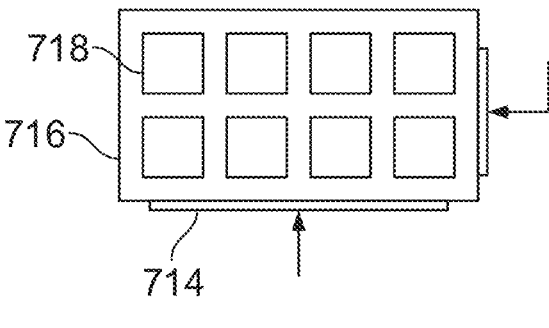

FIG. 34 is a top view of a workstation frame designed to apply lateral pressure to a table at which modules are installed to minimize gaps between the modules.

Figure 35:
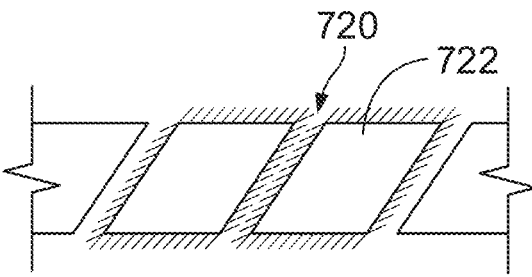

FIG. 35 is a perspective view of liquid gasket applied between modules to fill gaps between the modules.

Figure 36:
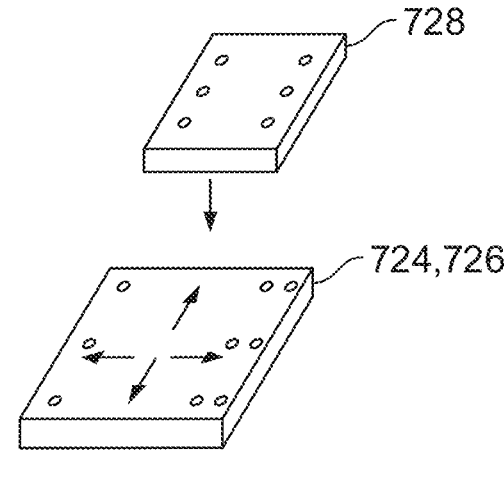

FIG. 36 is an exploded perspective view of a module that can be compressed with an accessory tool to expand laterally toward adjacent modules to minimize gaps therebetween.

Figure 37:
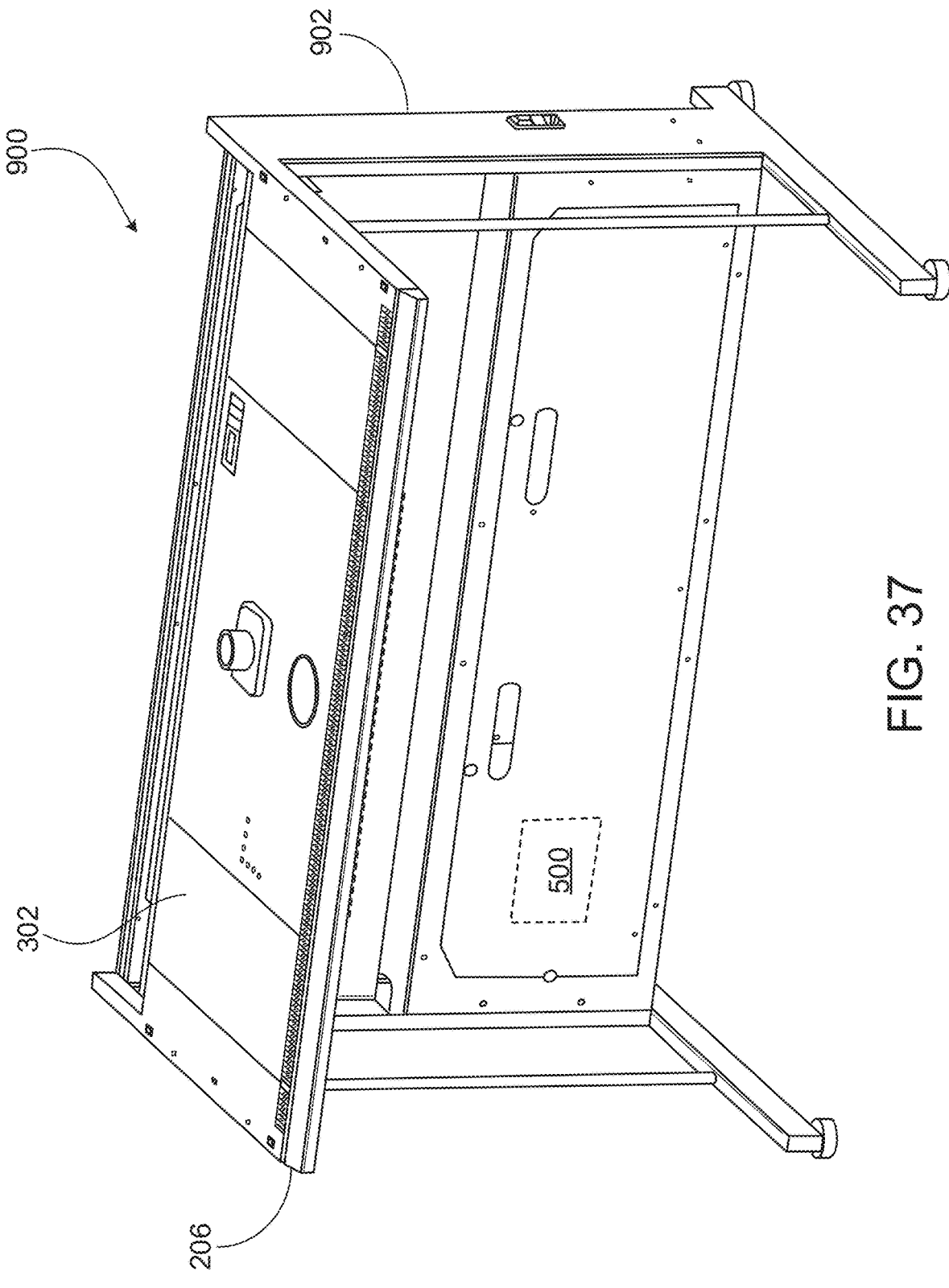

FIG. 37 is a perspective view of a configurable workstation embodied as a no-hood frame.

Figure 38:
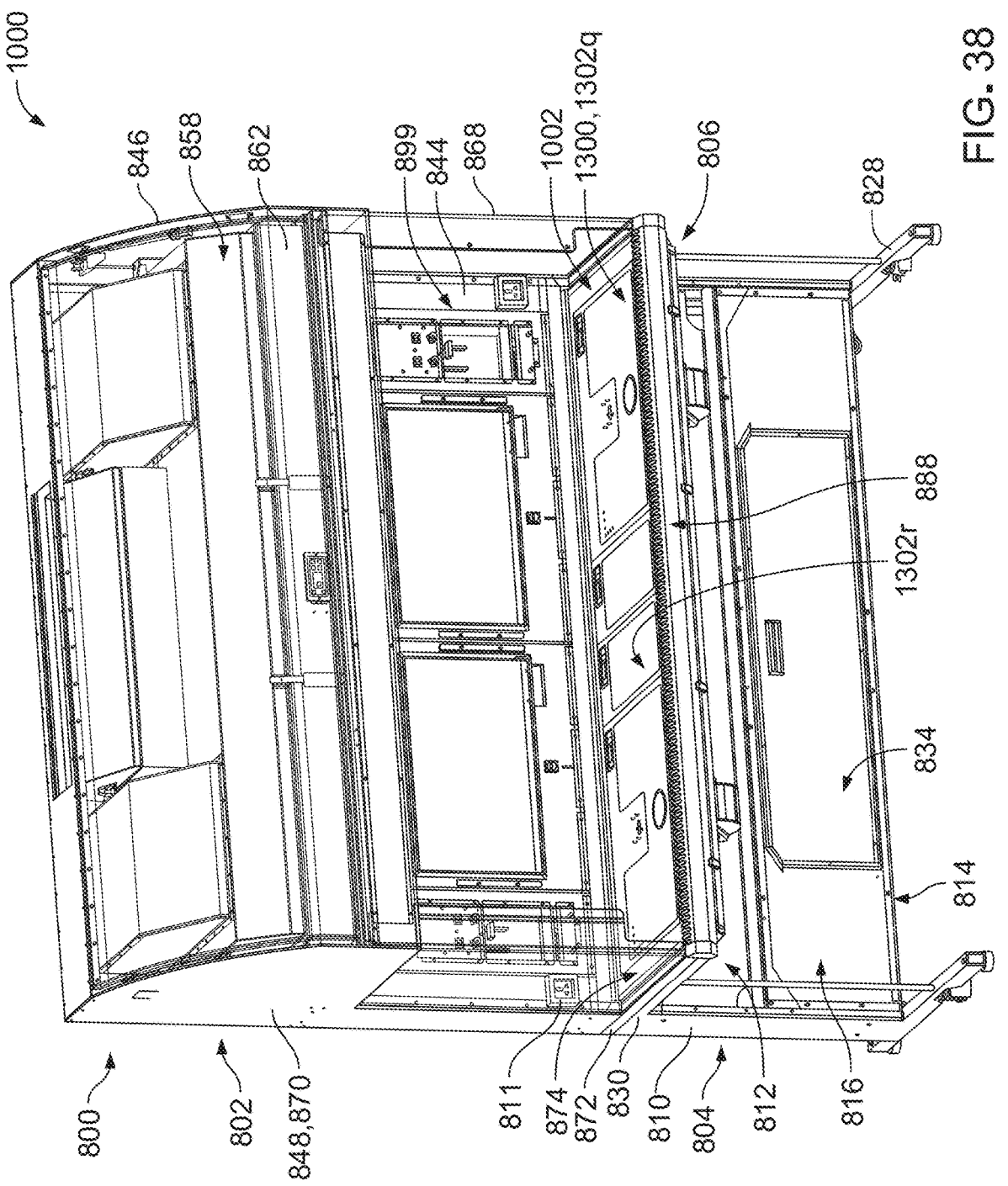

FIG. 38 is a front perspective view of a configurable workstation.

Figure 39:
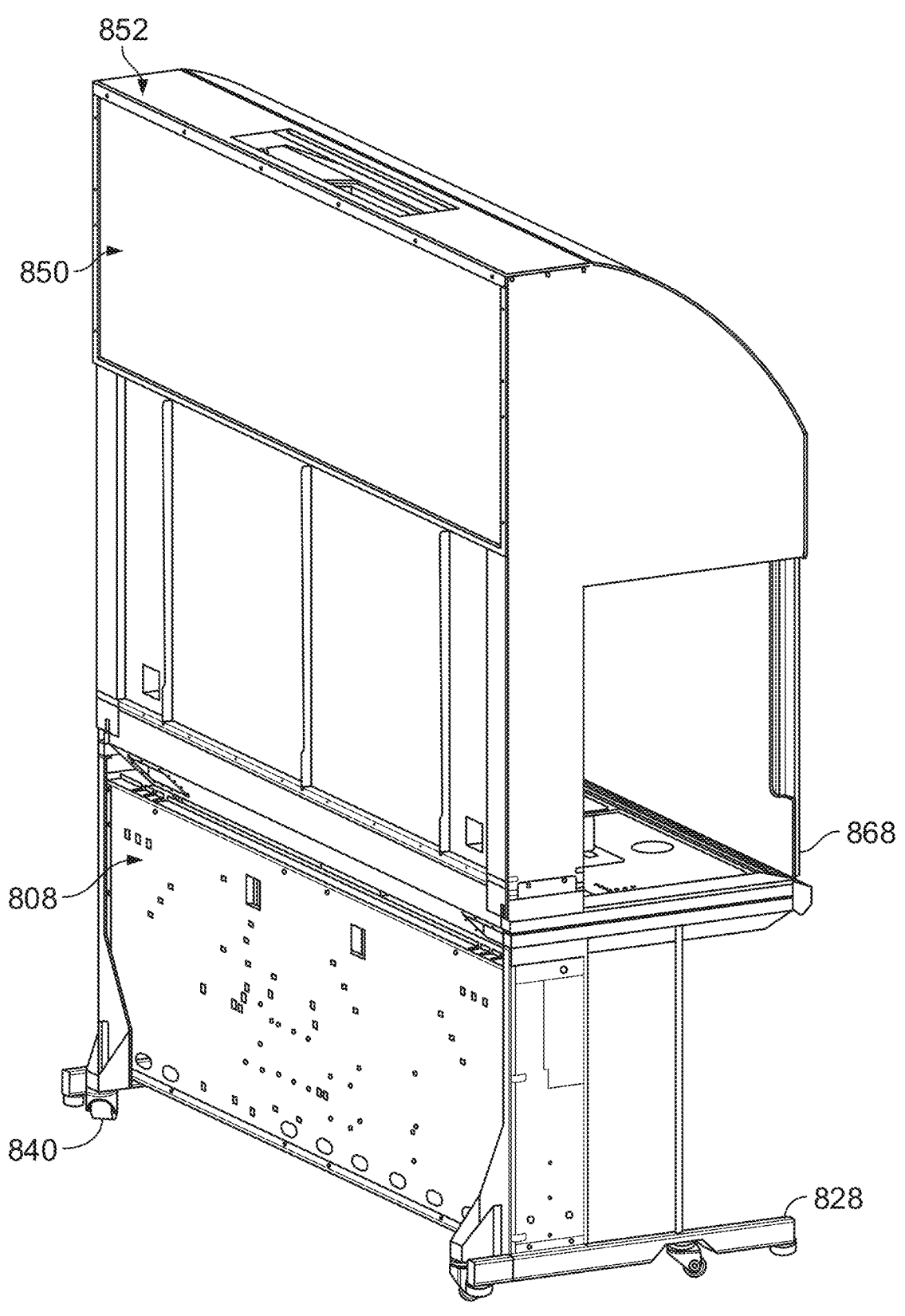

FIG. 39 is a rear perspective view of the configurable workstation of FIG. 38.

Figure 40:
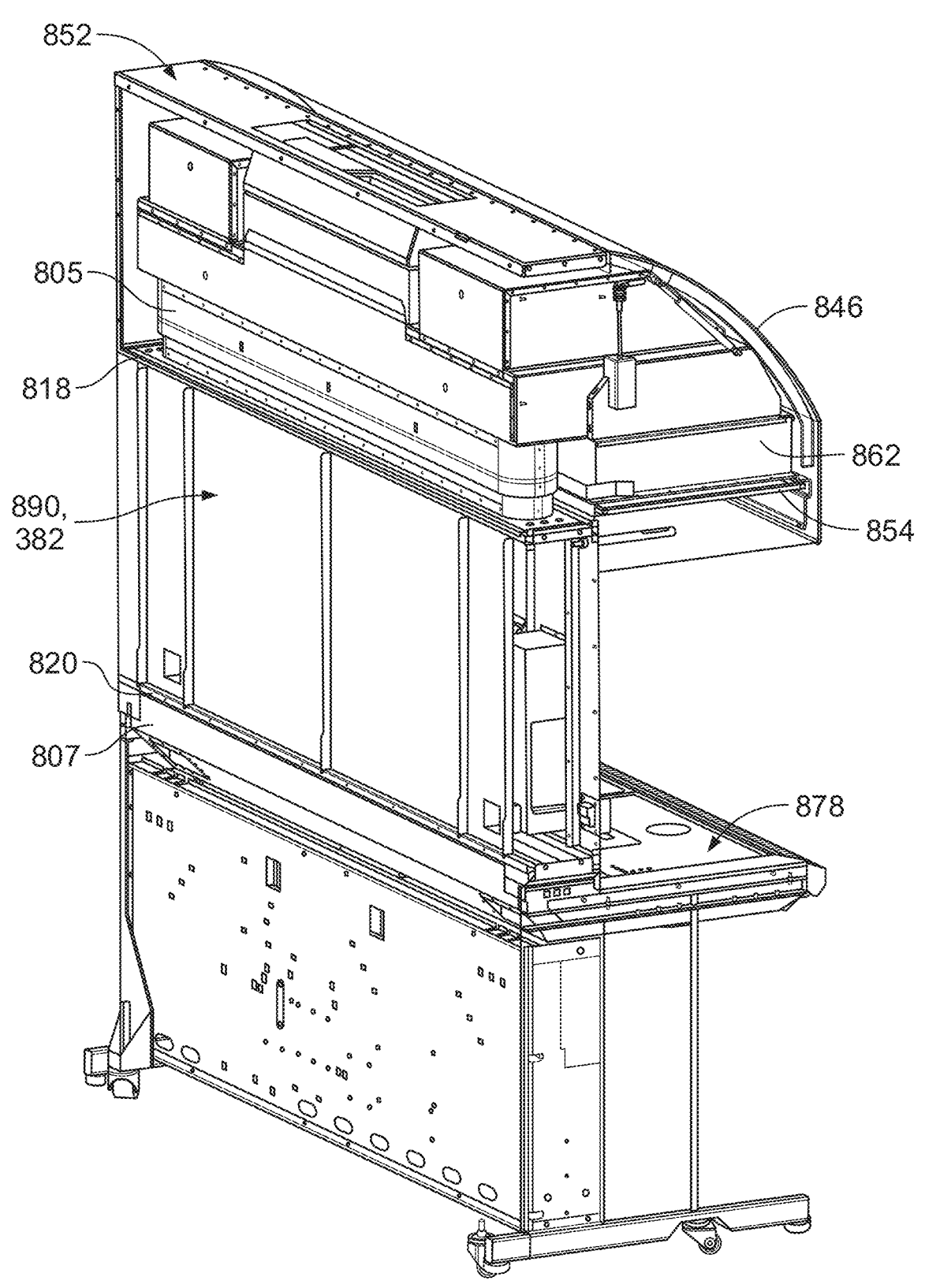

FIG. 40 is a rear perspective view of the configurable workstation of FIG. 38, with certain frame panels removed to expose internal components.

Figure 41:
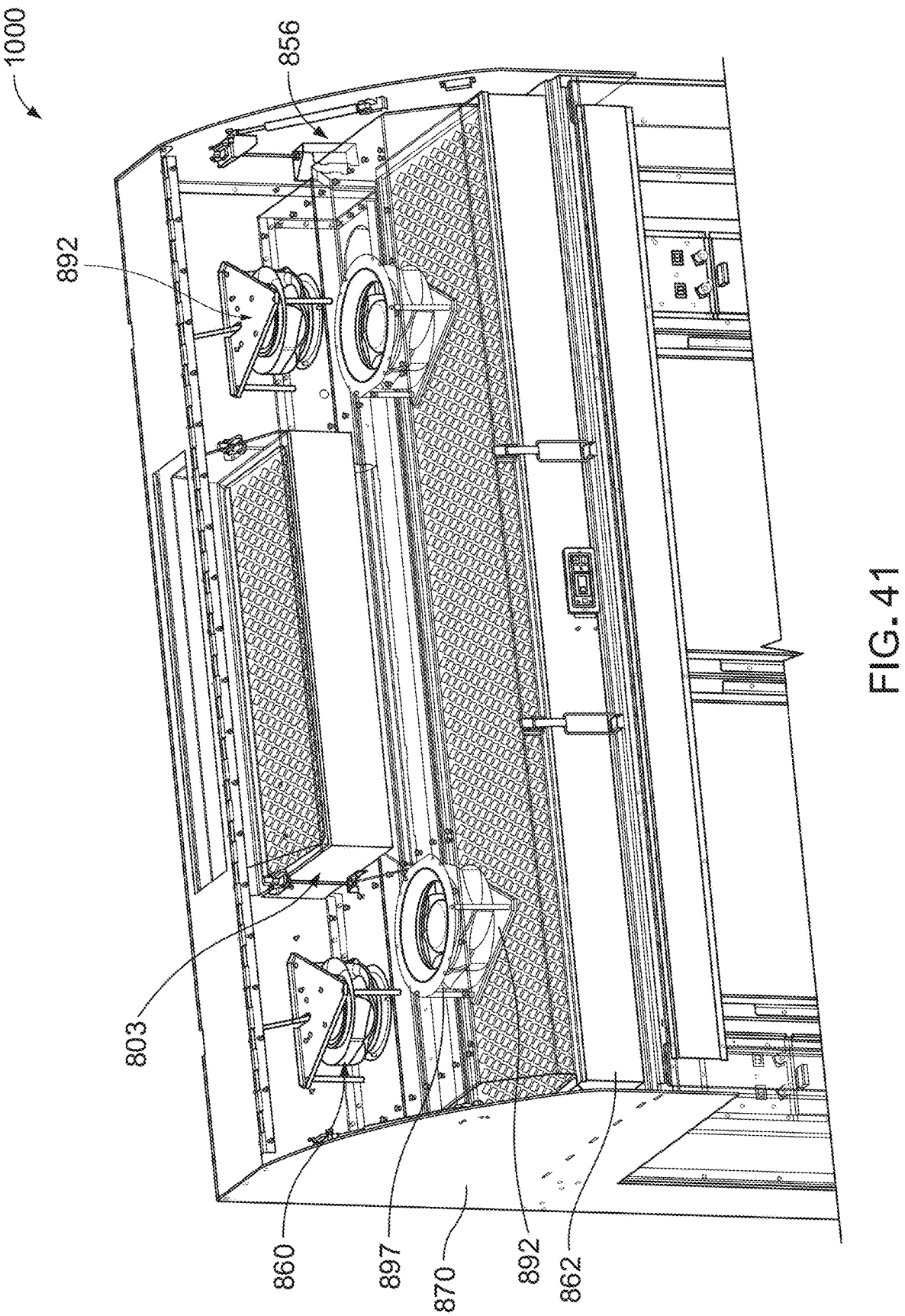

FIG. 41 is an enlarged perspective view of an airflow enclosure of the configurable workstation of FIG. 38.

Figure 42:
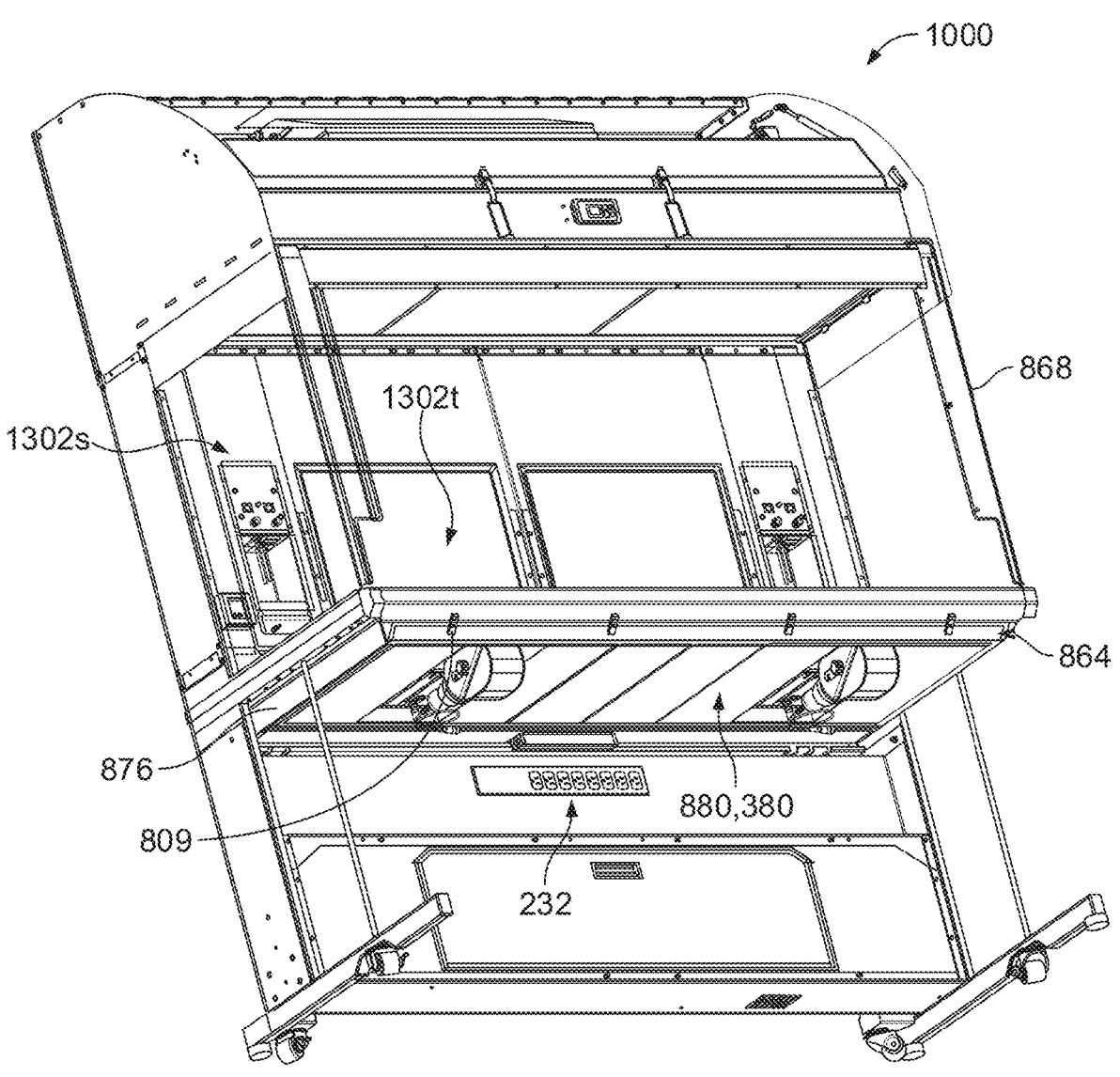

FIG. 42 is a bottom perspective view of the configurable workstation of FIG. 38.

Figure 43:
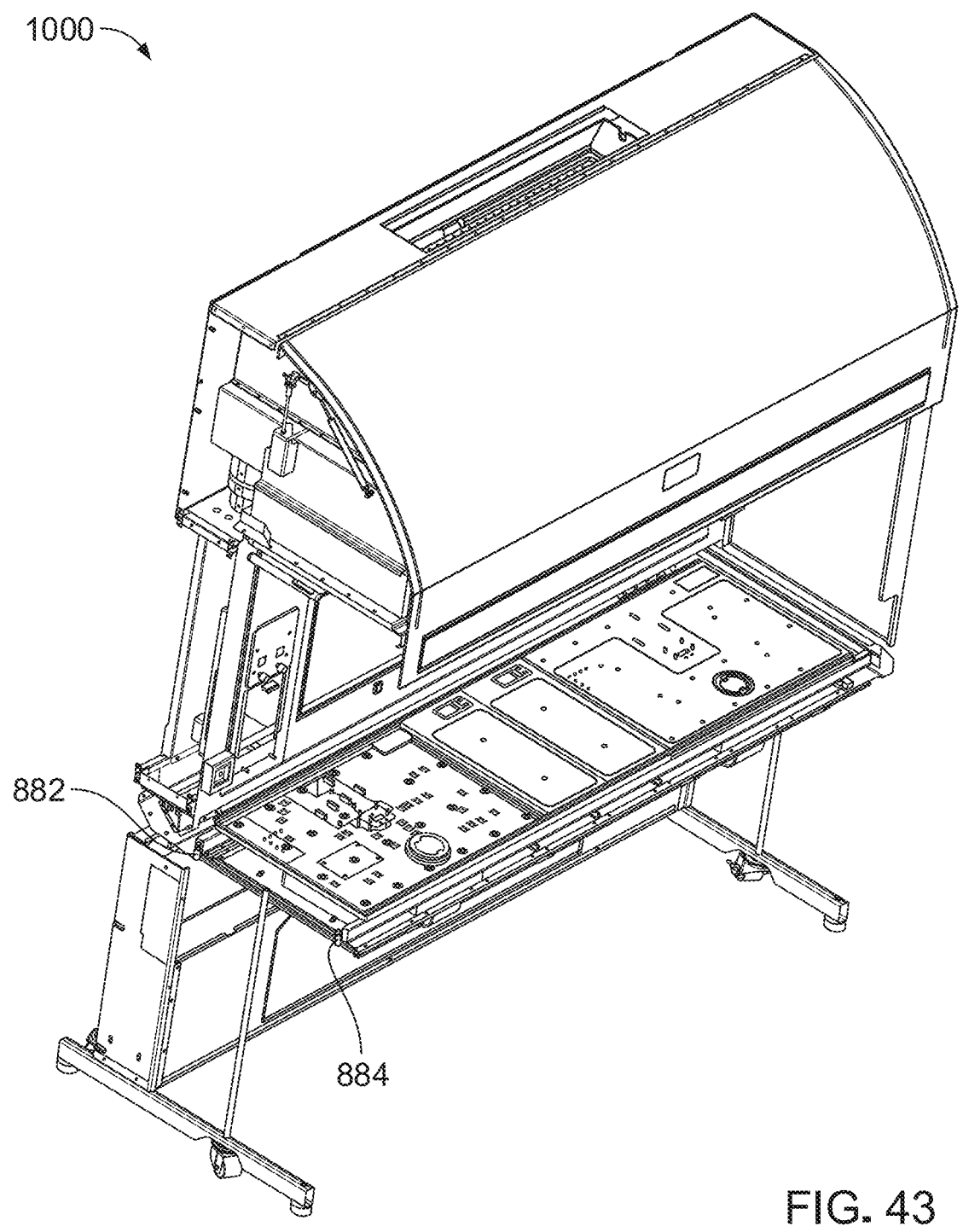

FIG. 43 is a top perspective view of the configurable workstation of FIG. 28, with certain frame panels removed to expose internal components.

Figure 44:
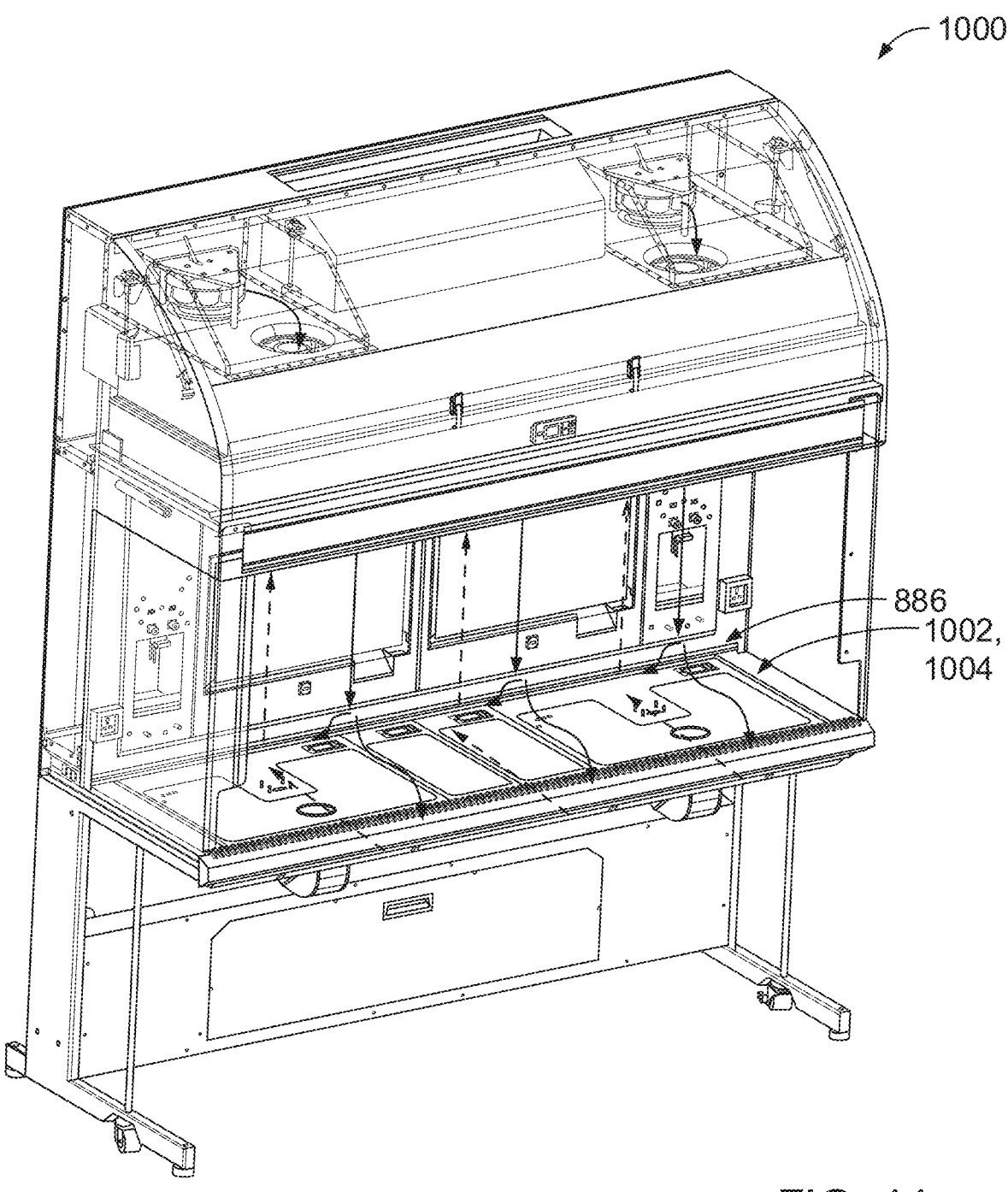

FIG. 44 illustrates an airflow path at the configurable workstation of FIG. 38 from a front perspective.

Figure 45:
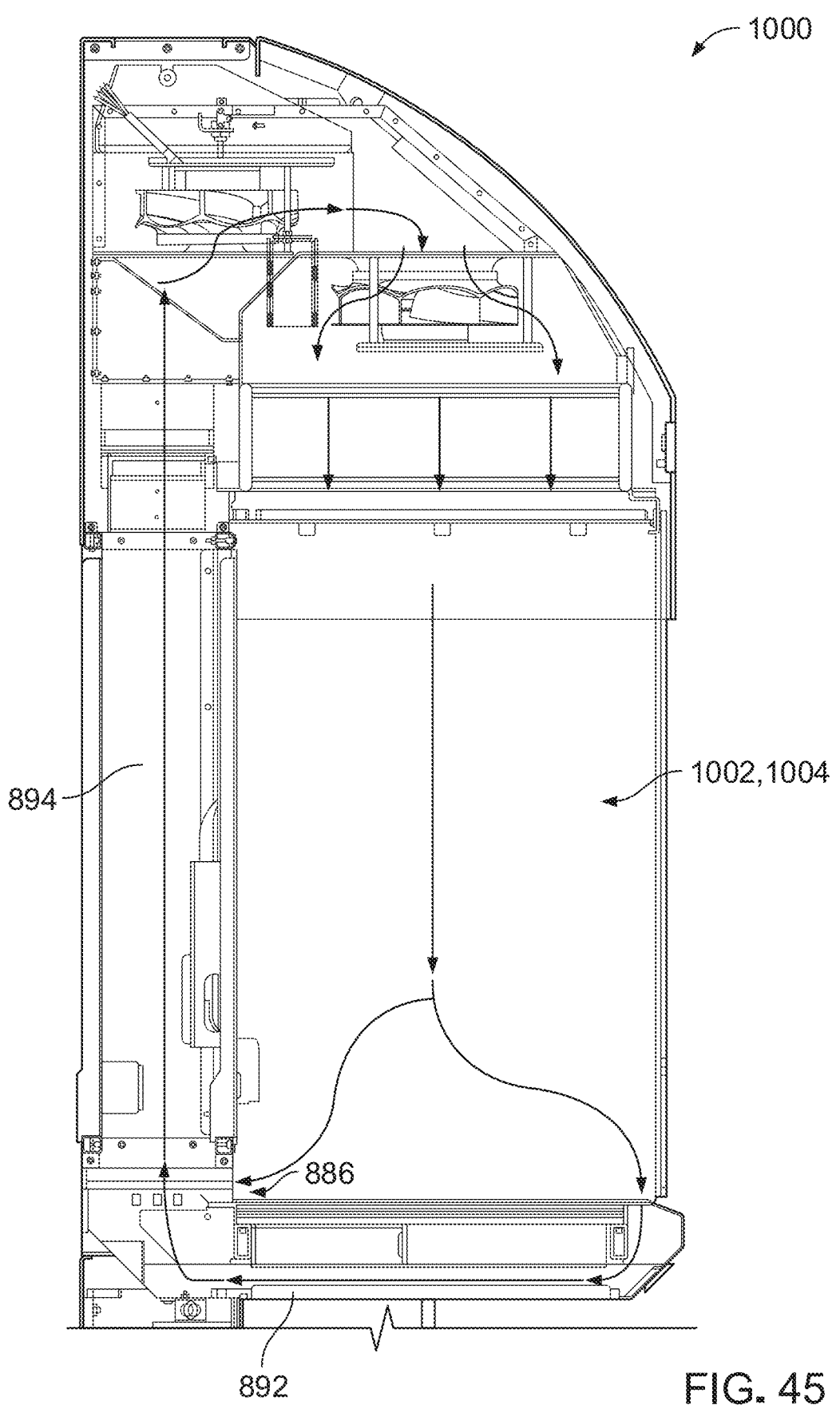

FIG. 45 illustrates an airflow path at the configurable workstation of FIG. 38 from a side view.

Figure 46:
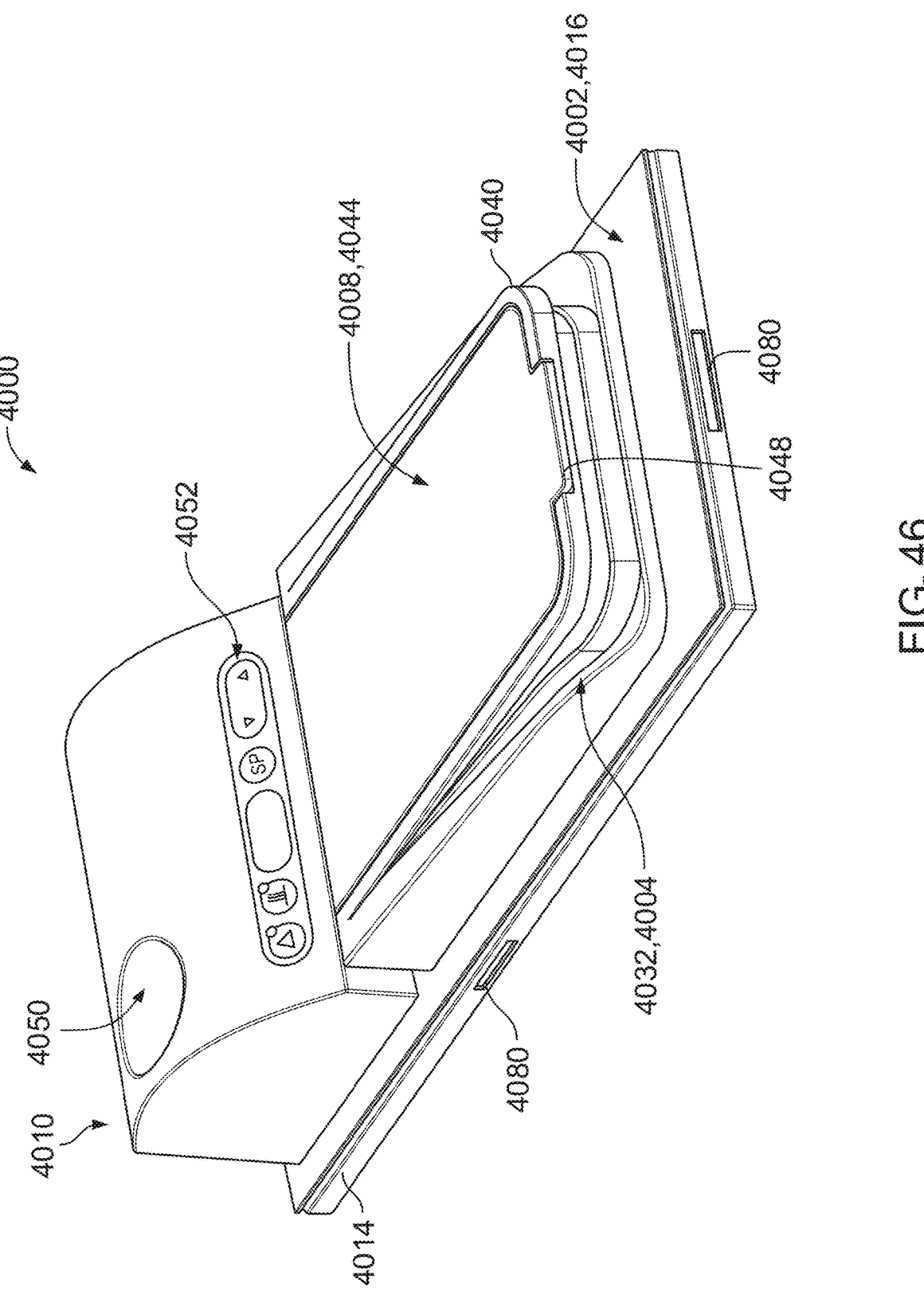

FIG. 46 is a perspective view of a modular incubator that is installable to any of the configurable workstations of FIGS. 1, 28, 37, and 38.

Figure 47:
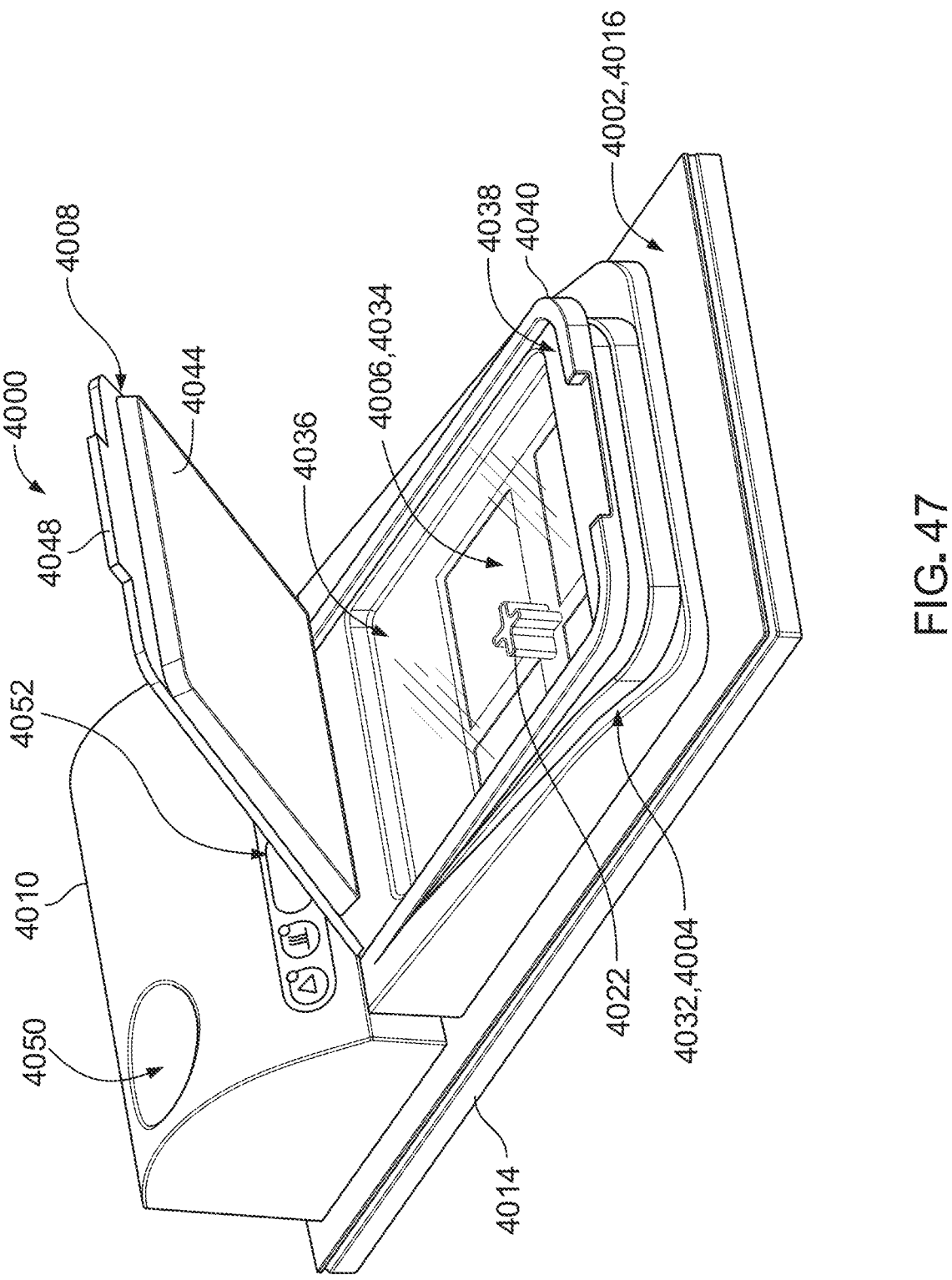

FIG. 47 is a perspective view of the modular incubator of FIG. 46 with a secondary lid of the incubator module opened from a primary lid of the incubator module.

Figure 48:
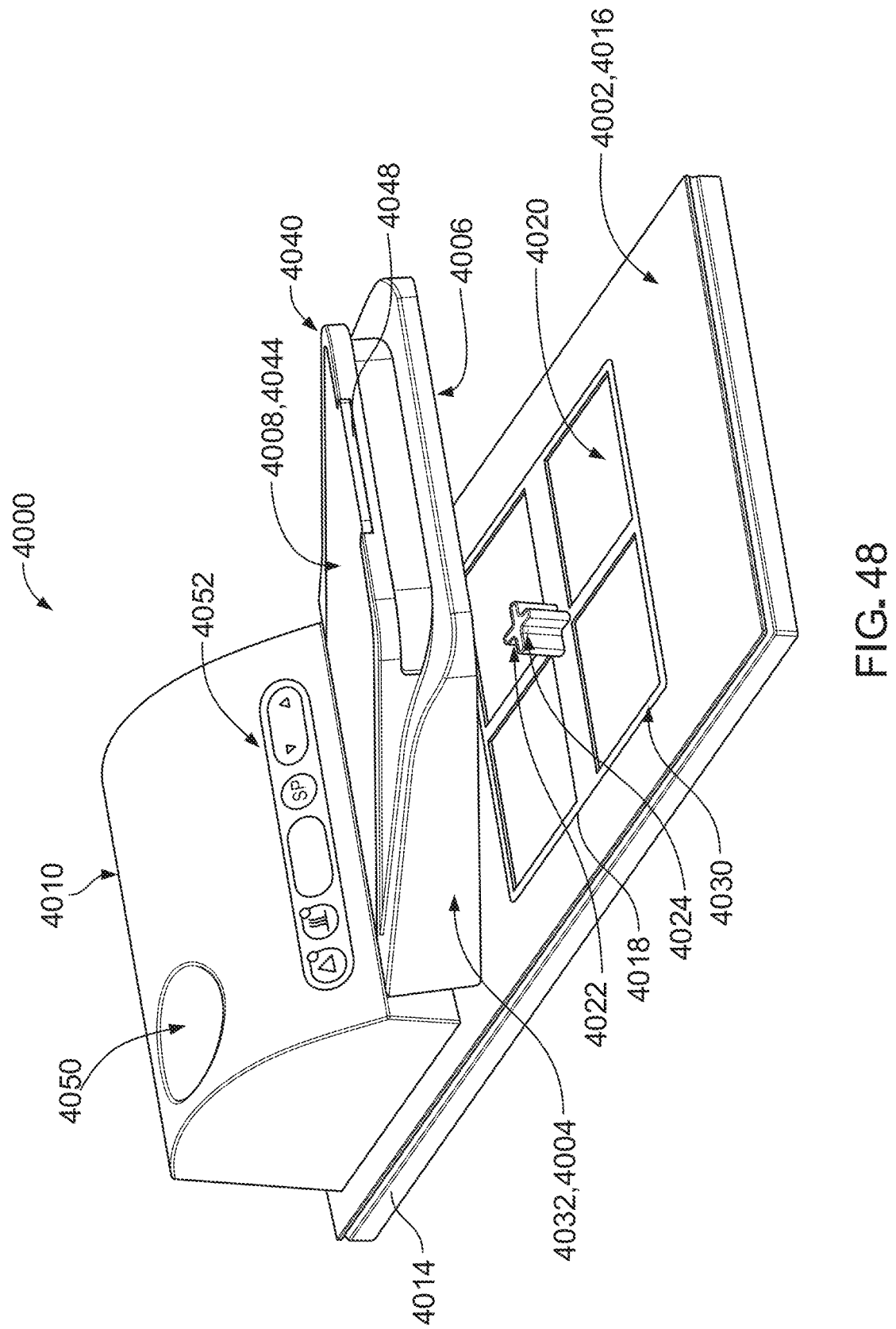

FIG. 48 is a perspective view of the modular incubator of FIG. 46 with the primary and secondary lids together opened from a platform of the incubator module.

Figure 49:
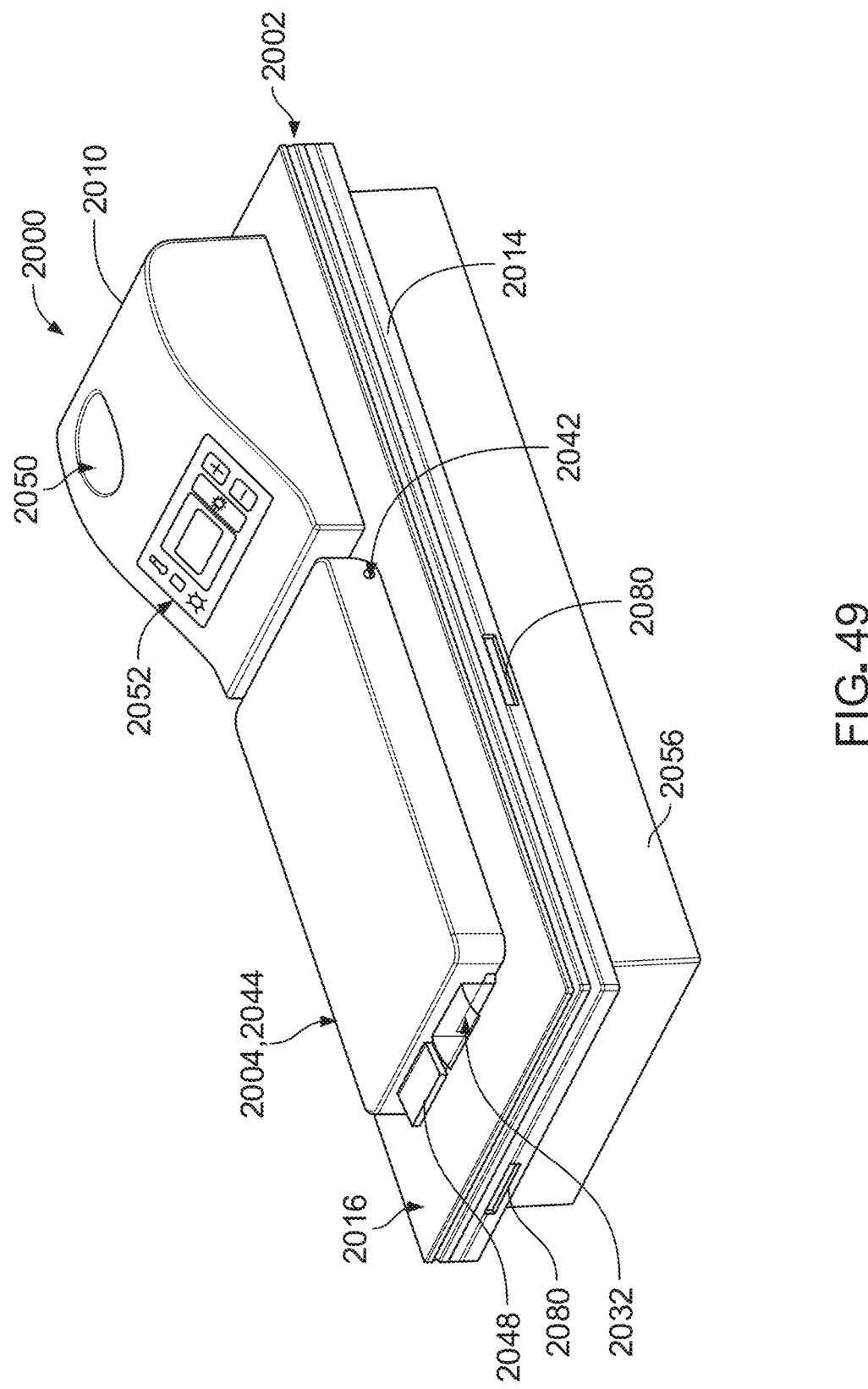

FIG. 49 is a perspective view of a modular incubator that is installable to any of the configurable workstations of FIGS. 1, 28, 37, and 38.

Figure 50:
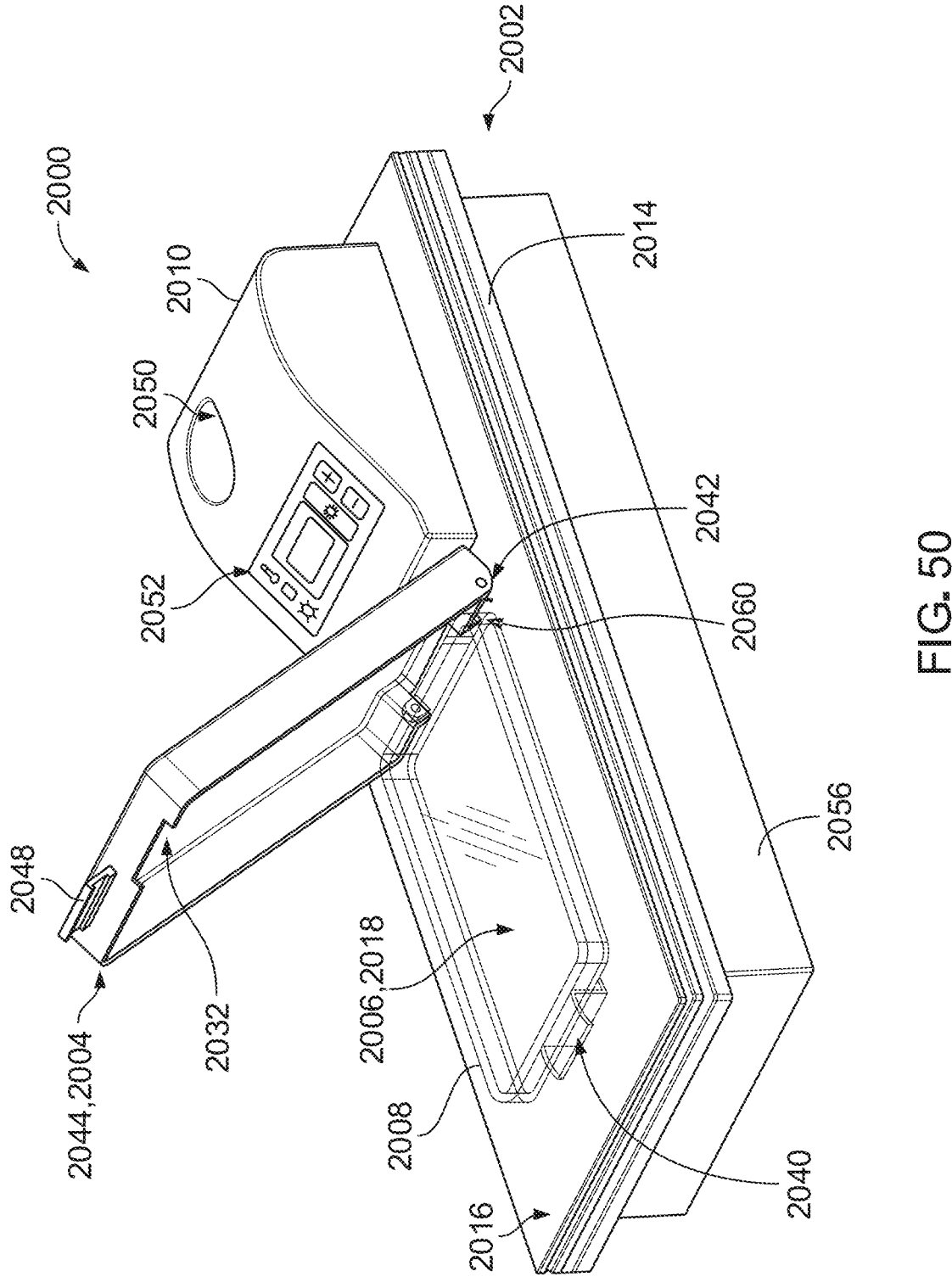

FIG. 50 is a perspective view of the modular incubator of FIG. 49 with an outer lid of the incubator module opened from a chamber wall of the incubator module.

Figure 51:
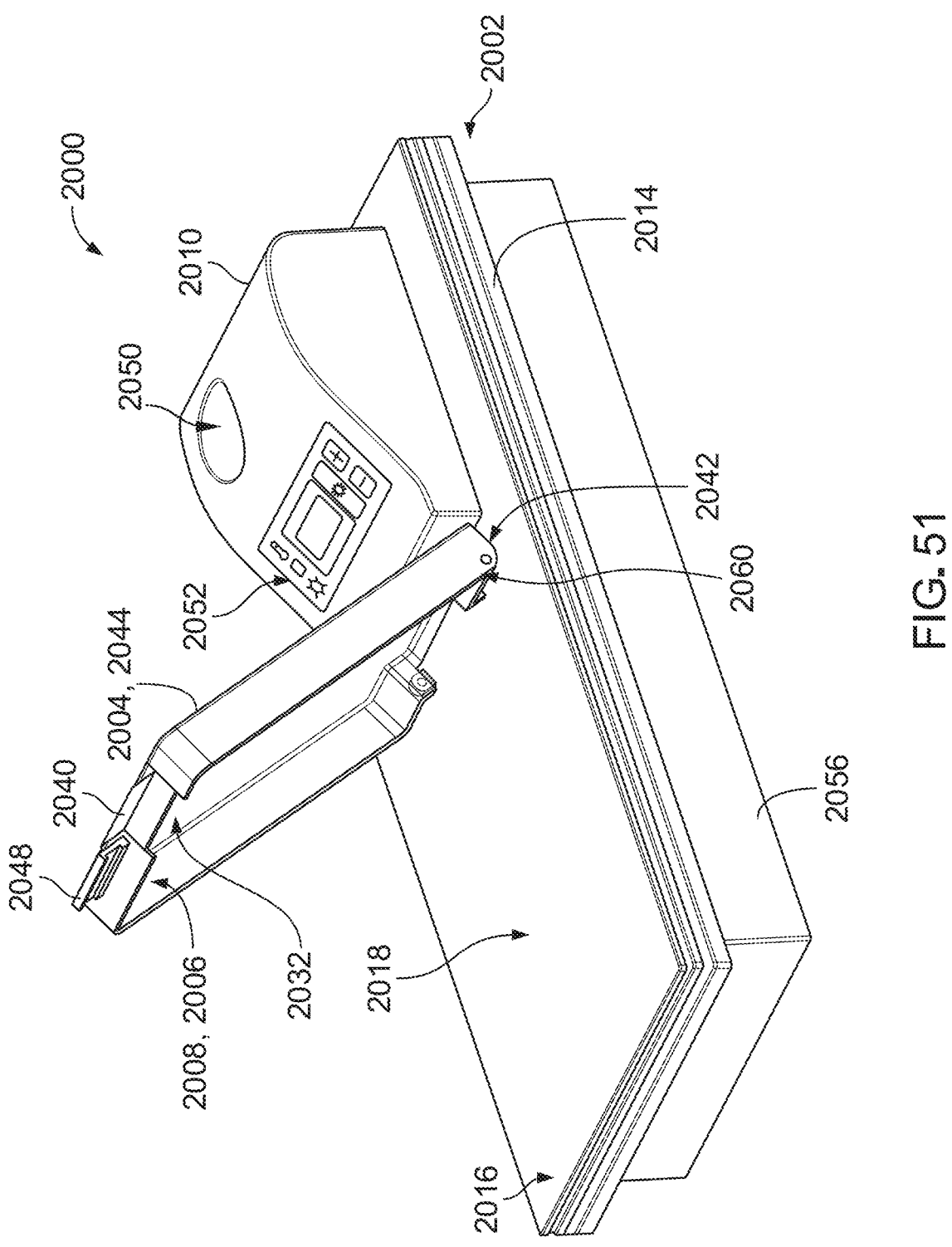

FIG. 51 is a perspective view of the modular incubator of FIG. 49 with the outer lid and the chamber wall together opened from a platform of the incubator module.

Figure 52:
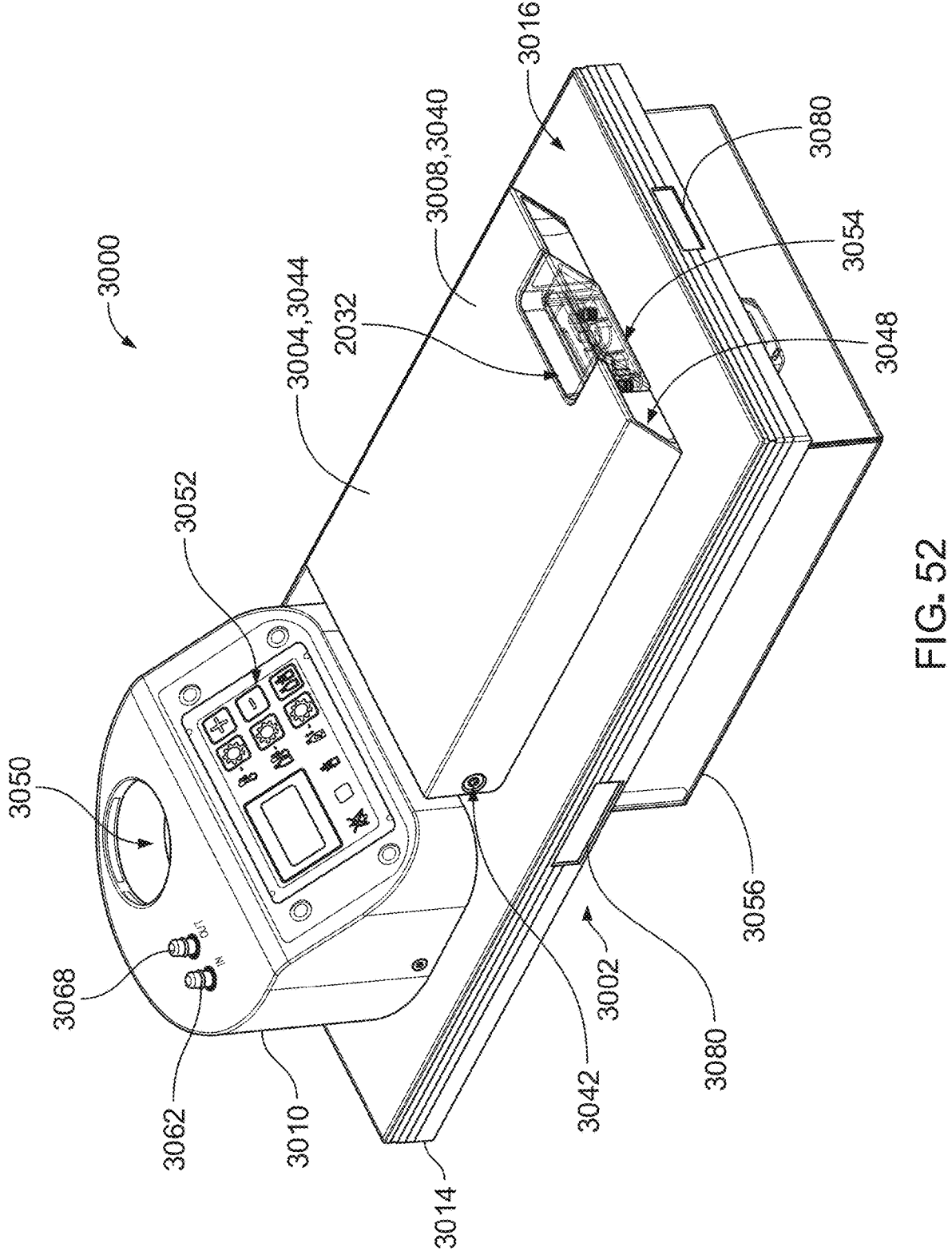

FIG. 52 is a perspective view of a modular incubator that is installable to any of the configurable workstations of FIGS. 1, 28, 37, and 38.

Figure 53:
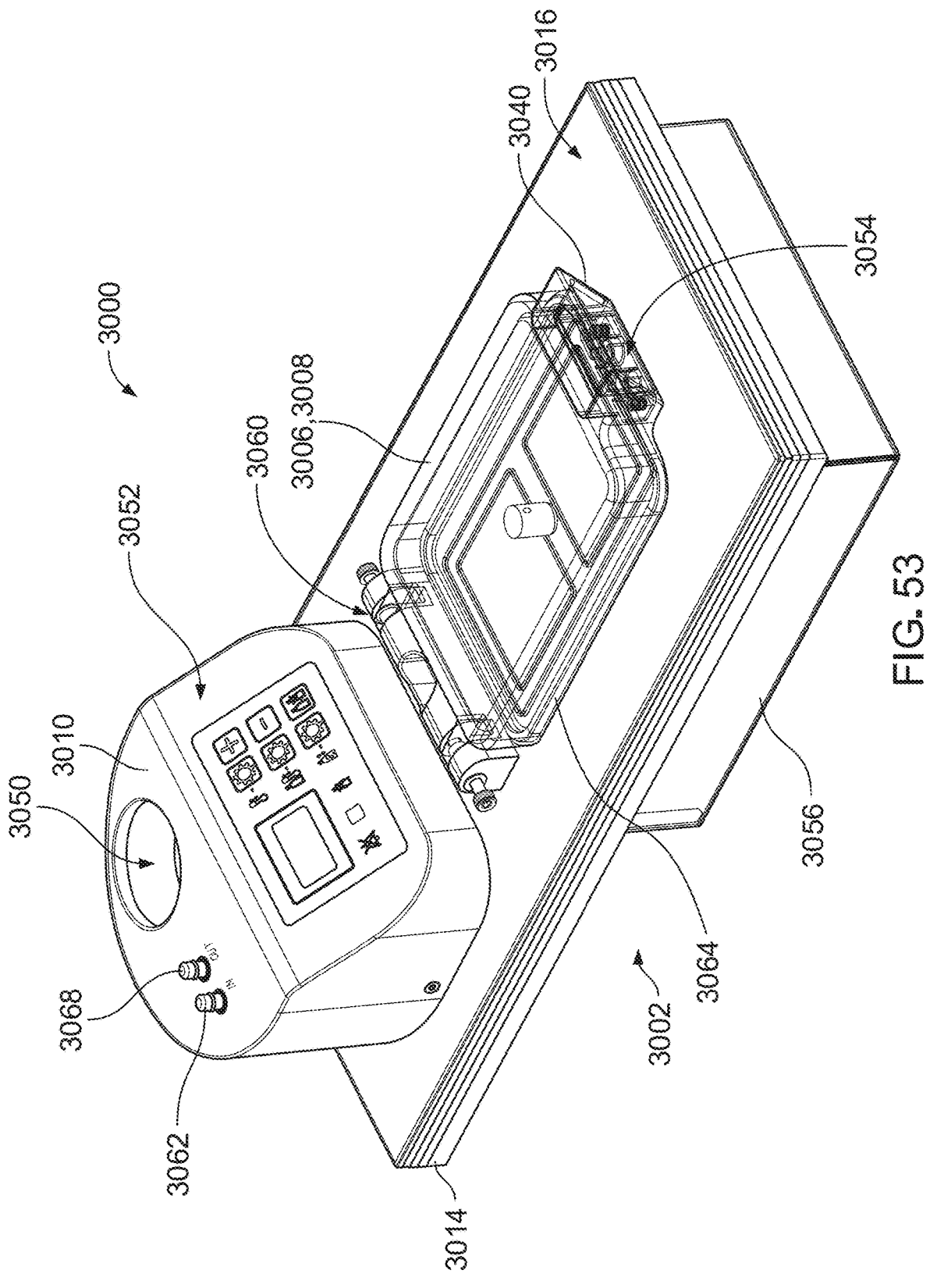

FIG. 53 is a perspective view of the modular incubator of FIG. 52 with an outer lid of the modular incubator omitted to show a chamber wall of the modular incubator.

Figure 54:
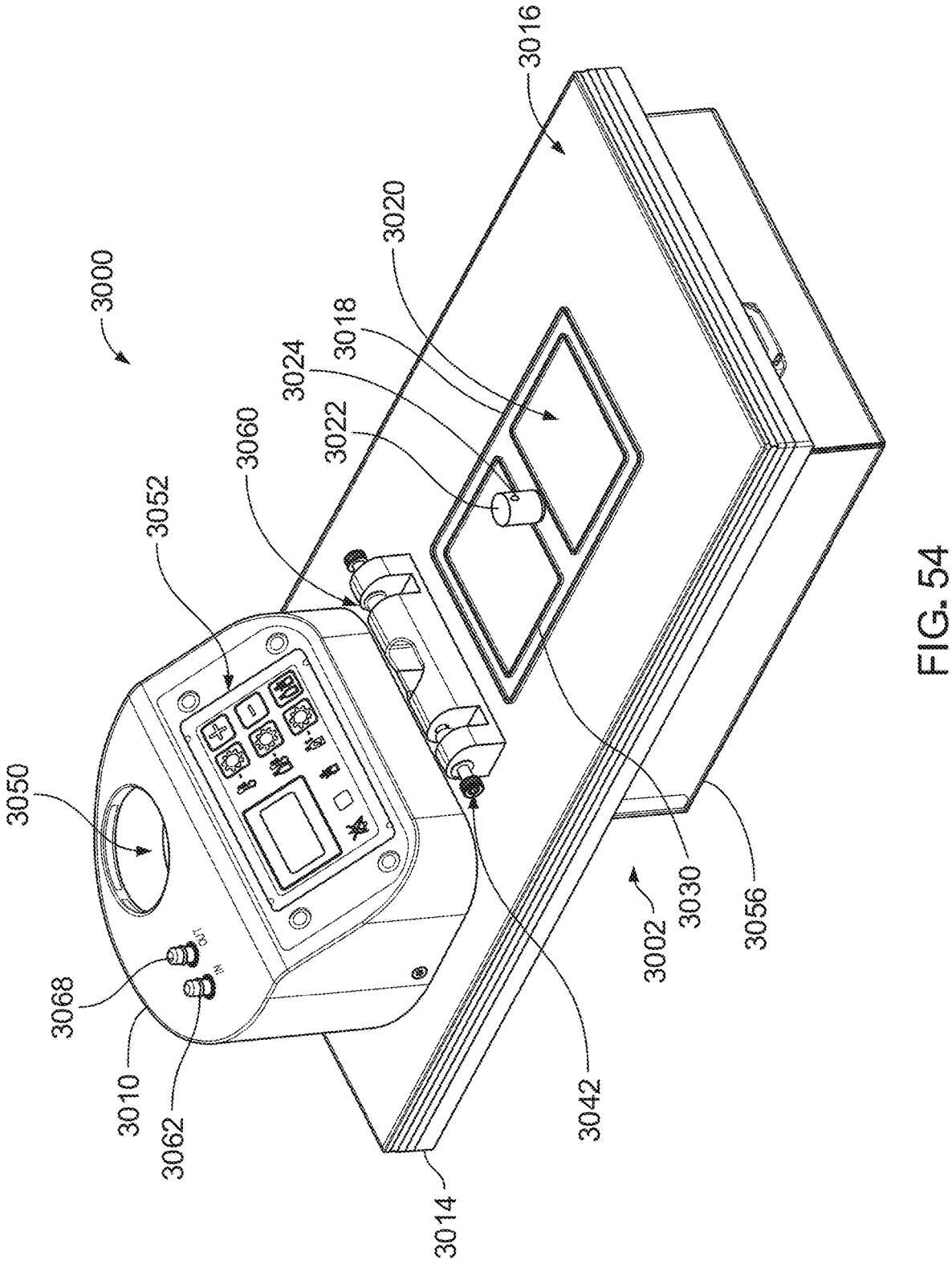

FIG. 54 is a perspective view of the modular incubator of FIG. 52 with the outer lid and the chamber wall omitted to show a platform and a gas distributor of the modular incubator.

Figure 55:
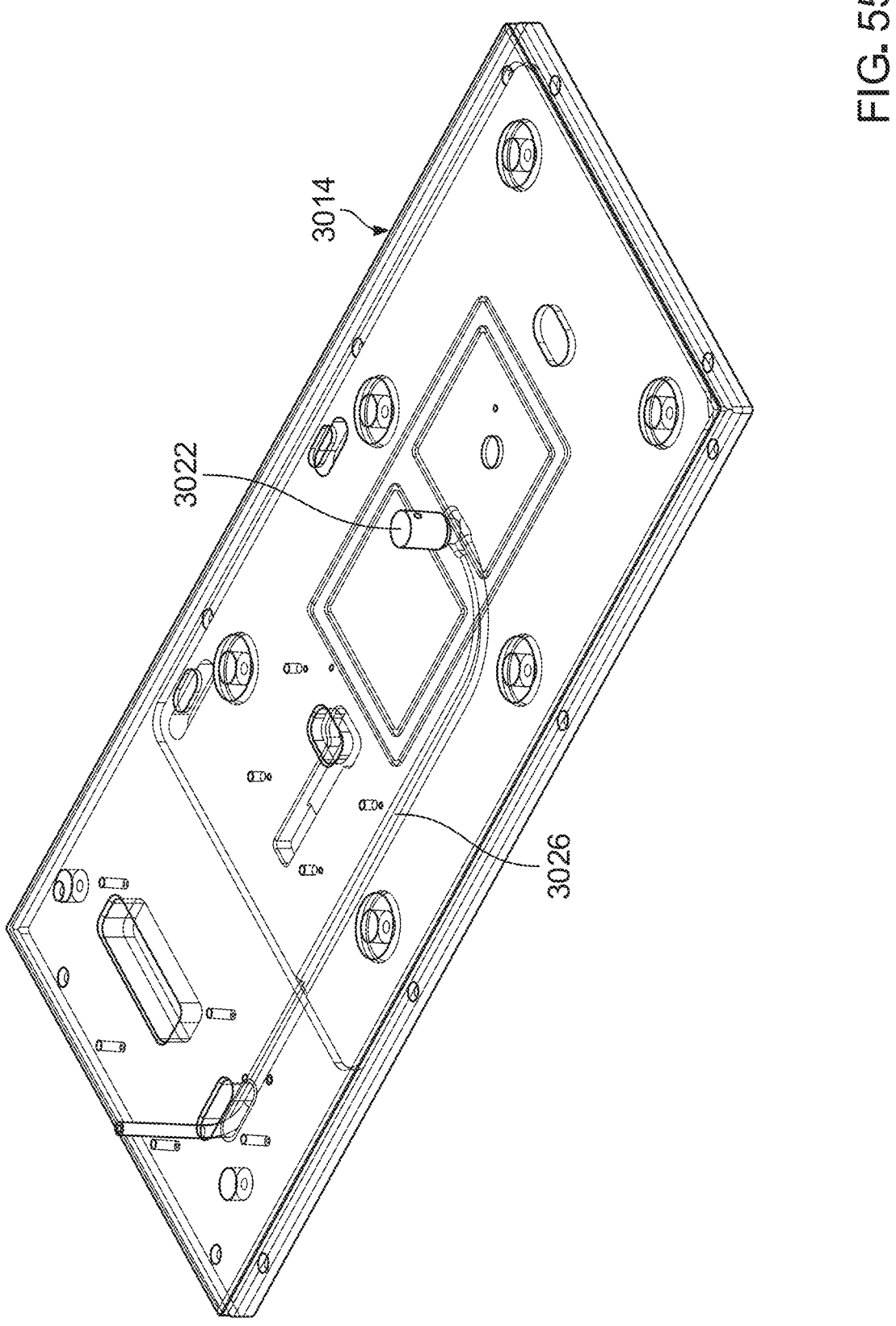

FIG. 55 is a perspective view of a gas line of the modular incubator of FIG. 52 as routed to the gas distributor of FIG. 54.

Figure 56:
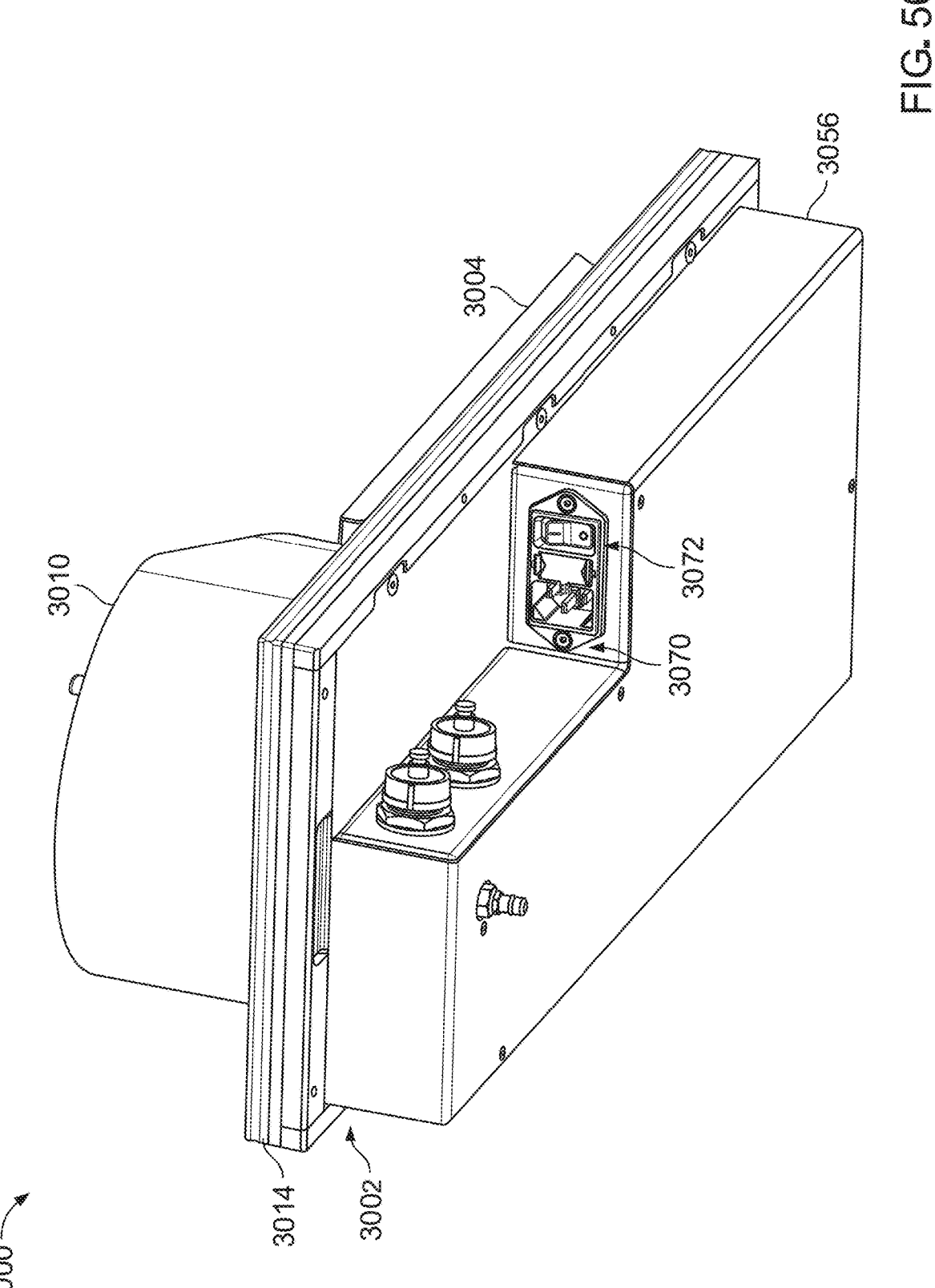

FIG. 56 is a side perspective cross-sectional view of the modular incubator of FIG. 52.

Figure 57:
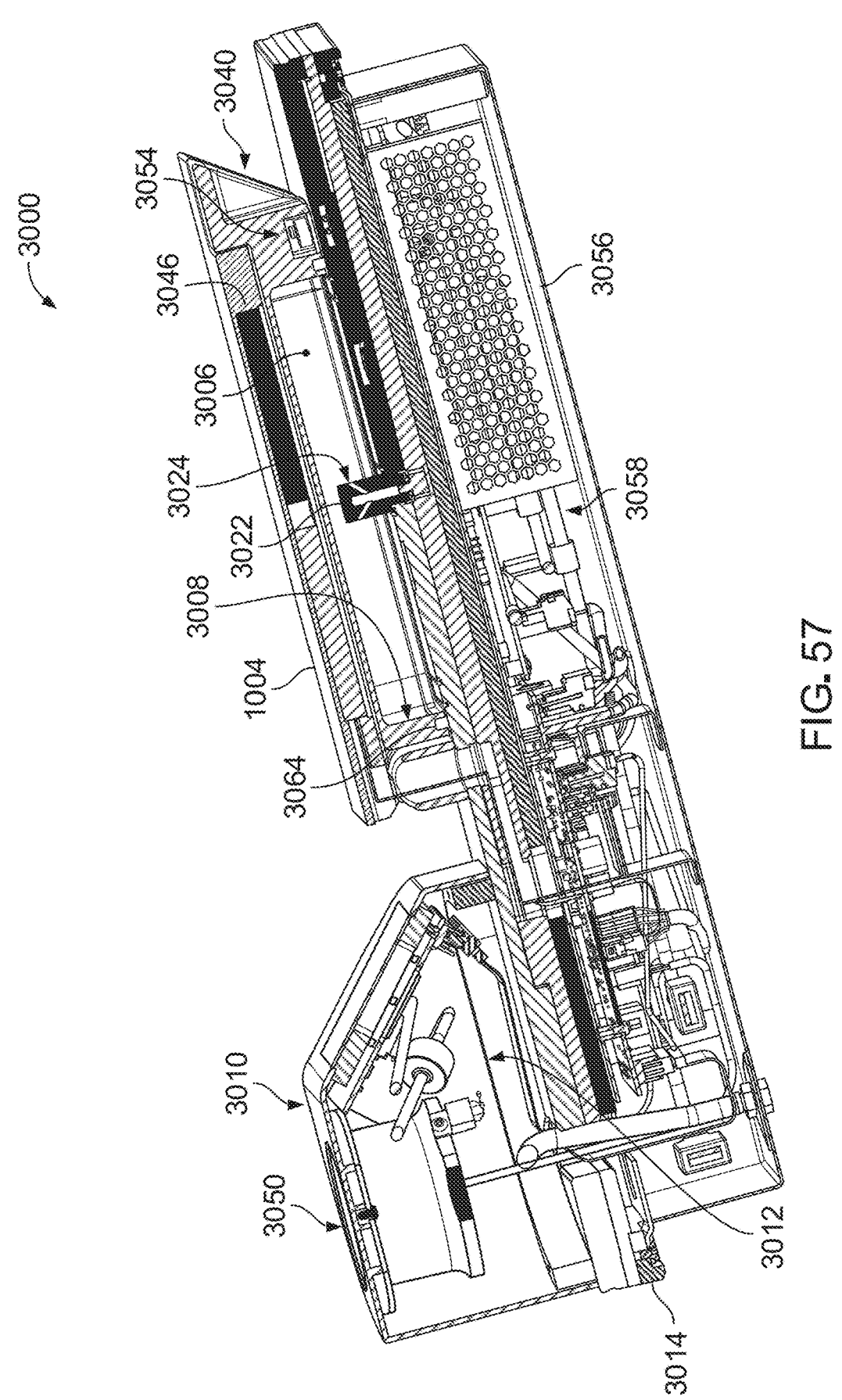

FIG. 57 is a rear perspective view of the modular incubator of FIG. 52.

Figure 58:
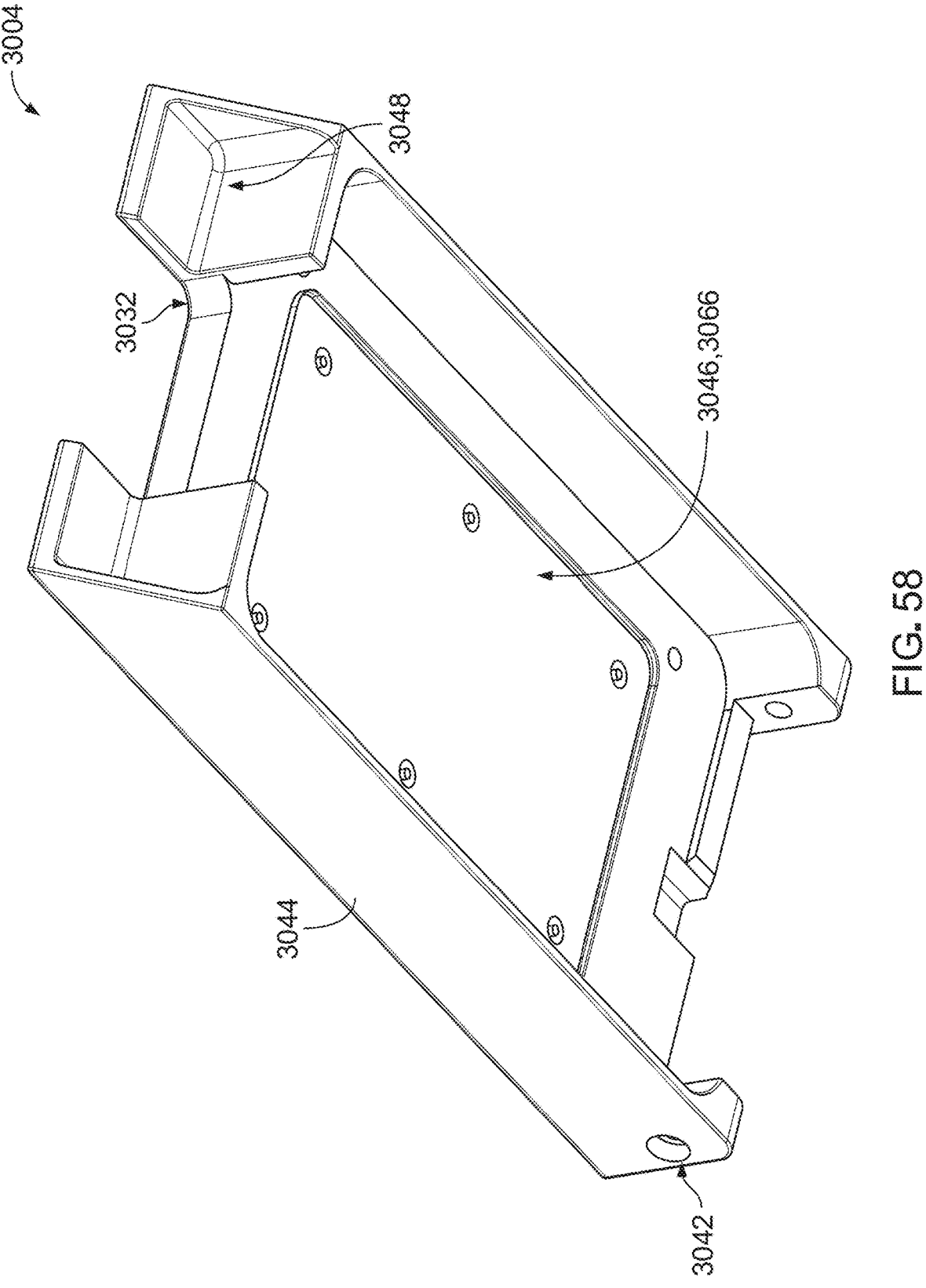

FIG. 58 is a bottom perspective view of the outer lid of the incubator module of FIG. 52.

DETAILED DESCRIPTION

Figure 2:
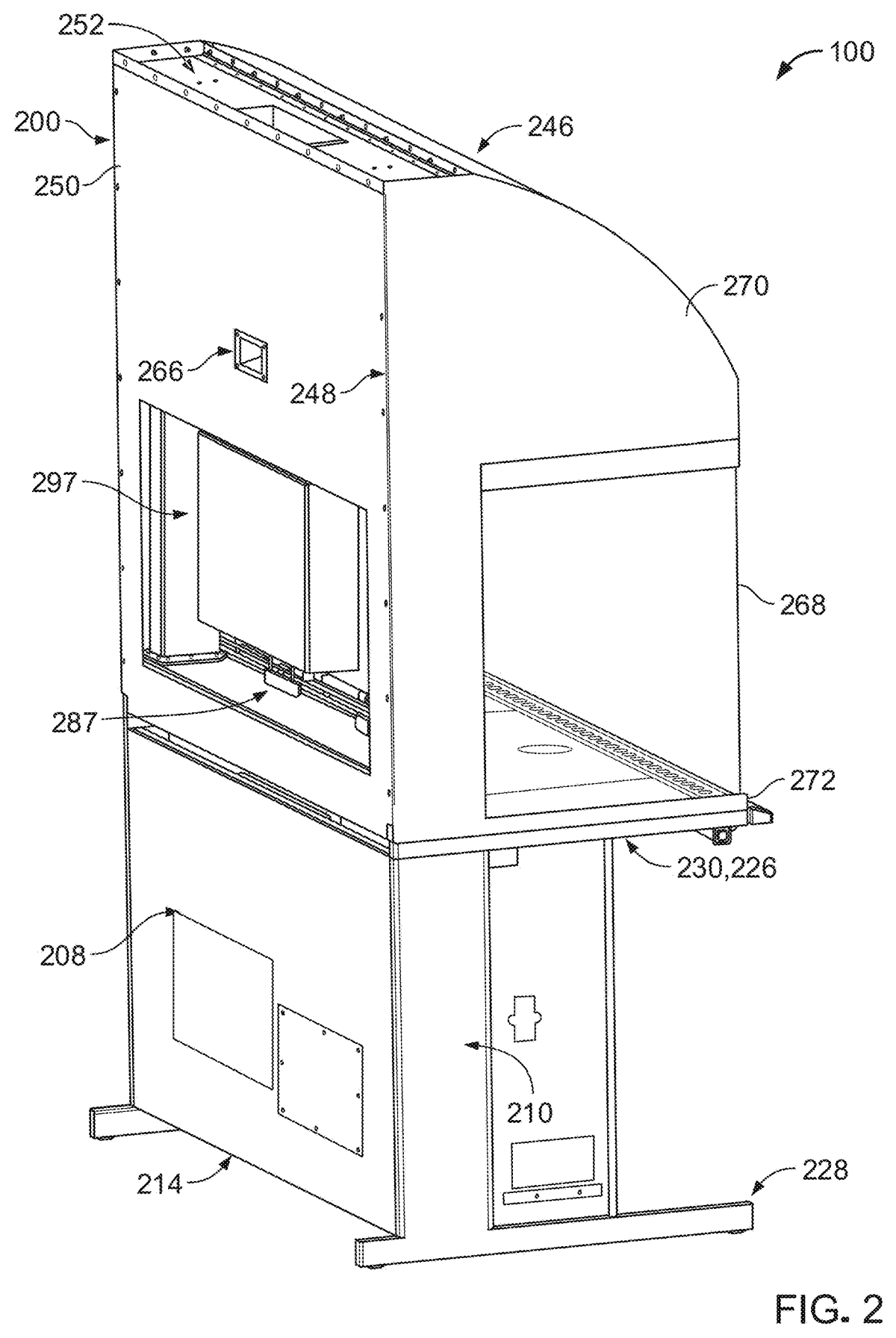

FIGS. 1 and 2 illustrate various views of a configurable workstation 100 (e.g., a biosafety cabinet) that provides a workspace 102 for carrying out biological protocols in a laboratory environment. Various biological protocols may be carried out in the workspace 102, such as those related to in vitro fertilization (IVF), cell examination, cell selection, and cell manipulation in the field of assisted reproductive technology (ART). For example, procedures involving one or more of vitrification of specimens, intracytoplasmic sperm injection (ICSI), embryo biopsy, insemination, sperm preparation, and egg selection are typically performed within the workspace 102. Example specimens that are typically handled in the workspace 102 during such procedures include oocytes, blastocysts, embryos, and other animal cells.

The configurable workstation 100 is a networked system with a modularized design that is customizable on-site at a laboratory to meet various laboratory requirements and provide functional capabilities needed to perform selected procedures at the configurable workstation 100. Such requirements may relate to one or more of cost, layout, sterility, airflow patterns, data access, data transfer, sample tracking, work-flow tracking, quality control, temperature control, gas mixture control, incubation, and control of embryo or oocyte environment. The customizable design of the configurable workstation 100 facilitates upgrading of existing technologies and integration of new technologies at the configurable workstation 100 without replacing the configurable workstation 100 with an entirely new workstation at significant cost and laboratory downtime. The customizable design enables easy integration of radio frequency identification (RFID) capabilities for tracking IVF specimens and other specimens. The configurable workstation 100 includes a frame 200, multiple modules 300 that may be selectively installed to the frame 200 as desired for customizing a functional profile of the configurable workstation 100, an air duct system 400 that can be removed from or installed to the frame 200 for modifying an airflow path at the configurable workstation 100, and a server computer 500 that implements a web application to provide a central user interface for communicating with the configurable workstation 100.

The frame 200 is operable to perform clinical functions and is therefore classified as a medical device that is subject to a regulatory review process carried out by a regulatory entity (e.g., the U.S. Food and Drug Administration (FDA) or another regulatory entity). The frame 200 includes an upper panel structure 202, a lower panel structure 204, and a table 206 that extends horizontally from the upper and lower panel structures 202, 204.

Figure 3:
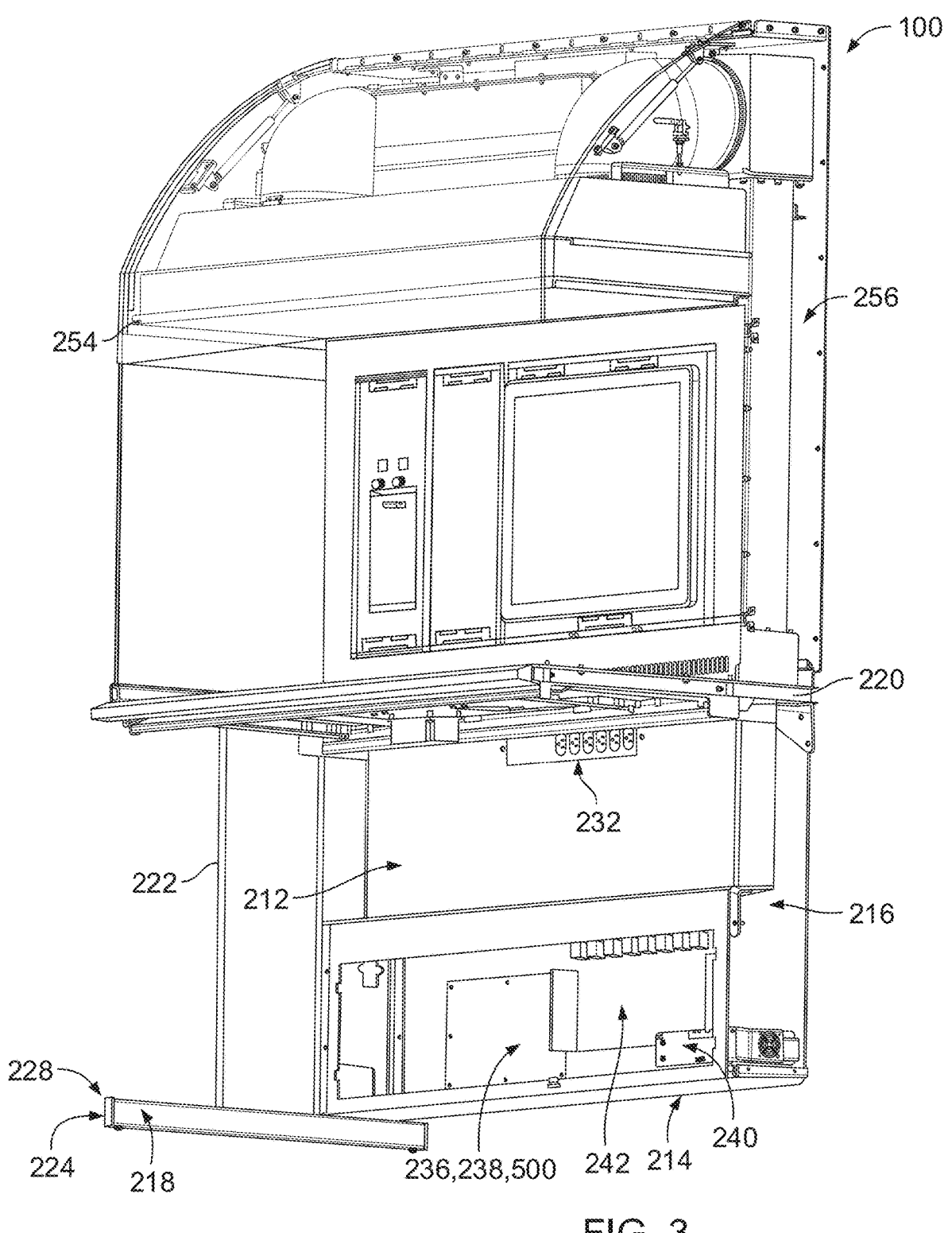
FIG. 3 is a front perspective view of the configurable workstation of FIG. 1 with certain panels of the configurable workstation omitted to expose certain interior components.
Figure 4:
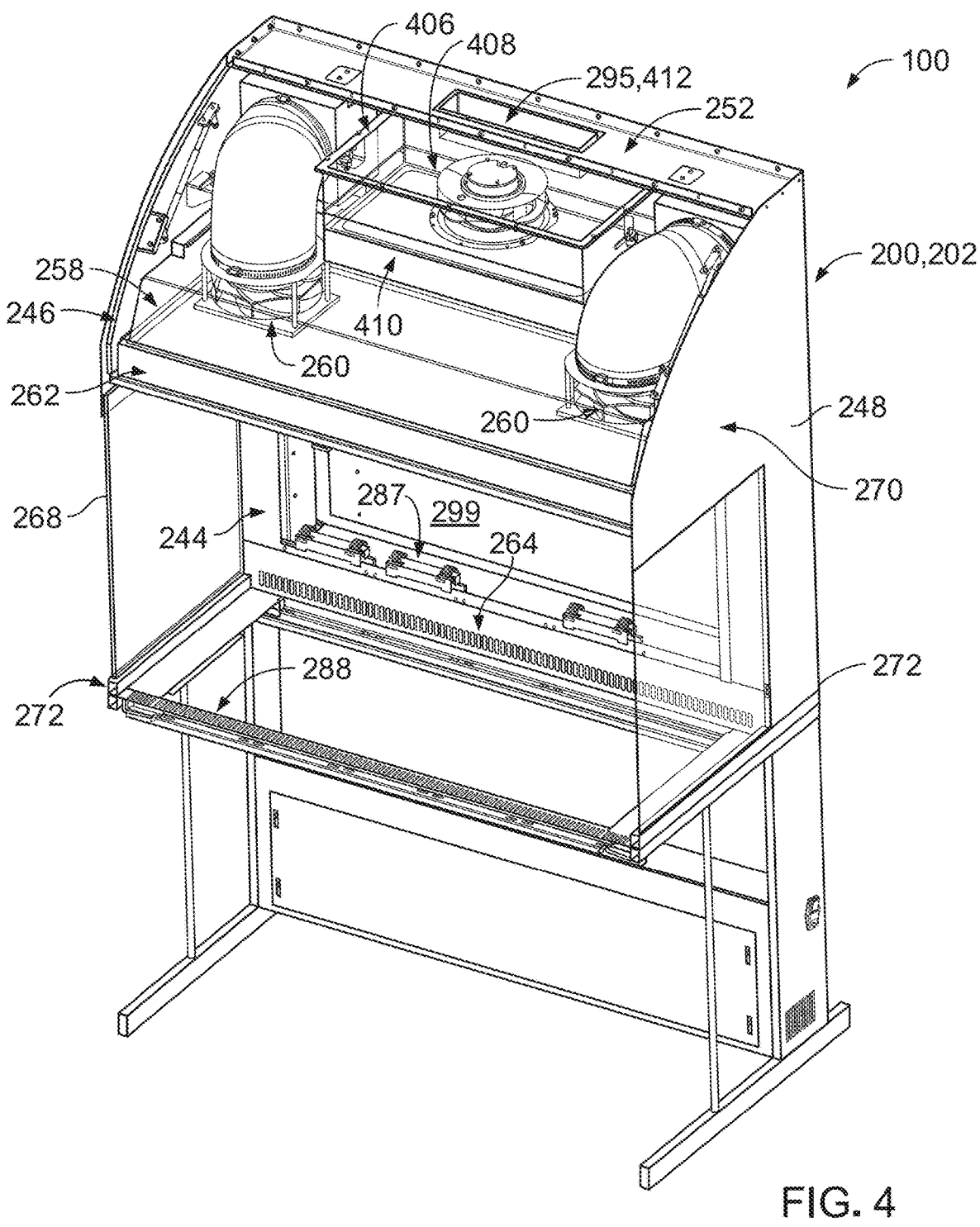
FIG. 4 is a front perspective view of the configurable workstation of FIG. 1 with modules and certain other components of the configurable workstation omitted to expose certain interior features.

Referring to FIGS. 1-3, the lower panel structure 204 includes a rear panel 208, two lateral panels 210, a front panel 212, and a lower panel 214 that together define an enclosure 216 that houses various components of the configurable workstation 100. The lower panel structure 204 further includes lower inner rails 218, upper inner rails 220, and support columns 222 that extend between the lower and upper inner rails 218, 220. The lateral panels 210 define lower outer rails 224 and upper outer rails 226. The lower outer rails 224 and the lower inner rails 218 together form feet 228 that support the weight of the configurable workstation 100. The upper outer rails 226 and the upper inner rails 220 together form upper support beams 230 that in part support the table 206, as will be discussed in more detail below.

The front panel 212 is equipped with multiple power outlets 232 at which any of the modules 300 or other accessory devices can be powered at the configurable workstation 100. The enclosure 216 houses several components that are accessible via a service panel 234. For example, the enclosure 216 houses a control module 236 that includes a printed circuit board (PCB) 238 on which the server computer 500 is implemented, a power supply 240 that powers the configurable workstation 100, and a power switch module 242 that manages distribution of the power.

Referring to FIGS. 1-4, the upper panel structure 202 includes a front panel 244 defining an opening 299 at which various modules 300 can be installed, a front cover 246, two lateral panels 248, a rear panel 250 defining an opening 297 that provides rear access to the opening 299, an upper panel 252, and a lower panel 254 that together define an enclosure 256 (e.g., a workstation hood) that houses various components of the configurable workstation 100. For example, the enclosure 256 is equipped with a pressure chamber 258 housing two oppositely located fans 260 that provide downward airflow within the frame 200, and a high-efficiency particulate air (HEPA) filter 262 located beneath the pressure chamber 258 for filtering the air. The front cover 246 is openable (e.g., pivotable at the upper panel 252) to switch out the HEPA filter 262 as needed.

The opening 299 of the front panel 244 has a rectangular shape to accommodate selected modules 300. The opening 299 typically has a width of about 1.0 m to about 2.0 m and a height of about 0.4 m to about 0.7 m (e.g., 1.08 m in the case of a 4-foot wide frame 200 or 1.67 m in the case of a 6-foot wide frame 200). The front panel 244 defines a row of vertically oriented, elongate openings 264 for airflow through the upper panel structure 202, as will be discussed in more detail below. The upper panel 252 defines a rectangular opening 295 through which air can flow along a selected airflow path at the frame 200.

Still referring to FIGS. 1-4, the rear panel 250 is equipped with a handle 266 for holding the rear panel 250 during assembly with or disassembly from the remaining components of the frame 200. The lower panel 254 is also equipped with lights that can illuminate the workspace 102. The upper panel structure 202 further includes lateral panels 268 that in part define the workspace 102 of the configurable workstation 100. The lateral panels 268 are transparent or translucent and therefore provide lateral viewing windows for the workspace 102. Example materials from which the lateral panels 268 may be made include glass, acrylic, or other types of transparent plastic. The lateral panels 248 define upper panel regions 270 that laterally close off the enclosure 256 and lower support beams 272 that in part provide support for the table 206.

FIG. 5 illustrates a schematic diagram of the control module 236 of the frame 200. The frame 200 is a stand-alone unit. That is, although the frame 200 has built-in structural and electronic support for the modules 300, the frame 200 can operate even without installation of any of the modules 300. Accordingly, the control module 236 of the frame 200 includes built-in hardware 293, built-in firmware 291, and a built-in user interface 289 to carry out its functionality. The control module 236 also includes the PCB 238 (e.g., a local mesh-network communication board), which implements the server computer 500.

Referring to FIGS. 4 and 6-8, the air duct system 400 can be removed from or installed to the frame 200 to change an air flow path at the configurable workstation 100. The air duct system 400 includes a duct frame 402, two air ducts 404 joined to the duct frame 402, a pressure chamber 406 housing a fan 408 for exhausting air out of the exhaust vent 412 and the upper opening 295 frame 200, a HEPA filter 410 for filtering the air flowing into the pressure chamber 406, and an exhaust vent 412 through which air flows out of the pressure chamber 406 and subsequently out of the frame 200 of the configurable workstation 100. The air ducts 404 are sealed to the duct frame 402 and are respectively located above and sealed to the fans 260 of the frame 200. The fans 260 are operated to rotate in a first rotational direction to flow air downward through the HEPA filter 262 and into the workspace 102 of the workstation. The fan 408 is operated to rotate in an opposite, second rotational direction to flow air upward through the HEPA filter 410, the pressure chamber 406, the exhaust vent 412, and out of the frame 200.

The duct frame 402 includes two compartments 414 that respectively interface with the air ducts 404, two vertical ducts 416 that extend from the compartments 414, a horizontal duct 418 that joins the two vertical ducts 416, a lower horizontal rear bracket 420 joined to the horizontal duct 418, and an upper horizontal rear bracket 422 that extends between the vertical ducts 416. Each compartment 414 is equipped with a vertical bracket 424. The air duct system 400 can be installed (e.g., attached) to the frame 200 with fasteners at the brackets 420, 422, 424. The horizontal duct 418 defines an elongate slot 426 that aligns with the row of openings 260 in the front panel 244 of the upper panel structure 202 to allow air to flow into duct frame 402. The horizontal duct 418 also defines two oppositely located rectangular openings 428 that align with duct components of the table 206 to allow air to flow into the duct frame 402, as will be discussed in more detail below.

The duct frame 402 typically has a total height of about 0.9 m to about 1.5 m, a total width of about 1.1 m to about 2.0 m, and a total depth of about 0.1 m to about 0.2 m. The duct frame 402 is a rigid structure that is typically made of one or more materials, such as steel, rubber, aluminum and thermal plastics. The air ducts 404 typically have an inner cross-sectional diameter of about 10 cm to about 25 cm. The air ducts 404 are flexible conduits that are typically made of one or more materials, such as aluminum, steel or plastics. The duct frame 402 and the air ducts 404 typically have a combined weight of about 20 lbs to about 45 lbs for easy handling.

Figure 10:
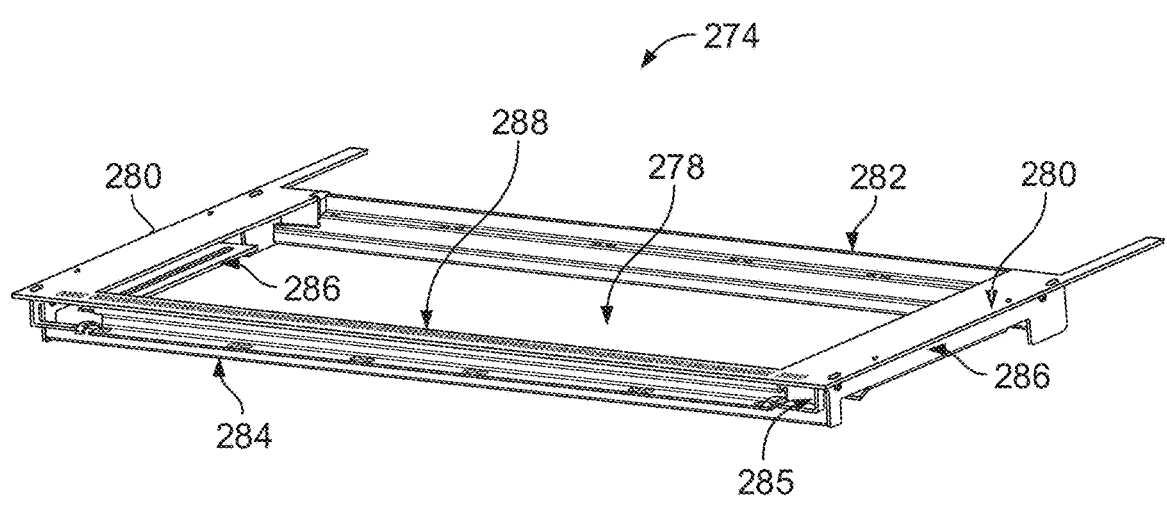
FIG. 10 is a perspective view of a platform of the table of FIG. 9.

Referring to FIGS. 9-11, the table 206 of the frame 200 includes a platform 274 and a slidable air duct 276 that can be withdrawn from and slid into the platform 274 like a drawer. The platform 274 defines an opening 278 at which various modules 300 can be installed to form a flat work surface within the workspace 102. The opening 278 has a rectangular shape to accommodate selected modules 300. The opening 278 typically has a width of about 1.0 m to about 2.0 m (e.g., 1.05 m in the case of a 4-foot wide frame 200 or 1.7 m in the case of a 6-foot wide frame 200) and a depth of about 0.4 m to about 0.6 m.

The platform 274 also defines two lateral sections 280 by which the table 206 is attached to the lower support beams 272 of the upper panel structure 202 and the upper support beams 230 of the lower panel structure 204. The lateral sections 280 also extend rearwardly along the horizontal duct 418 of the air duct frame 400. The platform 274 further defines a rear bracket 282 and a front bracket 284 by which the modules 300 can be attached to the table 206 and lateral brackets 286 that provide support for the slidable air duct 276. The rear and front brackets 282, 284 define rectangular openings 285 through which components of the slidable air duct 276 pass to communicate with the air duct system 400. The platform 274 also defines a frontal row of elongate openings 288 through which air in the workspace 102 can flow into the slidable air duct 276 and subsequently into the air duct system 400.

Still referring to FIGS. 9-11, the slidable air duct 276 defines an elongate handle 290 by which the slidable air duct 276 can be pulled from the table 206 and by which the slidable air duct 276 can be pushed (e.g., slid) forward along the lateral brackets 286 of the table 206. The slidable air duct 276 further defines an open front channel 292 that extends along the handle 290 and two lateral conduits 294 that extend rearwardly from the front channel 292. A filter may be positioned within the slidable air duct 276 at a front end of each lateral conduit 294 to prevent any large objects from entering the lateral conduits 294.

Referring to FIGS. 12 and 13, when the slidable air duct 276 is positioned at a rearward most position (e.g., pushed against the platform 274), the front channel 292 is positioned underneath the openings 288 of the platform 274, and rear ends 296 of the lateral conduits 294 are positioned within the rectangular openings 428 of the duct frame 402. One or more seals 298 may be installed along the slidable air duct 276 to seal the slidable air duct 276 to the rectangular openings 428 and to the platform 274. The slidable air duct 276 may be pulled forward from the platform 274 so that the front channel 292 and the lateral conduits 294 can be cleaned and sanitized of any fluids or other objects that have fallen into the slidable air duct 276. The slidable air duct 276 may remain in partial contact with the platform 274 or may be removed completely from the platform 274.

The frame 200 is a rigid structure that typically has a total height of about 1.8 m to about 3.0 m, a total width of about 1.0 m to about 2.0 m, and a total depth of about 0.5 m to about 1.0 m. The various components of the frame 200 (e.g., including the upper panel structure 202, the lower panel structure 204, and the table 206) are typically made of one or more materials that can chemically withstand various laboratory cleaning substances. Example materials from which the frame 200 may be made include steel, aluminum, glass, and plastic. The frame 200 (e.g., excluding the modules 300 and the air duct system 400) typically has a weight of about 350 lbs to about 1200 lbs.

Referring to FIG. 14, the workstation 100 is embodied as a Class II biosafety cabinet (e.g., with or without any of the illustrated modules 300), such that an airflow path 104 at the workstation 100 is designed to protect personnel working at the workstation 100, an environment at which the workstation 100 is located, and any specimens (e.g., product) handled in the workspace 102 from contaminants or other particulates present near the workstation 100. In order to meet certain requirements of a Class II biosafety cabinet, the fans 260 within the pressure chamber 258 recirculate air within the workspace 102 along the airflow path 104 by flowing the air beneath the table 206 and back through the HEPA filter 262 before the air reenters the workspace 102.

For example, air within the workspace 102 is circulated in a downward direction and then rearwardly into the openings 264 of the upper panel structure 202, where the air passes through the elongate slot 426 of the horizontal duct 418 to enter the duct frame 402. Air within the workspace 102 is also circulated forwardly into the openings 288 of the platform 274, where the air passes into the front channel 292 of the slidable aid duct 276, flows further into the lateral conduits 294, and then flows through the rectangular openings 428 of the horizontal duct 418 to enter the duct frame 402. Air within the horizontal duct 418 is circulated upward through the duct frame 402, drawn into the air ducts 404, and driven downward by the fans 260 through the HEPA filter 262 to remove any harmful particles or contaminants before reentering the workspace 102. Thus, the fans 260 circulate air along the airflow path 104 through the workspace 102, the slidable air duct 276, and the duct frame 402 to meet certain Class II requirements. By flowing the air laterally towards sides of the frame 200 and rearwardly through the front panel 244, the air avoids contact with other components of the configurable workstation 100 which may otherwise increase the likelihood of air contamination, as is the case for conventional biosafety cabinets.

The slidable air duct 276 of the table 206 and the air duct system 400 are designed such that the airflow path 104 is unaffected by the combination of modules 300 installed at the frame 200. Independence of the airflow path 104 from the modules 300 advantageously permits factory testing of the airflow path 104 prior to shipment of the configurable workstation 100 to a customer site.

Referring to FIGS. 15, the modules 300 are standalone units and include functional modules and non-functional blanks that can be selectively installed to the table 206 and the front panel 244 of the frame 200 to customize a functional profile of the workstation 100. For example, by selectively installing desired modules 300, the functional profile may be customized to provide capabilities required to carry out certain experimental procedures, to meet certain requirements of a laboratory at which the workstation 100 is located, or to identify specimens in a certain manner. The functional modules are operable to perform clinical functions and are therefore classified as medical devices that are subject to regulatory review. The non-functional blanks cannot perform any clinical functions and are therefore not subject to regulatory review.

The modules 300 include table-top modules 302 that are designed to lay horizontally and to be installed at the table 206. Depending on a width of the frame 200, a total number of 5 to 10 modules 302 may be installed to the table 206 at the same time. Once the modules 302 are positioned at the table 206, the modules 302 need to be flush with each other so that certain specimens, tools, equipment, and procedures are not damaged, obstructed, or otherwise flawed due to unexpected variability in height of the work surface across the table 206. Additionally, gaps between the modules 302 should be minimized to ensure smooth surface transitions between adjacent modules 302. Gaps between the modules 302 should also be sealed to prevent any materials from leaking into the gaps and subsequently resulting in bacterial growth that will be detrimental to biomedical procedures performed in the workspace 102.

The modules 302 include modules 302*a*-302*i*. The module 302*a* is a heating plate with microscope mounting holes and a heated transparent glass. The module 302*b* is a heating plate with microscope mounting holes, a heated transparent glass, and built-in RFID capabilities for detecting RFID tags that identify a specimen for patient sample tracking. The module 302*c* is an anti-vibration table that provides a platform template with four holes at which an anti-vibration table can be installed at the table 206. The module 302*d* is a heating plate that can achieve a user-set temperature, and the module 302*e* is a heating plate with RFID capabilities. The module 302*f* is an incubator that can provide one or more features including pH monitoring, programmable heat and gas cycles, controlled heating, and $CO_2$, $O_2$, and $N_2$ gas mixtures suitable for long-term embryo incubation and development. The module 302*g* is a cooling unit that can cool or vitrify a specimen. The modules 302*a*-302*g* are medical devices that are subject to regulatory review.

The module 302*h* is a blank that can fill in part of the opening 278 at the table 206 to provide a complete table-top surface, and the module 302*i* is a blank with RFID capabilities that can fill in part of the opening 278 at the table 206 to provide a complete table-top surface. The modules 302*h*, 302*i* are non-medical devices and are therefore not subject to regulatory review. Any of the modules 302*a*-302*i* may additionally provide a light source for the workspace 102.

The modules 300 also include wall modules 304 that are designed to be oriented vertically and to be installed at the front panel 244 of the upper panel structure 202. Depending on a width of the frame 200, a total number of 5 to 10 modules 304 may be installed to the front panel 244 at the same time. The modules 304 include modules 304*a*-304*f*. The module 304*a* is a humidifier that can heat containers of water and flow gas through the water to provide humidified gas for an IVF procedure or other procedures carried out in the workspace 102. The module 304*a* is a medical device that is subject to regulatory review. The module 304*b* is an ICSI arch that provides a concave cavity to allow room for micromanipulators and inverted microscopes to be installed in the workspace 102. The module 304*c* is a wall tunnel that provides a passageway for a user to pass items (e.g., equipment, specimens, and other items) through the front and rear panels 244, 250 of the upper panel structure 202. The module 304*d* is a monitor (e.g., a computer monitor or other display, such as a 27 inch or 32 inch monitor).

The module 304*e* is an outlet panel that may provide one or more universal power outlets or USB outlets. The module 304*f* is a blank that can fill in part of the opening 299 at the front panel 244 of the upper panel structure 202 to provide a complete wall surface. The modules 304*b*-304*f* are non-medical devices and are therefore not subject to regulatory review. Any of the modules 304*a*-304*f* may additionally provide a light source for the workspace 102.

FIG. 16 illustrates a schematic diagram of a module 300 that may represent any of the above-described modules 302*a*-302*i*, 304*a*-304*f*. The modules 300 are self-contained units. That is, as long as power is supplied to a module 300 at a built-in power port 306, the module 300 can operate even without installation to the frame 200 and can perform their intended functionalities without connection to the web application implemented on the server computer 500. Accordingly, each functional module 300 includes built-in equipment 308 for carrying out its dedicated laboratory function (e.g., such as any of the functions discussed above with respect to FIG. 15), built-in hardware 310, built-in firmware 312, and a built-in user interface 314 to carry out its functionality. Each module 300 also has a built-in local mesh network communication board 316 to allow for wireless communication to the server computer 500 to receive user inputs. The modules 300 may have alarms and controls for basic functions (e.g., a set point edit), while other functions (e.g., calibration, logging, and other functions) may be performed at an application running on the server computer 500, as will be discussed in more detail below.

Referring to FIGS. 17-19, each table-top module 302 includes one or more generally flat components that form a housing 318. The module 302 is placed atop the rear bracket 282 and the front bracket 284 of the table 206 within the opening 278 of the platform 274 for installation to the table 206. The module 302 is attached to the brackets 282, 284 with one or more fasteners 320 (e.g., socket screws or the like) that pull the module 302 downward towards the table 206 to lock the module 302 in position. The module 302 is also engaged with the brackets 282, 284 with one or more fasteners 322 (e.g., set screws or the like) that push the module 302 upward for level adjustment of the module 302 with the platform 274 of the table 206 and with any adjacent module 302 to provide a flat work surface across the table 206.

Referring to FIGS. 20 and 21, the housing 318 defines multiple recesses 324 along lateral edges 326 that are sized to accommodate an attachment block 328 by which the module 302 can be secured laterally to an adjacent module 302. The recesses 324 and the attachment blocks 328 respectively define holes 330, 332 through which a fastener can be passed to secure the attachment block 328 to the housing 318 of the module 302. A fastener 336 can be passed through vertical slots 338 of respective adjacent adjustment blocks 328 attached to adjacent modules 302 to secure the modules 302 to each other laterally (e.g., to pull the adjacent modules 302 towards each other). A length of the vertical slot 338 allows for flexible vertical positioning of the adjacent adjustment blocks 328 (e.g., being attached to the modules 302) as desired to level the modules 302 with respect to each other.

Referring to FIGS. 22-24, the housing 318 of the module 302 also defines protrusions 340 directed inwardly from the lateral edges 326. Each protrusion 340 defines a central opening 342 that accommodates a screw fasteners 346 by which the module 302 can be laterally secured to and leveled with respect to an adjacent module 302 alternatively or additionally using an adjustment block 350. Optional positions of the adjustment block 350 do not interfere with optional positions of the adjustment block 328. The adjustment block 350 has a pattern defined by holes 352 and slots 354. A length of the slots 354 allows for flexible lateral positioning of fasteners 348 within the slots 354 for desired lateral positioning of the module 302 with respect to an adjacent module 302. The fasteners 348 (e.g., socket screws or the like) are used to pull the module 302 towards the adjustment block 350 to lock a position of the adjustment block 350 in place against the adjacent modules 302, while the fasteners 346 (e.g., set screws of the like) are used to push the modules 302 upward as desired to level modules 302 with respect to each other.

Once secured in position, adjacent modules 302 define an intermediate groove 356 along the lateral edges 326. Each module 302 is provided with a gasket 358 that may be pressed into the groove 356 to prevent any spills that occur atop the table 206 from flowing downward in between the modules 302.

Referring to FIGS. 25 and 26, each wall module 304 includes an installation panel 360 that is attachable via fasteners (e.g., screw fasteners or other fasteners) along upper and lower edges 362, 364 to the front panel 244 of upper panel structure 202 of the frame 200. Various equipment features 308 may be assembled with the installation panel 360, depending on a functionality of the module 304. Once secured in position, adjacent modules 304 define an intermediate groove 366 along the lateral edges 368. Each module 304 is provided with a gasket 370 that may be pressed into the groove 366 to prevent any undesired airflow between the modules 304. The gasket 370 includes an insertion piece 372 that is pressed into the groove 366 and a flange 374 that covers the groove 366 to provides a seamless feel and appearance across the front panel 244.

Referring again to FIGS. 2 and 4, the installation panel 360 is also equipped with one or more spring-like mechanisms 287 that secure the selected wall modules 304 in place in the opening 299 of the front panel 244. The spring-like mechanisms 287 are designed to latch onto and push on a rear wall rail 375 (refer to FIG. 12). The spring-like mechanisms 287 also provide support surfaces on which the modules 304 can rest against the rear wall rail 375 such that the spring-like mechanisms 287 support the weight of the modules 304. The combined features of, latching, pushing and support ensure the modules 304 are substantially flush against the opening 299 during operation.

In some embodiments of the modules 302, the housing 318 has a total length of about 0.6 m to about 0.7 m (e.g., about 0.64 m), a total width in a range of about 0.4 m to about 2.0 m (e.g., about 0.43 m), and a total thickness of about 0.025 m to about 0.7 m (e.g., about 0.03 m). Fasteners 320, 322 are typically secured to a housing 318 of a module 302 at a distance of about 0 cm to about 0.1 cm from a lateral edge 326 of the module 302. The adjustment block 328 typically has a length of about 1.0 cm to about 10.0 cm, a width of about 0.5 cm to about 3.0 cm, and a thickness of about 0.1 cm to about 2.0 cm. The adjustment block 350 typically has a length of about 0.5 cm to about 10.0 cm, a width of about 0.5 cm to about 4.0 cm, and a thickness of about 0.1 cm to about 3.0 cm. In some embodiments of the modules 304, the installation plate 360 has a length of about 40.0 cm to about 70.0 cm, a width in a range of about 18.0 cm to about 200.0 cm, and a thickness of about 0.1 cm to about 1.0 cm.

The housing 318, the installation plate 360, and the adjustment blocks 328, 350 are rigid structures that are typically made of one or more materials that can chemically withstand various laboratory cleaning substances. Example materials from which these components may be made include steel, aluminum, and thermal plastics. Each table-top module 302 typically weighs between about 10 lbs and about 60 lbs, while each wall module 304 typically weighs between about 2 lbs and about 50 lbs. The gaskets 358, 370 are also designed to withstand various laboratory cleaning substances and are therefore typically made of one or more materials, such as rubber, silicone, Buna-N-Nitrile, and soft plastics.

Referring to FIG. 27, the server computer 500 provides a central user interface between a user (e.g., an embryologist or another clinician) and the frame 200 and the modules 300 for monitoring statuses of the frame 200 and the modules 300 and for inputting parameters (e.g., set points) that govern operations of the frame 200 and the modules 300. The server computer 500 hosts a web application that can be accessed via a local Ethernet line or via WiFi connection to allow the user to control all functions of the frame 200 and the modules 300 from a single location. The web application, itself, does not perform any clinical functions. Rather, the web application conveys and communicates information gathered and handled by the frame 200, the modules 300, and users. The server computer 500 can establish connections to transfer data from the Ethernet line or WiFi connection to a local mesh network to which the modules 300 and the frame 200 are connected.

For example, the configurable workstation 100 operates on a network communication architecture 502 for the electronically-enabled devices 504 (e.g., the frame 200 and the modules 300) of the configurable workstation 100. The network communication architecture 502 alleviates privacy and performance concerns related to handling and storing medical data by supporting the devices 504 (e.g., devices 504a-504e) on a local network to reduce a chance of unauthorized access to the devices 504 and data stored on or transferred by the devices 504. The network communication architecture 502 is also flexible to handle a variable number of devices 504 without prior customization at a factory.

The architecture 502 includes three communication layers 506, 508, and 510. The layer 506 includes a local mesh network 512 (e.g., a private network) that provides communication connections between the devices 504. The layer 508 (e.g., a private network) provides connections between the devices 504 of layer 506 and the server computer 500. The layer 510 provides connections to remote servers or databases, such as a remote server on a cloud 514. The devices 504 and the server computer 500 provided by the workstation 100 are located in a laboratory of a medical facility (e.g., a hospital or a medical clinic), while the cloud 514 is located outside of the medical facility.

None of the devices 504 in the layer 506 is in direct communication with the cloud 514. Rather, all communications between the local mesh network 512 and the outside world are handled through the server computer 500. The server computer 500 verifies security criteria of data before allowing the data to be transferred to or from the outside world to the devices 506 in the local mesh network 512. This communication configuration protects security of data on the devices 504 and prevents unauthorized access from the outside world to the devices 504. In addition, even if connection between the server computer 500 and the cloud 514 is lost, the devices 504 can continue operating and communicating with each other through the local mesh network 512 and with the server computer 500.

The devices 504 (e.g., the devices 504a-504e) can communicate with each other through the local mesh network 512 in a wireless or wired manner. Additionally, each of the devices 504 can communicate with the server computer 500 independently of the other devices 504 such that if one device 504 malfunctions, the operation (e.g., functionalities and communications) of the remaining devices 504 will not be hindered or affected. In this manner, the network communication architecture 502 ensures device independence. Not only is independence of the devices 504 important for customer needs and technically robust, but such independence advantageously allows independent handling (e.g., access and control) of devices 504 in distinct regulatory classes. Accordingly, a regulatory approval status for one device 504 will not affect a regulatory approval status of another device 504.

Since a device 504 may have a processor with limited functionalities, the device 504 may need to communicate its data to a more powerful processor to further analyze, transform, or present the data to a user or to another computing device. For example, a device 504a may communicate its data to the server computer 500. The server computer 500 receives the data from the device 504a, analyzes the data, and provides an output based on the analysis. In some implementations, the output may be displayed to a user (e.g., at a module 304d installed to the front panel 244 of the frame 200). The user can also interact with the application running on the server computer 500 to send data to individual devices 504 via the local mesh network 512.

In some implementations, the output may be communicated to other computing devices. For example, the server computer 500 may send the output to a device 504b on the local mesh network 512, to a client device 516 (e.g., a tablet, a mobile phone, a laptop computer, or a desktop computer, etc.) to a local database or a local server 518, or to a remote server on the cloud 514. The server computer 500 can communicate with the local server 518 or with the client device 516 through a local area network (LAN) of the medical facility. The local server 518 can be located in the same medical facility as where the server computer 500 (e.g., on the workstation 100) is located. Applications with the required credentials can access the server computer 500 to access data from the devices 504 such that the medical facility need only provision the server computer 500 on its LAN and not each device 504 individually. The server computer 500 can communicate with the cloud 514 through an external network, such as the internet.

A user can interact with the server 500 to study the data received from a device 504, to review the analysis provided by the server 500, or to control the server's communication with local databases or local servers 518 or with the remote cloud 514. The user can interact with the server computer 500 directly or through the client device 516.

Although only one server computer 500 is illustrated in the example network communication architecture 502 depicted in FIG. 27, the network communication architecture 502 may include additional server computers 500 that are in communication with the devices 504 of the local mesh network 512. For example, the local server 518 can communicate with one or more of the devices 504. Communications between the local server 518 and the devices 504 can be pre-arranged (meaning that one or more devices 504 may be assigned to each of the local servers 518) or can be set and controlled by a user that has access to one or more of the local servers 518 (e.g., through the client device 516).

In some implementations, the server computer 500 manages the local mesh network 512. For example, the server computer 500 may determine the life-cycle of the local mesh network 512 (e.g., when to turn the local mesh network 512 on or off) or may determine which devices 504 have permission to join the local mesh network 512 at a current time or at a future time.

In a general communication protocol such as Thread, Zigbee, etc., an electronic device accesses a remote server on a cloud to use applications provided by the remote server. However, accessing a remote server (e.g., through the internet) can jeopardize the privacy of medical data. Although the local mesh network 512 can be implemented according to the features of a known communication protocol such as Thread, Zigbee, Bluetooth mesh, etc., the network communication architecture 500 disclosed herein provides distinguishable features from such general communication protocols. For example, while the local mesh network 512 can be implemented according to Thread protocol, unlike a Thread network, the present local mesh network 512 is not in a direct contact with remote servers (or clouds) and operates independently from the connections between the server computer 500 and any remote servers. In other words, the local mesh network 512 continues operating even if the server computer 500 is not in communication with any remote server or if such communication is lost. Similarly, the server computer 500 can continue its operations and communicate with other local servers 518 irrespective of its connection to the cloud 514. In these manners, full functionality of the workstation 100 can be maintained even if the internet connection of the medical facility is lost.

While the above-discussed configurable workstation 100 has been described and illustrated as including components with certain dimensions, sizes, shapes, materials, and configurations, and as being operated according to certain methods, in some embodiments a workstation that is otherwise substantially similar in structure and function to the above-discussed configurable workstation 100 may include one or more components with different dimensions, sizes, shapes, materials, and configurations or may be operated according to methods that include one or more different process flow steps. Additionally, in some embodiments, a workstation that is otherwise similar in construction and function to the above-discussed configurable workstation 100 may not include one or more of the above-discussed system components.

For example, referring to FIG. 28, the air duct system 400 may be disassembled from the frame 200 of the configurable workstation 100 to convert the configurable workstation 100 from a Class II biosafety cabinet to a configurable workstation 110, which, is a Class I laminar flow cabinet (e.g., with or without any of the various modules 300). Accordingly, an airflow path 114 at the workstation 110 is designed to protect any specimens (e.g., product) handled in a workspace 112 from contaminants or other particulates present near the workstation 110, but not personnel working at the workstation 110 and an environment at which the workstation 110 is located.

Accordingly, the configurable workstation 110 includes all of the components of the configurable workstation 100 (e.g., the frame 200, the modules 300, and the server computer 500), except the air duct system 400 (e.g., the duct frame 402, the pressure chamber 406, the fan 408 enclosed therein, and the associated HEPA filter 410).

Removal of the air duct system 400 changes a flow of the air from the airflow path 104 to the airflow path 114. Along the airflow path 114, the fans 260 within the pressure chamber 258 pull air from the surrounding environment through the opening 295 in the upper panel structure 202, through the HEPA filter 262, and into the workspace 112. Instead of being recirculated through the HEPA filter 262, the air instead flows out of the workspace 112 back into the surrounding environment.

The air duct system 400 may be reinstalled to the frame 200 to convert the configurable workstation 110 back into a Class II biosafety cabinet (e.g., back into the configurable workstation 100) as desired. As part of the installation, the duct frame 402 is sealed to inlets of the fans 268 (e.g., at the air ducts 404) and to the rear ends 296 of the slidable air duct 276 (e.g., at the rectangular openings 428). The platform 274 of the table 206 is also sealed to the slidable air duct 276 along the openings 288 and the lateral conduits 294.

While the configurable workstation 100 has been described and illustrated as including the table 206 that has a drawer-style configuration, in some embodiments, a configurable workstation that is otherwise substantially similar in construction and function to the configurable workstation 100 may alternatively include a table with a flip-top configuration. For example, referring to FIG. 29, a table 606 includes an air duct 676 and a platform 674 that can be flipped upward (e.g., pivoted from a rear end) from the air duct 676 to allow access to the air duct 676 for cleaning and sterilization of the air duct 676. The platform 674 defines a front row of openings 688 to allow air to pass into the air duct 676 and a handle 690 for manipulating the platform 674. The table 606 also includes a rear bracket 682 and two lateral brackets 686 for installation of the table 606 to the frame 200 and support of the air duct 676.

While the modules 300 have been described and illustrated as being leveled using counter-directed push and pull mechanisms and sealed using gaskets, in some embodiments, a configurable workstation and modules that are otherwise substantially similar in construction and function to the configurable workstation 100 and the modules 300 may be designed for different types of module leveling and gap-sealing. For example, referring to FIG. 30, in some embodiments, a protector film 702 may be installed atop modules 700 to cover any gaps present between the modules 700, which may themselves be supported by a table platform 704. The protector film 702 also provides a flat work surface atop the modules 700. In some embodiments, as shown in FIG. 31, a module 730 may be equipped with springs or spring-like components 732 that push the module 730 up against one or more flat, level rails 734 or a surface to level the module 730.

In some embodiments, as shown in FIG. 32, modules 706 may be equipped with magnets 708 that pull the modules 706 towards each other laterally to minimize gaps between the modules 706. In some embodiments, as shown in FIG. 33, modules 710 may be connected to each other with one or more cam lock screw mechanisms 712 to minimize gaps between the modules 710. In some embodiments, as shown in FIG. 34, a workstation frame 714 may be designed to apply lateral pressure to a table 716 at which modules 718 are installed to minimize gaps between the modules 718. In some embodiments, as shown in FIG. 35, liquid gasket 720 can be applied between modules 722 and subsequently cured to fill gaps between the modules 722 and provide a smooth transition surface between the modules 722. In some embodiments, as shown in FIG. 36, a module 724 may include a housing 726 formed of a plastic material such that the housing 726 is flexible. Such housing 726 can be compressed with an accessory tool 728 to expand laterally towards adjacent modules 724 to minimize gaps therebetween.

In some embodiments, the configurable workstation 100 may be converted from a Class II biosafety cabinet into a no-hood frame that includes the lower panel structure 204 of the frame 200, the table 206, and any table-top modules 302 installed to the table 206, but does not include the upper panel structure 202 of the frame 200, any wall modules 304, or the air duct system 400. FIG. 37 illustrates such a configurable workstation 900, which includes a frame 902, the server computer 500, the table 206, and a selection of table-top modules 302. The frame 902 is substantially similar in construction and function to the lower panel structure 204 of the frame 200.

While the configurable workstation 100 has been described and illustrated with a configuration in which the server computer 500 is located at the frame 200, in some embodiments of the configurable workstation 100 and the configurable workstation 1000 discussed below, the server computer 500 may be located elsewhere, such as at a location generally near the configurable workstation, but without being installed to the frame. In some embodiments, the server computer 500 may be located at a location relatively remote from the configurable workstation. In some embodiments, the server computer 500 may be provided to a user as a separate module and then installed to the frame by the user onsite.

In some embodiments, a configurable workstation may be designed to circulate air along a flow path that is different from either of the air flow paths 104, 114 described above with respect to the configurable workstation 100. For example, FIGS. 38-45 illustrates such a configurable workstation 1000 that provides an alternative airflow path 1004. With the exception of components and component arrangements that differentiate the airflow path 1004 from the airflow paths 104, 114, the configurable workstation 1000 is otherwise substantially similar in construction and function to the configurable workstation 100. Accordingly, the configurable workstation 1000 is a networked biosafety cabinet that provides a workspace 1002 for carrying out any of the above-mentioned biological protocols in a laboratory environment. Additionally, the configurable workstation 1000 has a modularized design that is customizable on-site at a laboratory to meet any of the various laboratory requirements discussed above and to provide needed functional capabilities. The configurable workstation 1000 therefore includes a frame 800, multiple modules 1300 that may be selectively installed to the frame 800 as desired for customizing a functional profile of the configurable workstation 1000, and the server computer 500, which implements a web application to provide a central user interface for communicating with the configurable workstation 1000.

The frame 800 is generally similar in structure and function to the frame 200 and includes an upper panel structure 802, a lower panel structure 804, and a table 806 that extends horizontally from the upper and lower panel structures 802, 804. The lower panel structure 804 includes a rear panel 808, two lateral panels 810, a front panel 812, and a lower panel 814 that together define an enclosure 816 that houses various components of the configurable workstation 1000. The lower panel structure 804 further includes inner and outer lower rails that together form feet 828 that support the weight of the configurable workstation 1000. The feet 828 are equipped with wheels 840 for optionally rolling the configurable workstation 1000. The lower panel structure further includes inner and outer upper rails that together form upper support beams 830 that in part support the table 806.

The front panel 812 is equipped with multiple power outlets 232 at which any of the modules 1300 or other accessory devices can be powered at the configurable workstation 1000. The enclosure 816 houses several components that are accessible via a service panel 834. For example, the enclosure 816 houses a control module 236 that includes a PCB 238 on which the server computer 500 is implemented, a power supply 240 that powers the configurable workstation 1000, and a power switch module 242 that manages distribution of the power (e.g., such components are illustrated in FIG. 3 with respect to the configurable workstation 100).

The upper panel structure 802 includes a front panel 844 defining an opening 899 at which various modules 1300 can be installed, a front cover 846, and two lateral panels 848. The opening 899 of the front panel 844 has a rectangular shape to accommodate selected modules 1300. The opening 899 typically has a width of about 1.0 m to about 2.0 m and a height of about 0.4 m to about 0.7 m (e.g., 1.08 m in the case of a 4-foot wide frame 800 or 1.67 m in the case of a 6-foot wide frame 800). The front panel 844 is also equipped with two oppositely located electrical outlets 811. The upper panel structure 802 also includes a rear panel 850, an upper panel 852, and a lower panel 854 that together define an enclosure 856 (e.g., a workstation hood) housing various components that are operable to effect air flow at the configurable workstation 1000. The lower panel 854 is also equipped with lights that can illuminate the workspace 1002. The upper panel structure 802 further includes a lower air duct 807 that extends horizontally across the frame 800.

The enclosure 856 is equipped with a pressure chamber 858 housing two sets of oppositely located fans 860, 897 that operate in parallel to provide downward airflow within the frame 800, a HEPA filter 862 located below the pressure chamber 858 for filtering air flowing downward into the workspace 1002, and a HEPA filter 803 for filtering air that flows out of the frame 800. The enclosure 856 also houses triangular brackets 892 for mounting of the fans 860, 897 to the pressure chamber 858. The enclosure 856 is also equipped with an upper air duct 805 that extends horizontally across the enclosure 856 adjacent the rear panel 850. The front cover 846 is openable (e.g., pivotable at the upper panel 852) to switch out the HEPA filter 862 as needed, and the pressure chamber 858 as openable (e.g., pivotable below the upper panel 852) to switch out the HEPA filter 803 as needed.

The upper panel structure 802 further includes lateral panels 868 that in part define the workspace 1002 of the configurable workstation 1000. The lateral panels 868 are transparent or translucent and therefore provide lateral viewing windows for the workspace 1002. Example materials from which the lateral panels 868 may be made include glass, acrylic, or other types of transparent plastic. The lateral panels 848 define upper panel regions 870 that laterally close off the enclosure 856 and lower support beams 872 that in part provide support for the table 806.

The table 806 of the frame 800 includes two side walls 876 that extend forward from the lower air duct 807 and a platform 874 that extends horizontally between the two side walls 876. The platform 874 defines a rectangular opening 878 at which various modules 1300 can be installed to form a flat work surface within the workspace 1002. The opening 878 typically has a width of about 1.0 m to about 2.0 m (e.g., 1.05 m in the case of a 4-foot wide frame 800 or 1.7 m in the case of a 6-foot wide frame 800) and a depth of about 0.4 m to about 0.6 m.

The platform 874 rests atop the side walls 876 and wraps around the side walls 876 along a front edge of the table 806. The table 806 also includes a support rail 864 that extends along a lower edge of the platform 874 and between the side walls 876. The support rail 864 is secured to the platform 874 with fasteners 809. The table 806 further includes an inner rear bracket 882 and an inner front bracket 884 to which the modules 1300 can be attached. The platform 874 also defines a frontal row of elongate openings 888 through which air in the workspace 1002 can flow towards the lower air duct 807. Air can also flow into the lower air duct 807 through an elongate gap 886 defined between and along rear edges of the platform 874 and the lower air duct 807.

The frame 800 is a rigid structure that typically has a total height of about 1.8 m to about 3.0 m, a total width of about 1.0 m to about 2.0 m, and a total depth of about 0.5 m to about 1.0 m. The various components of the frame 800 (e.g., including the upper panel structure 802, the lower panel structure 804, and the table 806) are typically made of one or more materials that can chemically withstand various laboratory cleaning substances. Example materials from which the frame 800 may be made include steel, aluminum, glass, and plastic. The frame 800 (e.g., excluding the modules 1300) typically weighs about 350 lbs to about 1200 lbs.

The modules 1300 are identical in construction and function to any of the modules 300, 700, 710, 718, 722, 724, 730, except that the modules 1300 are additionally equipped with separate wall panels. For example, each module 1300 may be embodied as a table-top module 302 that is provided with a lower wall panel 380 or as a wall module 304 that is provided with a rear wall panel 382. All of the lower wall panels 380 together form a lower wall 880 of the table 806, while all of the rear wall panels 382 together form a rear frame wall 890 of the upper panel structure 802. The wall panels 382 are attached at upper ends to a platform 818 of the upper air duct 805 and attached at lower end to a support rail 820 positioned along the lower air duct 807. The wall panels 380 are secured to the support rail 864 at front ends and to lower air duct 807 at rear ends. The modules 1300 may be installed to the table 806 at the inner brackets 882, 884 with one or more of any of the installation mechanisms and features described above with respect to FIGS. 17-26. In the example configurable workstation 1000, the table-top modules 1300 include two microscope modules 1302q formed to support a microscope for viewing a specimen and two heating plates 1302r with RFID capability, while the wall modules 1300 include two humidity modules 1302s and two monitors 1302t.

Referring to FIGS. 41, 44 and 45, the workstation 1000 is embodied as a Class II biosafety cabinet (e.g., with or without any of the illustrated modules 1300), such that an airflow path 1004 at the workstation 1000 is designed to protect personnel working at the workstation 1000, an environment at which the workstation 1000 is located, and any specimens handled in the workspace 1002 from contaminants or other particulates present near the workstation 1000. Accordingly, the fans 860, 897 within the pressure chamber 858 recirculate air within the workspace 1002 along the airflow path 1004 by flowing the air beneath the platform 874 of the table 806 and back through the HEPA filter 862 before the air reenters the workspace 1002. The airflow path 1004 passes through an interior compartment 892 of the table 806 and an interior compartment 894 of the upper panel structure 802.

For example, air within the workspace 1002 is circulated in a downward direction and then rearwardly into the gap 886, where the air passes into the lower air duct 807. Air within the workspace 1002 is also circulated forwardly into the openings 888 of the platform 874, where the air passes into the interior compartment 892 of the table 806 and then flows into the lower air duct 807. Air within the lower air duct 807 is circulated upward through the interior compartment 894, drawn into the upper air duct 805, and driven downward by the fans 860, 897 through the HEPA filter 862 to remove any harmful particles or contaminants before reentering the workspace 1002. Thus, the fans 860, 897 circulate air along the airflow path 1004 through the workspace 1002, the table 806, and the upper panel structure 802 to meet certain Class II requirements. Serial positioning of two fans (e.g., an upper fan 860 that circulates air to a lower fan 897) reduces a total volume of noise generated by the flow of air at the enclosure 856, as compared to an arrangement that includes only a single fan for air circulation through a workspace.

Other embodiments are also possible. For example, returning to the modular aspect of the above-discussed configurable workstations, any of several modules 300 may be selectively installed to a frame (e.g., the frame 200, 714, 802, 902) of a configurable workstation (e.g., the configurable workstation 100, 110, 800, 1000) as desired for customizing a functional profile of the configurable workstation. For example, in some cases, the tabletop incubator 302*f* may be installed to the configurable workstation in order to provide an incubation functionality for a sample (e.g., a biological specimen) that is temporarily handled at the configurable workstation as part of a lengthy protocol. One example case for utilizing the tabletop incubator 302*f* is the handling and storage of an oocyte for a period of several hours at the configurable workstation as part of an IVF protocol. In some embodiments, the tabletop incubator 302*f* may be embodied as a modular incubator 4000. FIGS. 46-48 illustrate various configurations of such a modular incubator 4000.

The modular incubator 4000 is designed to allow a user to slide a specimen container from an adjacent tabletop surface of the configurable workstation onto a flat, horizontal incubation platform without having to first lift the sample container from the tabletop surface so as to avoid mechanically disturbing the sample and the surrounding interior environment within the container. The modular incubator 4000 includes a support base 4002, a primary lid 4004 that is openable from the support base 4002 to provide access to a designated sample surface area 4018 and is closeable against the support base 4002 to define a sample chamber 4006, a secondary lid 4008 that is openable from the primary lid 4004 to permit viewing of the sample chamber 4006 without mechanically disturbing the sample chamber 4006, and an electronics housing 4010 that houses various internal electronics (e.g., such as internal electronics 3012, 3058 shown in FIG. 56, which may include control circuitry, like hardware 340, firmware 312, and a network communication board 316 for communicating with a server computing device, as well as other electrical components) of the modular incubator 4000. The internal electronics include capabilities to allow the incubator module 4000 to operate in concert with other processes being carried out with at the configurable workstation or as a stand-alone unit.

The support base 4002 includes a generally rectangular enclosure 4014 (e.g., a housing) that may be equipped along exterior edges with any of the fastening mechanisms (e.g., attachment features) described above with respect to the housing 318 of a tabletop module 302 for installation to the frame. Such fastening mechanisms are illustrated schematically as components 4080. The enclosure 4014 defines a flat platform 4016 that is oriented substantially horizontally and flush with a flat tabletop surface of the frame when the modular incubator 4000 is installed to the frame. The sample surface area 4018 is located on the platform 4016 and includes four positional regions 4020 that designate placement of up to four respective sample containers on the platform 4016. In some embodiments, the support base 4002 also includes a generally rectangular, lower enclosure (e.g., such as an enclosure 2056, 3056 shown in FIGS. 49 and 52) that houses additional electronics of the modular incubator 4000.

The support base 4002 also includes a gas distributor 4022 for delivering a flow of gas (e.g., a flow of multiple premixed gasses at selected concentration ratios) to the sample chamber 4006. The gas distributor 4022 extends upward from a central position within the sample surface area 4018 and includes four nozzles 4024 (e.g., outlets) that are oriented and formed to equally distribute the flow of gas towards each of the four positional regions 4020. Such equal distribution of the flow of gas quickens a recovery period for reestablishing desired gas conditions within the sample chamber 4006 once the primary lid 4004 has been closed against the support base 4002 from an open position. The hastened recovery that is facilitated by the equal distribution of the flow of gas can help counter the effects of quick gas escape that may occur due to the lateral and upper walls of the sample chamber 4006 being completely separated from the platform 4016 when the primary lid 4004 is opened. The support base 4002 further includes a gas line (e.g., such as a gas line 3026 shown in FIG. 55) that is routed from a gas inlet (e.g., such as a gas inlet 3062 shown in FIG. 52) on the electronics housing 4010 or on a rear region of the enclosure 4014 to a lower end of the gas distributor 4022 within enclosure 4014. An external source of gas (e.g., a gas canister containing a mixture of gases) may be coupled to the gas inlet.

Additionally, the support base 4002 includes one or more heating elements (e.g., such as a heating mat 3028 shown in FIG. 55 or another type of heating element, such as a heating plate or coil) that are housed within the enclosure 4014 and that are in electrical communication with the internal electronics for heating the sample chamber 4006 to a desired temperature, such as a physiological temperature in a range of about 0° C. to about 50° C. The support base 4002 also includes multiple RFID sensors 4030 (e.g., RFID antennas or readers) that form respective outlines around the positional regions 4020 of the sample surface area 4018. The RFID sensors 4030 can read respective RFID tags that are attached to the sample containers positioned within the positional regions 4020 to identify the samples within the containers. Furthermore, placement of a sample container on a positional region 4020 within a respective outline of an RFID sensor 4030 ensures that there is clearance between the sample container and the primary lid 4004 to prevent the primary lid 4004 from crushing or otherwise damaging or disturbing the sample container during closure of the primary lid 4004 against the support base 4002. In some embodiments, the sample surface area 4018 has a total length of about 8.5 cm to about 16 cm and a total width of about 26 cm to about 48 cm. Example materials from which the enclosure 4014 may be made include a combination of acrylic polymer and alumina trihydrate, or any non-porous ceramic, metal, or plastic.

The primary lid 4004 of the modular incubator 4000 cooperates with the support base 4002 to define the sample chamber 4006 when the primary lid 4004 rests against the support base 4002, as shown in FIGS. 46 and 47. The primary lid 4004 is coupled to the support base 4002 at a hinge (e.g., such as one similar to a hinge 3042 shown in FIGS. 52 and 53) such that the primary lid 4004 is pivotable (e.g., rotatable) between a closed position against the support base 4002 and an open position at an angle of up to about 50 degrees from the support base 4002. The hinge may be embodied as a torque hinge that provides resistance to pivotal motion such that the primary lid 4004 can remain stationary in an open position even after a user releases a hand grip from the primary lid 4004. That is, the primary lid 4004 can remain in the open position until the user manually closes the primary lid 4004.

Referring particularly to FIG. 47, the primary lid 4004 includes a generally rectangular, opaque chamber wall 4032 and a glass window 4034 that is transparent (e.g., or translucent). Any sample containers located within the sample chamber 4006 can be viewed through the glass window 4034 while the secondary lid 4008 is open such that the sample containers do not need to be removed from the sample chamber 4006 for viewing. Avoiding unnecessary handling of the sample containers accordingly avoids any potential for detrimentally disturbing the contained samples and the container environments. The glass window 4034 is positioned within an interior seat 4036 of the chamber wall 4032 and forms a ceiling of the sample chamber 4006. Additionally, the glass window 4034 may be coated with a thin layer of electrically conductive material that helps to disperse heat across the sample chamber 4006. For example, the glass window 4034 may have an indium tin oxide (ITO) coating across its surface. In some examples, a microscope may be used in conjunction with the modular incubator 4000 to view a sample located within the sample chamber 4006 through the glass window 4034. In some embodiments, the glass window 4034 may be equipped with one or more heating elements.

Still referring to FIG. 47, the chamber wall 4032 further defines an upper seat 4038 that supports the secondary lid 4008 in a closed, resting position. The chamber wall 4032 also defines a lip 4040 (e.g., a handling structure) along a front edge of the upper seat 4038 that can be grasped or otherwise moved by a user to open and close the primary lid 4004 (e.g., together with the secondary lid 4008 that is seated against the primary lid 4004). The chamber wall 4032 is typically made of aluminum and serves as an insulator that maintains heat within the sample chamber 4006. The chamber wall 4032 is sufficiently weighted and flat along a lower surface to securely seal against the support base 4002 to form the sample chamber 4006 in the closed position.

The sample chamber 4006 is formed as an inverted pocket or recess within the chamber wall 4032. That is, the chamber wall 4032 defines sidewalls of the sample chamber 4006, while the glass window 4034 forms the ceiling of the sample chamber 4006, as discussed above. The platform 4016 of the support base 4002 forms a lower wall or floor of the sample chamber 4006 when the primary lid 4004 rests against the support base 4002. In the closed position of the primary lid 4004, a gap is present between a top end of the gas distributor 4022 and a lower surface of the glass window

4034 to avoid contact damage to both the gas distributor 4022 and the glass window 4034. Referring to FIG. 48, when the primary lid 4004 in an open position, a user can advantageously slide a sample container across a horizontal tabletop surface of the configurable workstation to a positional region 4020 within the sample surface area 4018 without having to lift the sample container from the tabletop surface and subsequently place the sample container on the positioning region, thereby avoiding a potentially detrimental disturbance of the sample that could otherwise occur during such movements and handling.

The secondary lid 4008 is an opaque component and is coupled to the chamber wall 4032 of the primary lid 4004 at a hinge (e.g., a pin and slot hinge) and is pivotable between a closed position within the upper seat 4038 and an open position at an angle of up to about 50 degrees from the chamber wall 4032. Advantageously, the secondary lid 4008 can be opened to view a sample container through the glass window 4034 while the primary lid 4004 is closed against the support base 4002 to prevent gases and heat within the sample chamber 4006 from escaping, thereby avoiding a deterioration of physiological conditions within the sample chamber 4006.

The secondary lid 4008 includes a lid wall 4044 and one or more internal heating elements (e.g., a heating pad, foil, or plate) contained within the lid wall 4044. Thus, the secondary lid 4008 may cooperate with one or both of the support base 4002 and the glass window 4034 to evenly heat the sample chamber 4006 to a desired physiological temperature during an initial heating period or during a subsequent recovery period after the primary lid 4004 has been closed against the platform 4016 from an open position. The lid wall 4044 defines a handle 4048 (e.g., a tab) along a front edge that can be grasped or otherwise moved by a user to open and close the secondary lid 4008. The lid wall 4044 is typically made of aluminum or another metal.

The electronics housing 4010 defines a receptacle 4050 for supporting a humidification bottle that is in fluid communication with the gas line within the electronics housing 4010 to humidify the flow of gas as necessary to maintain a physiological level of humidity within the sample chamber 4006. Additionally, the electronics housing 4010 supports a power connector and a power switch (e.g., such as the power connector 3070 and the power switch 3072 shown in FIG. 57) along a rear wall for powering the modular incubator 4000. The electronics housing 4010 also supports a user interface 4052 at which a user can view displayed information (e.g., a sample identity determined by RFID detection, or other information) and at which the user can set, input, or otherwise control desired conditions (e.g., a gas flow rate, a temperature, a humidity level, or a power state) at the modular incubator 4000.

The internal electronics within the electronics housing 4010 may also be configured to adjust one or more operational parameters automatically to maintain user-set conditions within the sample chamber 4006 based on an open or closed state of the primary lid 4004 and a duration of an open or closed state, as detected by a sensor mechanism (e.g., such as the sensor mechanism 3054 shown in FIG. 52) located at both the primary lid 4004 and the support base 4002. In some examples, the sensor mechanism may be embodied as a contact sensor with a magnet. For example, upon closure of the primary lid 4004 from an open state, the internal electronics may operate to cause a humidified gas flow to be delivered to the sample chamber 4006 at a relatively fast rate to restore the sample chamber 4006 to desired conditions as soon as possible. In some examples, user-set conditions (e.g., including temperature, gas concentrations, and humidity) may be reestablished during a recovery period in as fast as ten seconds.

While the modular incubator 4000 has been described and illustrated as including a transparent window 4034 that is surrounded by an opaque chamber wall, in some embodiments, a modular incubator that is similar in function to the modular incubator 4000 may alternatively include a transparent sample chamber. FIGS. 49-51 illustrate such a modular incubator 2000. The modular incubator 2000 includes a support base 2002, a transparent chamber wall 2008 (e.g., an inner lid) that is openable from the support base 2002 to provide access to a designated sample surface area 2018 and is closeable against the support base 2002 to define a sample chamber 2006, an outer lid 2004 that is openable from the support base 2002 to permit viewing of the chamber wall 2008 without mechanically disturbing the sample chamber 2006, and an electronics housing 2010 that houses various internal electronics of the modular incubator 2000.

The support base 2002 includes a generally rectangular, upper enclosure 2014 (e.g., a housing) that may be equipped along exterior edges with any of the fastening mechanisms described above with respect to the housing 318 of a tabletop module 302 for installation to the frame of the configurable workstation. Such fastening mechanisms are illustrated schematically as components 2080. The enclosure 2014 defines a flat platform 2016 that is oriented substantially horizontally and flush with a flat tabletop surface of the frame when the modular incubator 2000 is installed to the frame. The sample surface area 2018 is located on the platform 2016 and may include multiple positional regions (e.g., such as positional regions 4020, 3020 shown in FIGS. 48 and 54) that designate placement of sample containers on the platform 2016. The support base 2002 also includes a generally rectangular, lower enclosure 2056 (e.g., a housing) that houses additional internal electronics of the modular incubator 2000. The internal electronics within either or both of the electronics housing 2010 or the lower enclosure 2056 (e.g., such as the internal electronics 3012, 3058 shown in FIG. 56) may include control circuitry, like hardware 310, firmware 312, and a network communication board 316 for communicating with a server computing device, as well as other electrical components. The internal electronics include capabilities to allow the incubator module 2000 to operate in concert with other processes being carried out with at the configurable workstation or as a stand-alone unit.

The support base 2002 also includes a centrally positioned gas distributor (e.g., such as the gas distributor 1022, 3022 shown in FIGS. 48 and 54) for delivering a flow of gas (e.g., a flow of multiple premixed gasses at selected concentration ratios) to the sample chamber 2006. As discussed with respect to the gas distributors 4022, 3022, the gas distributor may extend upward from a central position within the sample surface area 2018 and includes two nozzles that are oriented and formed to equally distribute the flow of gas between each of the positional regions to facilitate quick recovery of gas conditions within the sample chamber 2006. The support base 2002 further includes a gas line (e.g., such as the gas line 3026 shown in FIG. 55) that is routed from a gas inlet (e.g., such as the gas inlet 3062 shown in FIG. 52) on the electronics housing 2010 or on a rear region of the upper enclosure 2014 to a lower end of the gas distributor within the enclosure 2014. An external source of gas may be coupled to the gas inlet.

Additionally, the support base 2002 includes one or more heating elements (e.g., such as the heating mat 3028 shown in FIG. 55 or another type of heating element) within the upper enclosure 2014 and that are in electrical communication with either or both of the internal electronics for heating the sample chamber 2006 to a desired temperature. The support base 2002 also includes multiple RFID sensors (e.g., such as the RFID sensors 4020, 3020 shown in FIGS. 48 and 54) that form respective outlines around positional regions of the sample surface area 2018 to identify the samples within the containers. Example materials from which the enclosures 2014, 2056 may be made include cast urethane, plastic, and metal.

The chamber wall 2008 of the modular incubator 2000 is a generally rectangular component and cooperates with the support base 2002 to define the sample chamber 2006 when the chamber wall 2008 rests against the support base 2002, as shown in FIG. 49. The chamber wall 2008 is coupled to the support base 2002 at a hinge such that the chamber wall 2008 is pivotable (e.g., rotatable) between a closed position against the support base 2002 and an open position at an angle of up to about 50 degrees from the support base 2002. The hinge may be embodied as a torque hinge that provides resistance to pivotal motion such that the chamber wall 2008 can remain stationary in an open position even after a user releases a hand grip from the chamber wall 2008, as discussed above with respect to the primary lid 1004 of the modular incubator 1000.

Referring to FIG. 50, any sample containers located within the sample chamber 2006 can be viewed through the chamber wall 2008 while the outer lid 2004 is open such that the sample containers do not need to be removed from the sample chamber 2006 for viewing. Furthermore, the sample containers can be viewed from multiple angles since the entire chamber wall 2008 is transparent. In some embodiments, the chamber wall 2008 may be made of one or more plastics, such that the chamber wall 2008 can be removed, cleaned, sterilized, and reinstalled to the platform 2016. Example plastic materials from which the chamber wall 2008 may be made include cast ultraclean urethane and other transparent materials. In some embodiments, the chamber wall 2008 may be made of a glass material, such as cast ultraclean urethane or other transparent materials. In some examples, a microscope may be used in conjunction with the modular incubator 2000 to view a sample located within the sample chamber 2006 through the chamber wall 2008.

The chamber wall 2008 further defines a handle 2040 (e.g., a tab) that protrudes from a front edge and that can be grasped or otherwise moved by a user to open and close the chamber wall 2008 (e.g., together with the outer lid 1004 that will be carried along with the chamber wall 2008 at a complementary shaped, recessed cutout 2032, as shown in FIG. 51). The chamber wall 2008 is sufficiently weighted and flat along a lower surface to securely seal against the support base 2002 to form the sample chamber 2006 in the closed position. In some embodiments, the chamber wall 2008 typically has a weight of about 100 g to about 350 g. The chamber wall 2008 may be equipped with an interior gasket (e.g., such as a gasket 3064 shown in FIG. 56), which helps to provide a seal against the support base 2002.

The chamber wall 2008 is formed as an inverted pocket. That is, the chamber wall 2008 defines sidewalls and an upper wall of the sample chamber 2006, while the platform 2016 of the support base 2002 forms a lower wall or floor of the sample chamber 2006 when the chamber wall 2008 rests against the support base 2002. In the closed position of the chamber wall 2008, a gap is present between a top end of the gas distributor and a ceiling of the chamber wall 2008 to avoid contact damage to both the gas distributor and the chamber wall 2008. Referring to FIG. 51, with the chamber wall 2008 in an open position, a user can advantageously slide a sample container across a horizontal tabletop surface of the configurable workstation to a positional region within the sample surface area 2018 without having to lift the sample container from the tabletop surface and subsequently place the sample container on the positioning region, thereby avoiding a potentially detrimental disturbance of the sample that could otherwise occur during such movements and handling.

The outer lid 2004 is an opaque component and is coupled to the chamber wall 2008 at a hinge 2042 (e.g., a pin and slot hinge) and is pivotable between a closed position against the platform 2016 and an open position at an angle of up to about 50 degrees from the platform 2016. The outer lid 2004 is generally rectangular component and is typically made of aluminum to provide insulation that maintains heat within the sample chamber 2006.

Advantageously, the outer lid 2004 can be opened to view a sample container through the chamber wall 2008 while the chamber wall 2008 is closed against the support base 2002 to prevent gases and heat within the sample chamber 2006 from escaping, thereby avoiding a deterioration of physiological conditions within the sample chamber 2006. The outer lid 2004 includes a lid wall 2044 and a heating element or mechanism (e.g., such as the heater assembly 3046 shown in FIG. 58) contained within or positioned within the lid wall 2044. Thus, the outer lid 2004 can cooperate with the support base 2002 to evenly heat the sample chamber 2006 to a desired physiological temperature during an initial heating period or during a subsequent recovery period after both the chamber wall 2008 and the outer lid 2004 have been closed against the platform 2016 from an open position. The lid wall 2044 defines a handle 2048 (e.g., a tab) along a front edge that can be grasped or otherwise moved by a user to open and close the outer lid 2004. The lid wall 2044 is typically made of metal.

The electronics housing 2010 defines a receptacle 2050 for supporting a humidification bottle that is in fluid communication with the gas line within the electronics housing 2010 to humidify the flow of gas as necessary to maintain a physiological level of humidity within the sample chamber 2006. Additionally, either the electronics housing 2010 or the lower enclosure 2056 supports a power connector and a power switch (e.g., such as the power connector 3070 and the power switch 3072 shown in FIG. 57) along a rear wall for powering the modular incubator 2000. The electronics housing 2010 also supports a user interface 2052 at which a user can view displayed information and at which the user can set, input, or otherwise control desired conditions, as discussed above with respect to the modular incubator 1000. As similarly discussed above with respect to the incubator module 4000, the internal electronics within the electronics housing 2010 and the lower enclosure 2056 may be configured to adjust one or more operational parameters automatically to maintain user-set conditions within the sample chamber 2006 based on an open or closed state of the chamber wall 2008 and a duration of an open or closed state, as detected by a sensor mechanism (e.g., such as the sensor mechanism 3054 shown in FIG. 52) located at both the chamber wall 2008 and the support base 2002. In some examples, the sensor mechanism may be embodied as a contact sensor with a magnet.

FIGS. 52-58 illustrate another modular incubator 3000 that includes a transparent sample chamber and which is similar in construction and function to the modular incubator 2000. The modular incubator 3000 includes a support base

3002, a transparent chamber wall 3008 (e.g., an inner lid) that is openable from the support base 3002 to provide access to a designated sample surface area 3018 and is closeable against the support base 3002 to define a sample chamber 3006, an outer lid 3004 that is openable from the support base 3002 to permit viewing of the chamber wall 3008 without mechanically disturbing the sample chamber 3006, and an electronics housing 3010 that houses various electronics 3012 of the modular incubator 3000.

The support base 3002 includes a generally rectangular, upper enclosure 3014 (e.g., a housing) that may be equipped along exterior edges with any of the fastening mechanisms described above with respect to the housing 318 of a tabletop module 302 for installation to the frame of the configurable workstation. Such fastening mechanisms are illustrated schematically as components 3080. The enclosure 3014 defines a flat platform 3016 that is oriented substantially horizontally and flush with a flat tabletop surface of the frame of the configurable workstation when the modular incubator 3000 is installed to the frame. The sample surface area 3018 is located on the platform 3016 and includes two positional regions 3020 that designate placement of up to two respective sample containers on the platform 3016. The support base 3002 also includes a generally rectangular, lower enclosure 3056 (e.g., a housing) that houses additional electronics 3058 of the modular incubator 3000. Either of the electronics 3012 or the electronics 3058 may include control circuitry, such as hardware 310, firmware 312, and a network communication board 316 for communicating with a server computing device, as well as other electrical components. The electronics 3012, 3056 include capabilities to allow the incubator module 3000 to operate in concert with other processes being carried out with at the configurable workstation or as a stand-alone unit.

Referring to FIGS. 54 and 55, the support base 3002 also includes a gas distributor 3022 for delivering a flow of gas (e.g., a flow of multiple premixed gasses at selected concentration ratios) to the sample chamber 3006. The gas distributor 3022 extends upward from a central position within the sample surface area 3018 and includes two nozzles 3024 that are oriented and formed to equally distribute the flow of gas between each of the two positional regions 3020 to facilitate quick recovery of gas conditions within the sample chamber 3006, as discussed above with respect to the gas distributors of the modular incubators 4000, 2000. The support base 3002 further includes a gas line 3026 that is routed from a gas inlet 3062 on the electronics housing 3010 to a lower end of the gas distributor 3022 within the enclosure 3014. An external source of gas may be coupled to the gas inlet 3062.

Additionally, the support base 3002 includes a heating mat 3028 within the upper enclosure 3014 that is in electrical communication with either or both of the electronics 3012, 3058 for heating the sample chamber 3006 to a desired temperature. The support base 3002 also includes multiple RFID sensors 3030 (e.g., RFID antennas or readers) that form respective outlines around the positional regions 3020 of the sample surface area 3018 for reading respective RFID tags that are attached to the sample containers positioned within the positional regions 3020 to identify the samples within the containers. Furthermore, placement of a sample container on a positional region 3020 within a respective outline of an RFID sensor 3030 ensures that there is clearance between the sample container and the chamber wall 3008 to prevent the chamber wall 3008 from crushing or otherwise damaging or disturbing the sample container during closure of the chamber wall 3008 against the support base 3002. In some embodiments, the sample surface area 3018 has a total length of about 8.5 cm to about 16 cm and a total width of about 26 cm to about 48 cm. The enclosures 3014, 3056 may be made of the same materials discussed above for the enclosures 2014, 2056.

The chamber wall 3008 of the modular incubator 3000 is a generally rectangular component and cooperates with the support base 3002 to define the sample chamber 3006 when the chamber wall 3008 rests against the support base 3002, as illustrated for the chamber wall 2008 of the modular incubator 2000 in FIG. 49. The chamber wall 3008 is coupled to the support base 3002 at a hinge 3060 such that the chamber wall 3008 is pivotable (e.g., rotatable) between a closed position against the support base 3002 and an open position at an angle of up to about 50 degrees from the support base 3002. The hinge 3060 may be embodied as a torque hinge that provides resistance to pivotal motion such that the chamber wall 3008 can remain stationary in an open position even after a user releases a hand grip from the chamber wall 3008, as discussed above with respect to the chamber wall 2008 of the modular incubator 2000.

Any sample containers located within the sample chamber 3006 can be viewed through the chamber wall 3008 while the outer lid 3004 is open (e.g., as illustrated for the outer lid 2004 of the modular incubator 2000 in FIG. 50) such that the sample containers do not need to be removed from the sample chamber 3006 for viewing. Furthermore, the sample containers can be viewed from multiple angles since the entire chamber wall 3008 is transparent. In some embodiments, the chamber wall 3008 may be made of one or more plastics, such that the chamber wall 3008 can be removed, cleaned, sterilized, and reinstalled to the platform 3016. The chamber wall 3008 may be made of any of the plastic or glass materials discussed above with respect to the chamber wall 2008. A microscope may also be used in conjunction with the modular incubator 3000 to view a sample located within the sample chamber 3006 through the chamber wall 3008.

The chamber wall 3008 further defines a recessed handle 3040 (e.g., a triangular pocket) that extends along a front edge and that can be grasped or otherwise moved by a user to open and close the chamber wall 3008 (e.g., together with the outer lid 3004 that will be carried along with the chamber wall 3008 at a complementary shaped, recessed cutout 3032). The chamber wall 3008 is sufficiently weighted and flat along a lower surface to securely seal against the support base 3002 to form the sample chamber 3006 in the closed position. In some embodiments, the chamber wall 3008 typically has a weight of about 100 g to about 350 g. Referring to FIGS. 53 and 56, the chamber wall 3008 has a double-layer construction and is equipped with an interior gasket 3064 that extends around a peripheral edge within the double-layer construction. The gasket 3064 helps to provide a seal against the support base 3002.

The chamber wall 3008 is formed as an inverted pocket. That is, the chamber wall 3008 defines sidewalls and an upper wall of the sample chamber 3006, while the platform 3016 of the support base 3002 forms a lower wall or floor of the sample chamber 3006 when the chamber wall 3008 rests against the support base 3002. In the closed position of the chamber wall 3008, a gap is present between a top end of the gas distributor 3022 and a ceiling of the chamber wall 3008 to avoid contact damage to both the gas distributor 3022 and the chamber wall 3008. With the chamber wall 3008 in an open position (e.g., as illustrated for the chamber wall 2008 of the modular incubator 2000 in FIG. 51), a user can advantageously slide a sample container across a horizontal tabletop surface of the configurable workstation to a positional region 3020 within the sample surface area 3018 without having to lift the sample container from the tabletop surface and subsequently place the sample container on the positioning region, thereby avoiding a potentially detrimental disturbance of the sample that could otherwise occur during such movements and handling.

Referring to FIG. 52, the outer lid 3004 is an opaque component and is coupled to the chamber wall 3008 at a hinge 3042 (e.g., a pin and slot hinge) and is pivotable between a closed position against the platform 3016 and an open position at an angle of up to about 50 degrees from the platform 3016. The outer lid 3004 is generally rectangular component and is typically made of aluminum to provide insulation that maintains heat within the sample chamber 3006. Advantageously, the outer lid 3004 can be opened to view a sample container through the chamber wall 3008 while the chamber wall 3008 is closed against the support base 3002 to prevent gases and heat within the sample chamber 3006 from escaping, thereby avoiding a deterioration of physiological conditions within the sample chamber 3006.

Referring to FIG. 58, the outer lid 3004 includes a lid wall 3044 that is equipped with a heater assembly 3046. The heater assembly 3046 has a stacked plate configuration that extends along a length of the chamber wall 3008. The heater assembly 3046 is secured to the lid wall 3044 in an inverted pocket 3066. Thus, the outer lid 3004 can cooperate with the support base 3002 to evenly heat the sample chamber 3006 to a desired physiological temperature during an initial heating period or during a subsequent recovery period after both the chamber wall 3008 and the outer lid 3004 have been closed against the platform 3016 from an open position. The lid wall 3044 defines a recessed handle 3048 (e.g., opposing triangular pockets) along a front edge that can be grasped or otherwise moved by a user to open and close the outer lid 3004. The lid wall 3044 is typically made of the same materials from which the lid wall 2044 of the modular incubator 2000 is made.

Referring to FIGS. 52-54, the electronics housing 3010 defines a receptacle 3050 for supporting a humidification bottle that is in fluid communication with the gas line 3026 within the electronics housing 3010 to humidify the flow of gas as necessary to maintain a physiological level of humidity within the sample chamber 3006. The electronics housing 3010 also supports the gas inlet 3062 at which the flow of gas is delivered to the gas line 3026 for the gas distributor 3022. The electronics housing 3010 further supports a gas outlet 3068 at which the mixed gas (e.g., in some examples, Ni-90%, $O_2$-5%, and $CO_2$-5%) enters the gas manifold from an external source of gas. The gas then, via the gas manifold inner channels, is directed through a proportional valve into the flowmeter valve, returns to the gas manifold and enters into the bottle where water vapors are added to the gas, returns to the gas manifold, and is then directed to the working chamber.

Referring to FIGS. 52-54 and 57, the lower enclosure 3056 supports a power connector 3070 and a power switch 3072 along a rear wall for powering the modular incubator 3000. The electronics housing 3010 also supports a user interface 3052 at which a user can view displayed information and at which the user can set, input, or otherwise control desired conditions, as discussed above with respect to the modular incubators 4000, 2000. As similarly discussed above with respect to the internal electronics of the modular incubators 4000, 2000, the internal electronics 3012, 3058 may be configured to adjust one or more operational parameters automatically to maintain user-set conditions within the sample chamber 3006 based on an open or closed state of the chamber wall 3008 and a duration of an open or closed state based on a sensor mechanism 3054 located both within the chamber wall 3008 (e.g., behind the handle 3040) and at the support base 3002 (e.g., below the handle 3040), such as a contact sensor with a magnet.

While the modular incubators 2000, 3000, 4000 have been described and illustrated as including sample surface areas 3018, 4018 with four or two positional regions for placement of sample containers, in some embodiments, a modular incubator that is otherwise substantially similar in construction and function to any of the modular incubators 2000, 3000, 4000 may instead include a sample surface area with a different number of positional regions for placement of a respective number of sample containers.

Other embodiments are also within the scope of the following claims.

What is claimed is:

1. A workstation comprising:
a flat work surface area having a width of about 1.0 m to about 2.0 m;
a frame supporting the flat work surface area, the flat work surface area and the frame together defining a workspace for carrying out a scientific protocol;
a flat incubation surface area lying adjacent to and flush with the flat work surface area and defining a sample placement area on which a sample container can be positioned for incubating a sample contained therein, the sample placement area lying flush with the flat work surface area such that the sample container can be slid from the flat work surface area onto the sample placement area without lifting the sample container from the flat work surface area; and
a chamber wall structure providing an incubation functionality at the workstation, the chamber wall structure coupled to the flat incubation surface area and pivotable between:
a closed position against the flat incubation surface area to form a sample chamber in which the sample container can be placed for incubating the sample contained therein, and
an open position in which a front end of the chamber wall structure is spaced apart from the flat incubation surface area to allow access to the sample placement area,
wherein the flat incubation surface area forms a lower wall of the sample chamber, and
wherein the lower wall of the sample chamber provides the sample placement area that lies flush with the flat work surface area,
wherein the workstation is a Class II biosafety cabinet.

2. The workstation of claim 1, wherein the frame comprises an upper panel structure that at least in part defines the workspace.

3. The workstation of claim 2, wherein the frame comprises a table structure disposed beneath the upper panel structure and that at least in part supports the flat work surface area.

4. The workstation of claim 3, wherein the frame comprises a lower panel structure disposed beneath the table structure.

5. The workstation of claim 1, further comprising an airflow system mounted to the frame and providing an airflow path that extends through the workspace.

6. The workstation of claim 1, wherein the sample placement area is flat continuously between a first end of the sample placement area and a second end of the sample placement area that is located oppositely from the first end.

7. The workstation of claim 1, wherein the chamber wall structure has a rectangular cross-sectional shape.

8. The workstation of claim 1, wherein the chamber wall structure comprises a sealing member that extends along a sidewall of the chamber wall structure for sealing the chamber wall structure to the flat incubation surface area in the closed position.

9. The workstation of claim 1, wherein the chamber wall structure is coupled to the flat incubation surface area at a torque hinge.

10. The workstation of claim 9, wherein the torque hinge is positioned at a first end of the chamber wall structure, and wherein the chamber wall structure comprises a handle positioned at a second end of the chamber wall structure, the second end located oppositely from the first end.

11. The workstation of claim 1, wherein the chamber wall structure comprises one or more heating elements.

12. The workstation of claim 11, wherein the one or more heating elements comprise a heating plate.

13. The workstation of claim 11, wherein at least one of the one or more heating elements is positioned adjacent a top wall of the chamber wall structure.

14. The workstation of claim 1, further comprising one or more heating elements positioned adjacent the flat incubation surface area.

15. The workstation of claim 1, further comprising a gas nozzle extending upward from the flat incubation surface area to deliver a gas to the sample chamber.

16. The workstation of claim 15, further comprising a gas line positioned beneath the flat incubation surface area and fluidically coupled to the gas nozzle.

17. The workstation of claim 1, further comprising an RFID sensor positioned along the flat incubation surface area.

18. The workstation claim 1, further comprising a positional feature that defines the sample placement area.

19. The workstation of claim 1, further comprising a user interface for inputting one or more operational parameters that determine one or more conditions within the sample chamber.

20. The workstation of claim 1, further comprising a plate structure disposed beneath the flat incubation surface area.

21. The workstation of claim 1, wherein the scientific protocol comprises an assisted reproductive technology (ART) protocol.

22. A modular incubator comprising:
a housing comprising one or more fastening mechanisms for attachment to a workstation frame;
a platform located at the housing and defining a sample placement area that comprises a plurality of positional regions for respective placement of a plurality of sample containers;
a gas distributor located at a center position of the sample placement area;
a chamber wall structure coupled to the platform and pivotable between:
a closed position against the platform to form a sample chamber, and
an open position in which a front end of the chamber wall structure is spaced apart from the platform to allow access to the sample placement area; and
a lid coupled to and openable from the chamber wall structure to expose at least a portion of the chamber wall structure for viewing.

23. A modular incubator comprising:

a housing comprising one or more fastening mechanisms for attachment to a workstation frame;

a platform located at the housing and defining a sample placement area that comprises a plurality of positional regions for respective placement of a plurality of sample containers;

a plurality of RFID sensors respectively associated with the plurality of positional regions;

a chamber wall structure coupled to the platform and pivotable between:

a closed position against the platform to form a sample chamber, and an open position in which a front end of the chamber wall structure is spaced apart from the platform to allow access to the sample placement area; and a lid coupled to and openable from the chamber wall structure to expose at least a portion of the chamber wall structure for viewing.

* * * * *